(12) United States Patent
Shizu et al.

(10) Patent No.: US 9,660,199 B2
(45) Date of Patent: May 23, 2017

(54) COMPOUND, LIGHT-EMITTING MATERIAL, AND ORGANIC LIGHT-EMITTING DEVICE

(71) Applicant: KYULUX, INC., Fukuoka (JP)

(72) Inventors: Katsuyuki Shizu, Fukuoka (JP);
Hiroyuki Tanaka, Fukuoka (JP);
Hajime Nakanotani, Fukuoka (JP);
Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 211 days.

(21) Appl. No.: 14/379,567

(22) PCT Filed: May 10, 2013

(86) PCT No.: PCT/JP2013/063112
§ 371 (c)(1),
(2) Date: Aug. 19, 2014

(87) PCT Pub. No.: WO2013/172255
PCT Pub. Date: Nov. 21, 2013

(65) Prior Publication Data
US 2015/0041784 A1    Feb. 12, 2015

(30) Foreign Application Priority Data

| May 17, 2012 | (JP) | 2012-113654 |
| Feb. 25, 2013 | (JP) | 2013-034967 |

(51) Int. Cl.
| H01L 51/54 | (2006.01) |
| C09K 11/06 | (2006.01) |
| H01L 51/00 | (2006.01) |
| C07D 401/10 | (2006.01) |
| C07D 403/10 | (2006.01) |
| C07D 403/14 | (2006.01) |
| C07D 413/10 | (2006.01) |
| C07D 417/10 | (2006.01) |
| C07D 413/14 | (2006.01) |
| C07D 413/04 | (2006.01) |
| C07D 251/24 | (2006.01) |
| H01L 51/50 | (2006.01) |

(52) U.S. Cl.
CPC ........ *H01L 51/0067* (2013.01); *C07D 251/24* (2013.01); *C07D 401/10* (2013.01); *C07D 403/10* (2013.01); *C07D 403/14* (2013.01); *C07D 413/04* (2013.01); *C07D 413/10* (2013.01); *C07D 413/14* (2013.01); *C07D 417/10* (2013.01); *C09K 11/06* (2013.01); *H01L 51/0071* (2013.01); *H01L 51/0072* (2013.01); *H01L 51/5016* (2013.01); *C09K 2211/1007* (2013.01); *C09K 2211/1011* (2013.01); *C09K 2211/1014* (2013.01); *C09K 2211/1033* (2013.01); *C09K 2211/1037* (2013.01); *C09K 2211/1044* (2013.01); *C09K 2211/1059* (2013.01); *H01L 51/5012* (2013.01); *H01L 2251/5376* (2013.01)

(58) Field of Classification Search
None
See application file for complete search history.

(56) References Cited

U.S. PATENT DOCUMENTS

| 6,869,699 B2 | 3/2005 | Klubek et al. |
| 8,766,249 B2 | 7/2014 | Sawada et al. |

(Continued)

FOREIGN PATENT DOCUMENTS

| EP | 2665342 A1 | 11/2013 |
| JP | 2002193952 A | 7/2002 |

(Continued)

OTHER PUBLICATIONS

Machine translation of JP2002-193952. Date of publication: Jul. 10, 2002.*

(Continued)

*Primary Examiner* — Andrew K Bohaty
(74) *Attorney, Agent, or Firm* — Browdy and Neimark, PLLC

(57) ABSTRACT

A compound represented by the general formula (1) is useful as a light-emitting material. In the general formula (1), $Ar^1$ to $Ar^3$ represent an aryl group, provided that at least one thereof represents an aryl group substituted by a group represented by the general formula (2). In the general formula (2), $R^1$ to $R^8$ represent a hydrogen atom or a substituent; Z represents O, S, O=C or $Ar^4$—N; and $Ar^4$ represents an aryl group.

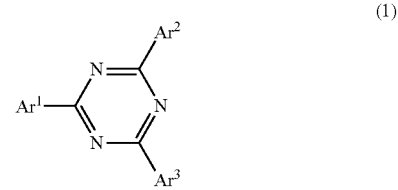

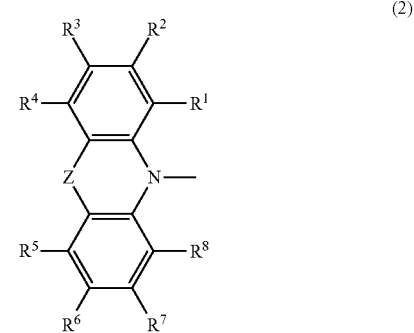

14 Claims, 14 Drawing Sheets

(56) References Cited

U.S. PATENT DOCUMENTS

| | | |
|---|---|---|
| 2005/0225236 A1 | 10/2005 | Nomura et al. |
| 2012/0097899 A1 | 4/2012 | Parham et al. |
| 2012/0217869 A1 | 8/2012 | Adachi et al. |
| 2012/0241732 A1 | 9/2012 | Endo et al. |
| 2012/0248968 A1 | 10/2012 | Ogiwara et al. |
| 2014/0061548 A1 | 3/2014 | Montenegro et al. |
| 2014/0070146 A1 | 3/2014 | Parham et al. |

FOREIGN PATENT DOCUMENTS

| | | | |
|---|---|---|---|
| JP | 2005306862 | A | 11/2005 |
| JP | 4404473 | B2 | 1/2010 |
| JP | 201031259 | A | 2/2010 |
| JP | 201045034 | A | 2/2010 |
| JP | 2012116784 | A1 | 6/2012 |
| JP | 2012193352 | A | 10/2012 |
| JP | 5163837 | B2 | 3/2013 |
| WO | 2010126270 | A1 | 11/2010 |
| WO | 2011000455 | A1 | 1/2011 |
| WO | 2011070963 | A1 | 6/2011 |
| WO | 2012050002 | A1 | 4/2012 |
| WO | 2012133188 | A1 | 10/2012 |
| WO | 2012149999 | A1 | 11/2012 |

OTHER PUBLICATIONS

Machine translation of JP2010-031259. Date of publication: Feb. 12, 2010.*
Office Action dated Apr. 18, 2016 in corresponding Chinese application No. 201380004283.0.
Office Action dated Sep. 6, 2015, in corresponding Chinese application No. 201380004283.
Tanaka et al "Efficient green thermally activated delayed fluorescence (TADF) form a phenoxazine-triphenyltriazine (PXZ-TRZ) derivative" Chemical Communications 48:93: 11392-11394 (Sep. 2012).
Endo et al "Efficient up-conversion of triplet excitons into a singlet state and its application for organic light emitting diodes" Applied Physics Letters 98:8: 083302/1-1-083302/3 (Feb. 2011).
Wang et al "Optical limiting properties and ultrafast dynamics of six-branched styryl derivatives based on 1,3,5-triazine" Journal of Applied Physics Letter 110:3 033518/1-1-033518/10 (Aug. 2011).
International Preliminary Report dated Nov. 20, 2014. Application No. 2013063112.
Japanese Office Action dated May 20, 2014, issued in corresponding Japanese Patent applicaion No. 2013034967.
International search report, dated Jun. 18, 2013. Application No. 2013063112.
Chinese Office Action for Chinese Patent Application 201380004283.0 dated Nov. 2, 2016 and English Translation.

* cited by examiner

COMPOUND, LIGHT-EMITTING MATERIAL, AND ORGANIC LIGHT-EMITTING DEVICE

TECHNICAL FIELD

The present invention relates to a compound that is useful as a light-emitting material, and an organic light-emitting device using the same.

BACKGROUND ART

Organic light-emitting devices, such as an organic electroluminescent device (organic EL device), have been actively studied for enhancing the light emission efficiency, where light emission efficiency is defined and hereafter used for mean photoluminescence quantum efficiency, electroluminescence quantum efficiency, or both as appropriate thereof. In particular, various studies for enhancing the light emitting efficiency have been made by newly developing and combining an electron transporting material, a hole transporting material, a light-emitting material and the like constituting an organic electroluminescent device. There are studies relating to an organic electroluminescent device utilizing a compound containing a 1,3,5-triazine structure and a compound containing a phenazine structure, which are found among them, and some proposals have been made hitherto.

For example, PTL 1 describes a compound containing a 1,3,5-triazine structure represented by the following general formula, which is contained not in between two electrodes but in a layer formed outside the electrodes, and thereby the light efficiency is improved. In the general formula, $Ar_2$, $Ar_4$ and $Ar_6$ each represent a phenylene group or the like, b, d and f each represent an integer of one of from 0 to 3, and $R_2$, $R_4$ and $R_6$ each are selected from a wide range of groups including a hydrogen atom, a halogen atom, an alkyl group and an aryl group. However, there is no group described for $R_2$, $R_4$ and $R_6$ that contains a phenoxazine structure, a phenothiazine structure or a phenazine structure.

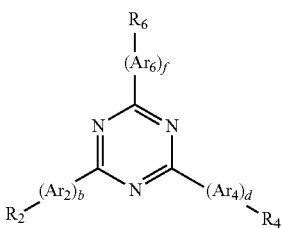

PTL 2 describes the use of a compound containing a phenazine structure represented by the following general formula as a host material of an organic electroluminescent device and the like. In the general formula, $R_1$ to $R_8$ each represent a hydrogen atom, an alkyl group, an aryl group or the like, and $R_9$ and $R_{10}$ each represent a hydrogen atom, an alkyl group, an aryl group, a heterocyclic group or an alkenyl group. However, there is no group described for $R_9$ and $R_{10}$ that contains a 1,3,5-triazine structure.

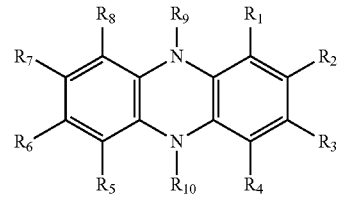

CITATION LIST

Patent Literatures

PTL 1: JP-A-2010-45034
PTL 2: U.S. Pat. No. 6,869,699

SUMMARY OF INVENTION

Technical Problem

As described above, compounds containing a 1,3,5-triazine structure and a compound containing a phenazine structure has been studied, and some proposals relating to application thereof to an organic electroluminescent device have been made. However, a compound containing in the molecule thereof a 1,3,5-triazine structure along with a phenoxazine structure, a phenothiazine structure or a phenazine structure has almost not been specifically studied. In particular, a compound containing a 2,4,6-triaryl-1,3,5-triazine structure along with a phenoxazine structure, a phenothiazine structure or a phenazine structure has not been reported even for a synthesis example thereof. Accordingly, it is extremely difficult to predict accurately properties that are exhibited by the compound having a combination of the structure. In particular, for the usefulness thereof as a light-emitting material, it is difficult to find any literature capable of becoming the basis of prediction of the usefulness, as apparent from PTL 1 and PTL 2, which fail to describe a purpose as a light-emitting material.

The present inventors have performed investigations with the aim of synthesizing a compound containing in the molecule thereof a 1,3,5-triazine structure along with a phenoxazine structure, a phenothiazine structure or a phenazine structure, and evaluating the compound for usefulness as a light-emitting material. The inventors have further performed earnest investigations with the aim of evolving a general formula of a compound that is useful as a light-emitting material, and generalizing a structure of an organic light-emitting device having a high light emission efficiency.

Solution to Problem

As a result of earnest investigations for achieving the objects, the inventors have succeeded at synthesis of a compound containing a 2,4,6-triaryl-1,3,5-triazine structure along with a phenoxazine structure, a phenothiazine structure or a phenazine structure, and have first revealed that the compound is useful as a light-emitting material. It has been also found that a compound that is useful as a delayed fluorescent material is included in the compound, and have revealed that an organic light-emitting device having a high light emission efficiency may be provided inexpensively. Based on the knowledge, the inventors have consequently provide the invention below as a measure for solving the problems.

(1) A compound represented by the following general formula (1):

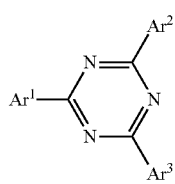

General Formula (1)

wherein in the general formula (1), $Ar^1$ to $Ar^3$ each independently represent a substituted or unsubstituted aryl group, provided that at least one thereof represents an aryl group substituted by a group represented by the following general formula (2):

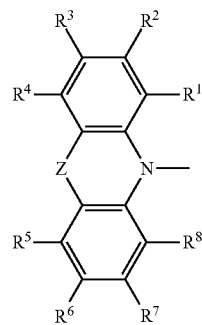

General Formula (2)

wherein in the general formula (2), $R^1$ to $R^8$ each independently represent a hydrogen atom or a substituent; Z represents O, S, O=C or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(2) The compound according to the item (1), wherein at least one of $Ar^1$ to $Ar^3$ in the general formula (1) represents an aryl group substituted by a group represented by the following general formula (3):

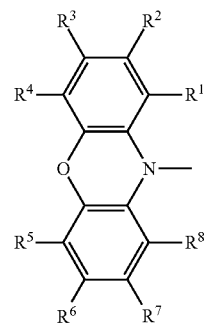

General Formula (3)

wherein in the general formula (3), $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(3) The compound according to the item (1), wherein at least one of $Ar^1$ to $Ar^3$ in the general formula (1) represents an aryl group substituted by a group represented by the following general formula (4):

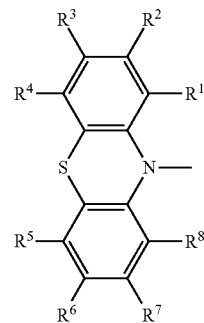

General Formula (4)

wherein in the general formula (4), $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(4) The compound according to the item (1), wherein at least one of $Ar^1$ to $Ar^3$ in the general formula (1) represents an aryl group substituted by a group represented by the following general formula (5):

General Formula (5)

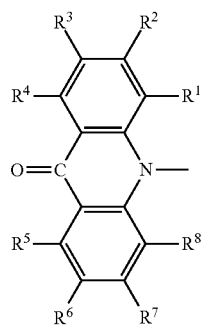

wherein in the general formula (5), $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(5) The compound according to the item (1), wherein the compound has a structure represented by the following general formula (6):

General Formula (6)

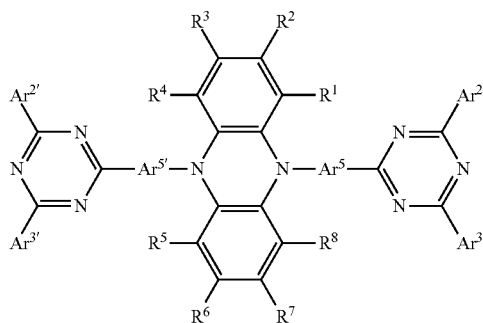

wherein in the general formula (6), $Ar^2$, $Ar^3$, $Ar^{2'}$ and $Ar^{3'}$ each independently represent a substituted or unsubstituted aryl group; $Ar^5$ and $Ar^{5'}$ each independently represent a substituted or unsubstituted arylene group; and $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(6) The compound according to the item (1), wherein the compound has a structure represented by the following general formula (7):

General Formula (7)

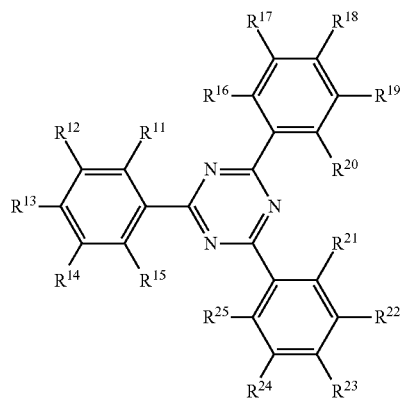

wherein in the general formula (7), at least one of $R^{11}$ to $R^{25}$ represents a group represented by the general formula (2), and the other thereof each independently represent a hydrogen atom or a substituent other than the general formula (2), provided that $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, and $R^{24}$ and $R^{25}$ each may be bonded to each other to form a cyclic structure.

(7) The compound according to the item (6), wherein at least one of $R^{11}$ to $R^{25}$ in the general formula (7) represents a group represented by the general formula (3).

(8) The compound according to the item (6), wherein at least one of $R^{11}$ to $R^{25}$ in the general formula (7) represents a group represented by the general formula (4).

(9) The compound according to the item (6), wherein at least one of $R^{11}$ to $R^{25}$ in the general formula (7) represents a group represented by the general formula (5).

(10) The compound according to any one of items (7) to (9), wherein the compound has a rotationally symmetric structure with the center of the triazine ring as the axis.

(11) The compound according to the item (6), wherein the compound has a structure represented by the following general formula (8):

General Formula (8)

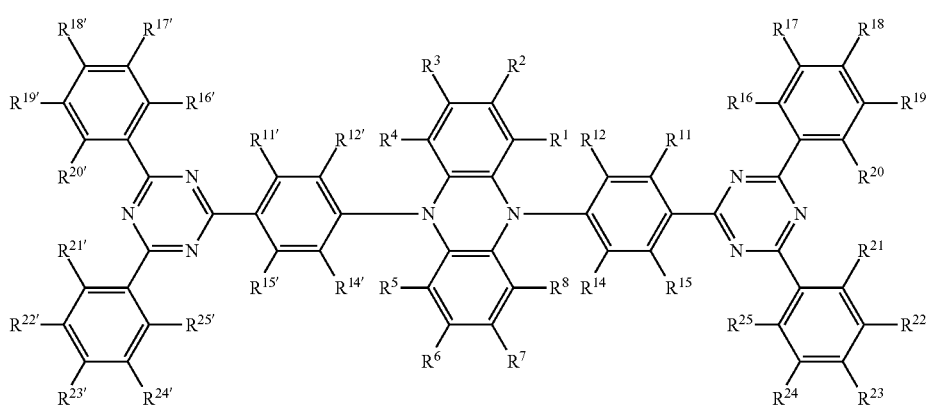

wherein in the general formula (8), $R^1$ to $R^8$, $R^{11}$, $R^{12}$, $R^{14}$ to $R^{25}$, $R^{11'}$, $R^{12'}$, and $R^{14'}$ to $R^{25'}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{11'}$ and $R^{12'}$, and $R^{14'}$ and $R^{14'}$, $R^{16'}$ and $R^{17'}$, $R^{17'}$ and $R^{18'}$, $R^{18'}$ and $R^{19'}$, $R^{19'}$ and $R^{20'}$, $R^{21'}$ and $R^{22'}$, $R^{22'}$ and $R^{23'}$, $R^{23'}$ and $R^{24'}$, and $R^{24'}$ and $R^{25'}$ each may be bonded to each other to form a cyclic structure.

(12) A light-emitting material containing the compound according to any one of items (1) to (11).

(13) A delayed fluorescent emitter having a structure represented by the general formula (1).

(14) An organic light-emitting device containing a substrate having thereon a light-emitting layer that contains the light-emitting material according to the item (12).

(15) The organic light-emitting device according to the item (14), wherein the device emits delayed fluorescent light.

(16) The organic light-emitting device according to the item (14) or (15), wherein the device is an organic electroluminescent device.

Advantageous Effects of Invention

The compound of the invention is useful as a light-emitting material. The compound of the invention includes a compound that emits delayed fluorescent light. An organic light-emitting device using the compound of the invention as a light-emitting material may achieve a high light emission efficiency.

DESCRIPTION OF EMBODIMENTS

Figure 1:
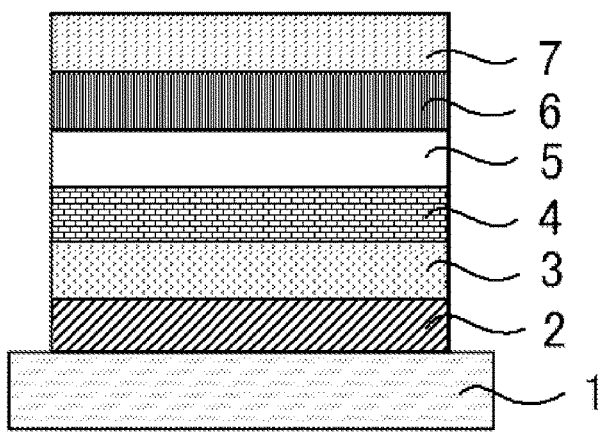
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the present specification, a numerical range expressed by "from X to Y" means a range including the numerals X and Y as the lower limit and the upper limit, respectively.

Compound Represented by General Formula (1)

The compound of the invention has a structure represented by the following general formula (1):

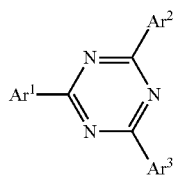

General Formula (1)

wherein in the general formula (1), $Ar^1$ to $Ar^3$ each independently represent a substituted or unsubstituted aryl group, provided that at least one thereof represents an aryl group substituted by a group represented by the following general formula (2):

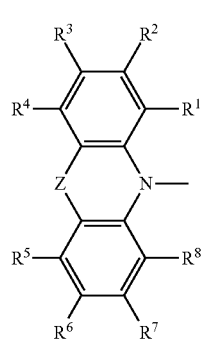

General Formula (2)

wherein in the general formula (2), $R^1$ to $R^8$ each independently represent a hydrogen atom or a substituent; Z represents O, S, O=C or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

The aromatic ring constituting the aryl group represented by $Ar^1$ to $Ar^3$ of the general formula (1) may be a monocyclic ring or a fused ring, and specific examples thereof include a benzene ring, a naphthalene ring, an anthracene ring and a phenanthrene ring. The aryl group preferably has from 6 to 40 carbon atoms, more preferably from 6 to 20 carbon atoms, and further preferably from 6 to 14 carbon atoms. At least one of $Ar^1$ to $Ar^3$ is an aryl group substituted by a group represented by the general formula (2). Two of $Ar^1$ to $Ar^3$ each may be an aryl group substituted by a group represented by the general formula (2), and all three of $Ar^1$ to $Ar^3$ each may be an aryl group substituted by a group represented by the general formula (2). One of the aryl group may be substituted by two or more groups substituted by a group represented by the general formula (2). For the descriptions for the groups that are capable of being substituted on the aryl group represented by $Ar^1$ to $Ar^3$ and the preferred ranges thereof, the descriptions for the substituents capable of being on $R^1$ to $R^8$ and the preferred ranges thereof described later may be referenced.

$R^1$ to $R^8$ in the general formula (2) each independently represent a hydrogen atom or a substituent. All $R^1$ to $R^8$ each may be a hydrogen atom. In the case where two or more thereof each are a substituent, the substituents may be the same as or different from each other. Examples of the substituent include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an aryl-substituted amino group having from 12 to 40 carbon atoms, an acyl group having from 2 to 20 carbon atoms, an aryl group having from 6 to 40 carbon atoms, a heteroaryl group having from 3 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms and a nitro group. Among these specific examples, the groups that may be further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted dialkylamino group having from 1 to 10 carbon atoms, a substituted or unsubstituted diarylamino group having from 12 to 40 carbon atoms and a substituted or unsubstituted carbazolyl group having from 12 to 40 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted diarylamino group having from 12 to 40 carbon atoms, a substituted or unsubstituted aryl group having from 6 to 15 carbon atoms and a substituted or unsubstituted heteroaryl group having from 3 to 12 carbon atoms.

The alkyl group referred herein may be any one of linear, branched and cyclic groups, and more preferably has from 1 to 6 carbon atoms, and specific examples thereof include a methyl group, an ethyl group, a propyl group, a butyl group, a tert-butyl group, a pentyl group, a hexyl group and an isopropyl group. The aryl group may be a monocyclic ring or a fused ring, and specific examples thereof include a phenyl group and a naphthyl group. The alkoxy group may be any one of linear, branched and cyclic groups, and more preferably has from 1 to 6 carbon atoms, and specific examples thereof include a methoxy group, an ethoxy group, a propoxy group, a butoxy group, a tert-butoxy group, a pentyloxy group, a hexyloxy group and isopropoxy group. The two alkyl groups of the dialkylamino group may be the same as or different from each other, and are preferably the same as each other. The two alkyl groups of the dialkylamino group each independently may be any one of linear, branched and cyclic groups, and more preferably has from 1 to 6 carbon atoms, and specific examples thereof include a methyl group, an ethyl group, a propyl group, a butyl group, a pentyl group, a hexyl group and an isopropyl group. The two alkyl groups of the dialkylamino group may be bonded to each other to form a cyclic structure with the nitrogen atom of the amino group. The aryl group that may be used as the substituent may be a monocyclic ring or a fused ring, and specific examples thereof include a phenyl group and a naphthyl group. The heteroaryl group may also be a monocyclic ring or a fused ring, and specific examples thereof include a pyridyl group, a pyridazyl group, a pyrimidyl group, a triazyl group, a triazolyl group and a benzotriazolyl group. The heteroaryl group may be a group that is bonded through the heteroatom or a group that is bonded through the carbon atom constituting the heteroaryl ring. The two aryl group of the diarylamino group each may be a monocyclic ring or a fused ring, and specific examples thereof include a phenyl group and a naphthyl group. The two aryl groups of the diarylamino group may be bonded to each other to form a cyclic structure with the nitrogen atom of the amino group, and specific examples thereof include a 9-carbazolyl group.

In the general formula (2), $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure. The cyclic structure may be an aromatic ring or an aliphatic ring, and may be one containing a hetero atom. The hetero atom herein is preferably selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring and a cycloheptaene ring.

In the general formula (2), Z represents O, S, O=C or $Ar^4$—N, in which $Ar^4$ represents a substituted or unsubstituted aryl group. The aromatic ring constituting the aryl group represented by $Ar^4$ may be a monocyclic ring or a fused ring, and specific examples thereof include a benzene ring, a naphthalene ring, an anthracene ring and a phenanthrene ring. The aryl group preferably has from 6 to 40 carbon atoms, and more preferably from 6 to 20 carbon atoms. For the descriptions for the groups that are capable of being substituted on the aryl group represented by $Ar^4$ and the preferred ranges thereof, the descriptions for the substituents capable of being on $R^1$ to $R^8$ and the preferred ranges thereof described above may be referenced.

The group represented by the general formula (2) is preferably a group having a structure represented by the general formula (3), a group having a structure represented by the general formula (4) or a group having a structure represented by the general formula (5).

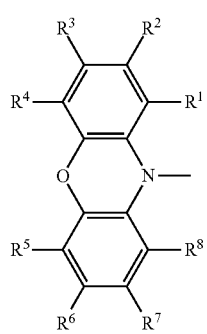

General Formula (3)

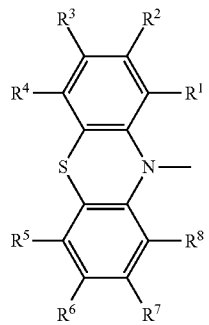

General Formula (4)

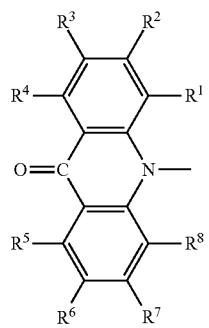

General Formula (5)

In the general formulae (3) to (5), $R^1$ to $R^8$ each independently represent a hydrogen atom or a substituent. For the description for $R^1$ to $R^8$ and the preferred ranges thereof, the corresponding descriptions in the general formula (2) may be referenced. $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

In the case where Z in the general formula (2) is $Ar^4$—N, the compound represented by the general formula (1) may encompass a structure represented by the general formula (6):

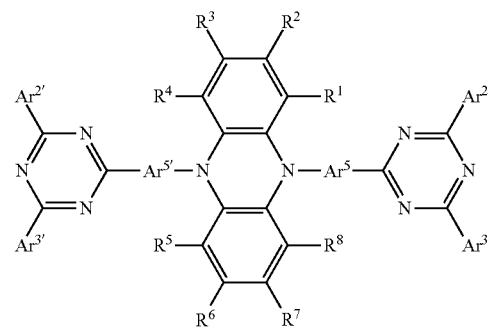

General Formula (6)

In the general formula (6), $Ar^2$, $Ar^3$, $Ar^{2'}$ and $Ar^{3'}$ each independently represent a substituted or unsubstituted aryl group; $Ar^5$ and $Ar^{5'}$ each independently represent a substituted or unsubstituted arylene group; and $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

For the descriptions for $Ar^2$, $Ar^3$, $Ar^{2'}$ and $Ar^{3'}$ in the general formula (6) and the preferred ranges thereof, the descriptions for $Ar^1$ to $Ar^3$ in the general formula (1) and the preferred ranges thereof may be referenced. The aromatic ring constituting the arylene group capable of being represented by $Ar^5$ and $Ar^{5'}$ in the general formula (6) may be a monocyclic ring or a fused ring, and specific examples thereof include a benzene ring, a naphthalene ring, an anthracene ring and a phenanthrene ring. The arylene group preferably has from 6 to 40 carbon atoms, more preferably from 6 to 20 carbon atoms, and further preferably from 6 to 14 carbon atoms. For the descriptions for $R^1$ to $R^8$ in the general formula (6) and the preferred ranges thereof, the descriptions for $R^1$ to $R^8$ in the general formula (2) and the preferred ranges thereof may be referenced.

In the compounds represented by the general formula (6), a compound, in which $Ar^2$ and $Ar^{2'}$ are the same as each other, $Ar^3$ and $Ar^{3'}$ are the same as each other, and $Ar^5$ and $Ar^{5'}$ are the same as each other, has an advantage that the compound may be easily synthesized.

The compound represented by the general formula (1) preferably has a structure represented by the following general formula (7):

General Formula (7)

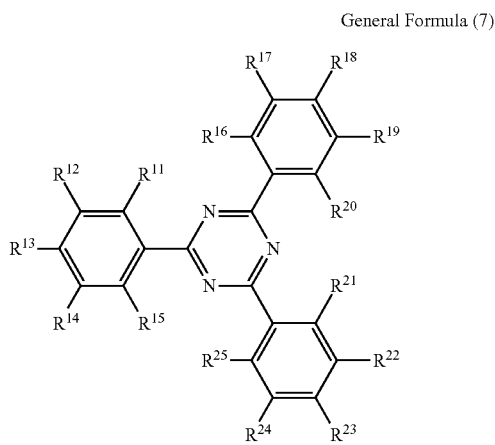

In the general formula (7), at least one of $R^{11}$ to $R^{25}$ represents a group represented by the general formula (2), and the other thereof each independently represent a hydrogen atom or a substituent other than the general formula (2).

In the general formula (7), at least one of $R^{11}$ to $R^{25}$ represents a group represented by the general formula (2), and the number of the group represented by the general formula (2) substituted is preferably from 1 to 9, and more preferably from 1 to 6, among $R^{11}$ to $R^{25}$. For example, the number may be selected from a range of from 1 to 3. The groups represented by the general formula (2) may be bonded to each of the three benzene rings constituting the 1,3,5-triazine ring, or may be bonded to only one or only two thereof. It is preferred that the three benzene rings each have from 0 to 3 groups represented by the general formula (2), and it is more preferred that the three benzene rings each have from 0 to 2 groups represented by the general formula (2). For example, such a case that the three benzene rings each have 0 or 1 group represented by the general formula (2) may be selected.

The substitution position of the group represented by the general formula (2) may be any of $R^{11}$ to $R^{25}$, and is preferably selected from $R^{12}$ to $R^{14}$, $R^{17}$ to $R^{18}$, and $R^{22}$ to $R^{24}$. Examples thereof include a case where from 0 to 2 of $R^{12}$ to $R^{14}$, from 0 to 2 of $R^{17}$ to $R^{18}$ and from 0 to 2 of $R^{22}$ to $R^{24}$ are the groups represented by the general formula (2), and a case where 0 or 1 of $R^{12}$ to $R^{14}$, 0 or 1 of $R^{17}$ to $R^{18}$ and 0 or 1 of $R^{22}$ to $R^{24}$ are the groups represented by the general formula (2).

In the case where one of $R^{11}$ to $R^{25}$ is substituted by the group represented by the general formula (2), the substitution position thereof is preferably $R^{12}$ or $R^{13}$. In the case where two of $R^{11}$ to $R^{25}$ are substituted by the groups represented by the general formula (2), the substitution positions thereof are preferably $R^{12}$ and $R^{14}$, or any one of $R^{12}$ and $R^{13}$ and any one of $R^{17}$ and $R^{18}$. In the case where three of $R^{11}$ to $R^{25}$ are substituted by the groups represented by the general formula (2), the substitution positions thereof are preferably $R^{12}$, $R^{14}$ and any one of $R^{17}$ and $R^{18}$, or any one of $R^{12}$ and $R^{13}$, any one of $R^{17}$ and $R^{18}$, and any one of $R^{22}$ and $R^{23}$.

$R^{11}$ to $R^{25}$ that are not the group represented by the general formula (2) each independently represent a hydrogen atom or a substituent other than the general formula (2). All of them may be hydrogen atoms. In the case where two or more thereof are each a substituent, the substituents may be the same as or different from each other. For the descriptions for the substituents capable of being represented by $R^{11}$ to $R^{25}$ and the preferred ranges thereof, the descriptions for the substituents capable of being represented by $R^1$ to $R^8$ and the preferred ranges thereof described above may be referenced.

In the general formula (7), $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, and $R^{24}$ and $R^{25}$ each may be bonded to each other to form a cyclic structure. For the descriptions for the cyclic structure and the preferred ranges thereof, the corresponding descriptions in the general formula (2) may be referenced.

The group represented by the general formula (2) contained in the general formula (7) is preferably a group having a structure represented by the general formula (3), a group having a structure represented by the general formula (4) or a group having a structure represented by the general formula (5).

The compound represented by the general formula (7) preferably has a symmetric molecular structure. For example, the compound preferably has a rotationally symmetric structure with the center of the triazine ring as the axis. In this case, in the general formula (7), $R^{11}$, $R^{16}$ and $R^{21}$ are the same as each other, $R^{12}$, $R^{17}$ and $R^{22}$ are the same as each other, $R^{13}$, $R^{18}$ and $R^{23}$ are the same as each other, $R^{14}$, $R^{19}$ and $R^{24}$ are the same as each other, and $R^{15}$, $R^{20}$ and $R^{25}$ are the same as each other. Examples thereof include a case where $R^{13}$, $R^{18}$ and $R^{23}$ each are the group represented by the general formula (2), and the others each are a hydrogen atom.

In the case where Z in the general formula (2) is $Ar^4$—N, the compound represented by the general formula (7) may encompass a structure represented by the general formula (8):

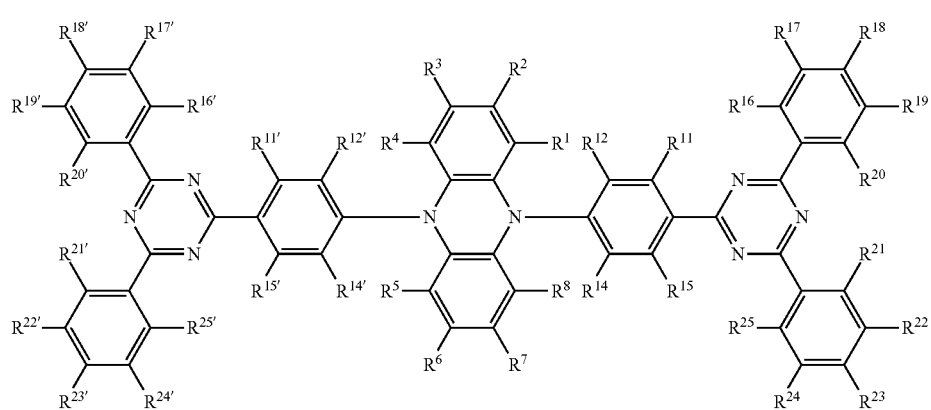

General Formula (8)

In the general formula (8), $R^1$ to $R^8$, $R^{11}$, $R^{12}$, $R^{14}$ to $R^{25}$, $R^{11'}$, $R^{12'}$, and $R^{14'}$ to $R^{25'}$ each independently represent a hydrogen atom or a substituent. For the descriptions for $R^1$ to $R^8$ in the general formula (8) and the preferred ranges thereof, the descriptions for $R^1$ to $R^8$ in the general formula (2) and the preferred ranges thereof may be referenced. For the descriptions for $R^{11}$, $R^{12}$, $R^{14}$ to $R^{25}$, $R^{11'}$, $R^{12'}$, and $R^{14'}$ to $R^{25'}$ in the general formula (8) and the preferred ranges thereof, the descriptions for $R^{11}$ to $R^{25}$ in the general formula (7) and the preferred ranges thereof may be referenced. In the general formula (8), $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{11'}$ and $R^{12'}$, $R^{14'}$ and $R^{15'}$, $R^{16'}$ and $R^{17'}$, $R^{17'}$ and $R^{18'}$, $R^{18'}$ and $R^{19'}$, $R^{19'}$ and $R^{20'}$, $R^{21'}$ and $R^{22'}$, $R^{22'}$ and $R^{23'}$, $R^{23'}$ and $R^{24'}$ and $R^{24'}$ and $R^{25'}$ each may be bonded to each other to form a cyclic structure. For the descriptions for the cyclic structure and the preferred ranges thereof, the corresponding descriptions in the general formula (2) may be referenced.

Specific examples of the compound represented by the general formula (1) are shown below. However, the compound represented by the general formula (1) capable of being used in the invention is not construed as being limited to the specific examples.

Compound 1

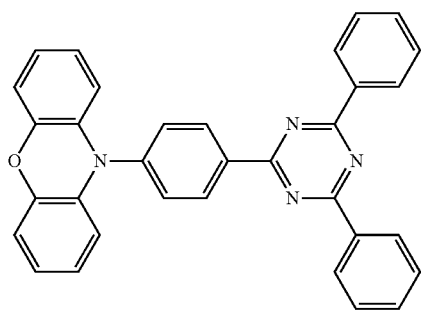

-continued

Compound 2

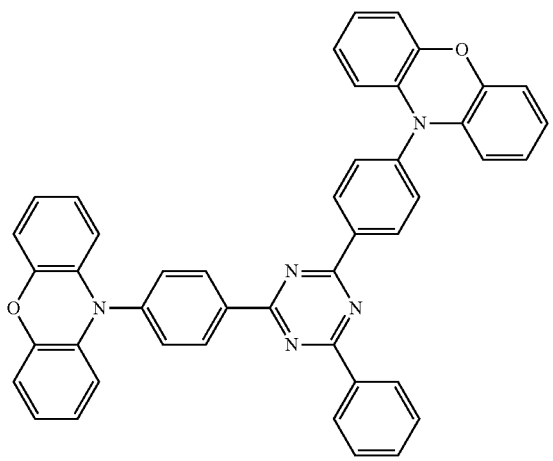

Compound 3

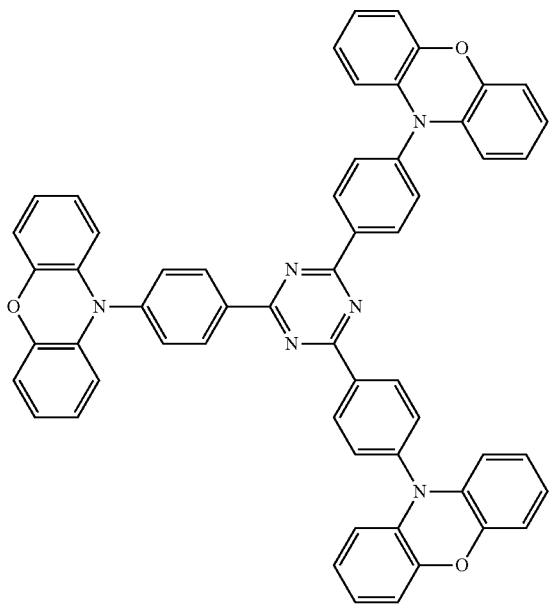

-continued
Compound 4
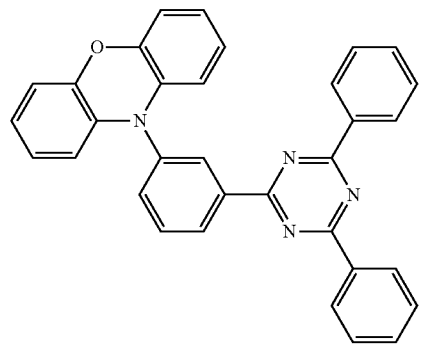
Compound 5
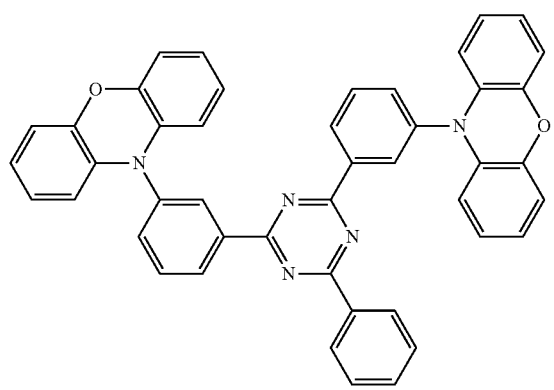
Compound 6
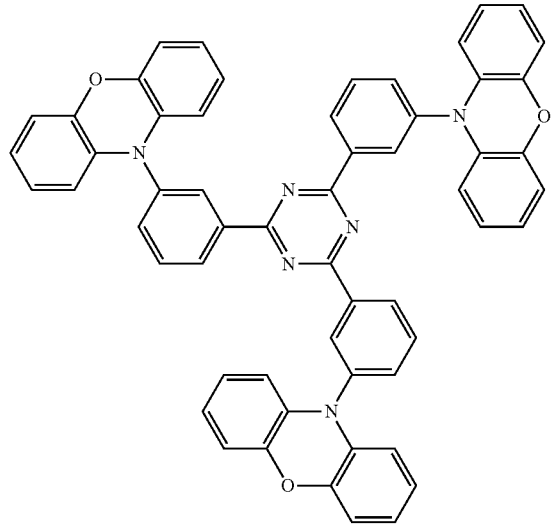
Compound 7
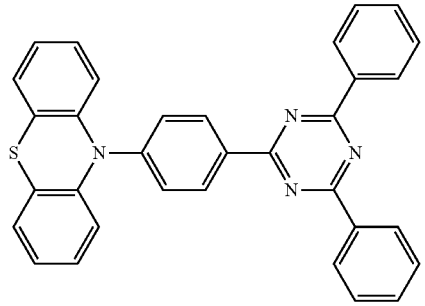
-continued
Compound 8
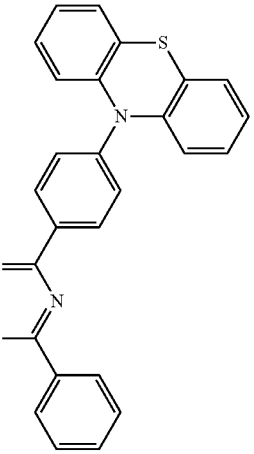
Compound 9
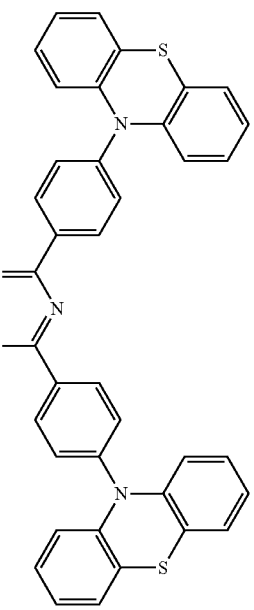
Compound 10
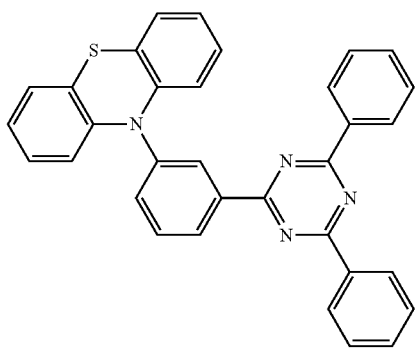

Compound 11
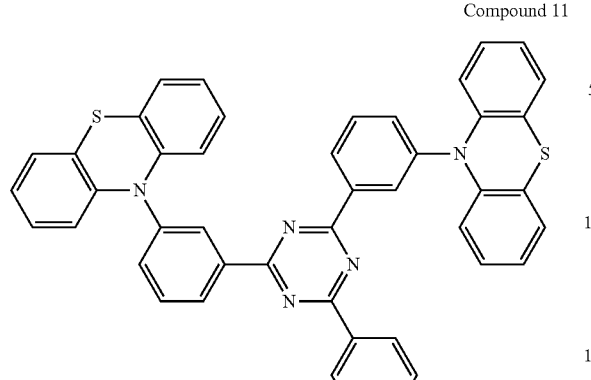
Compound 12
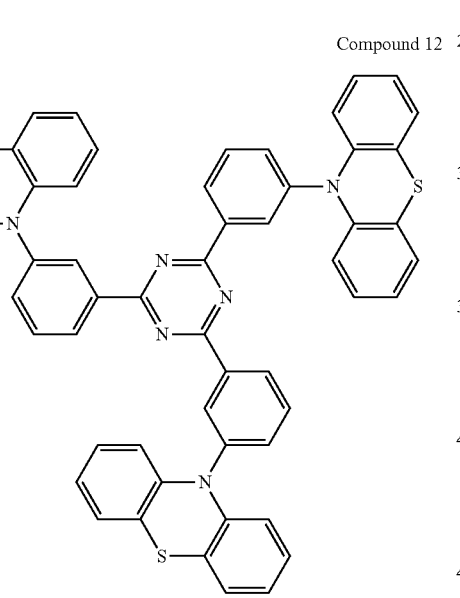
Compound 13
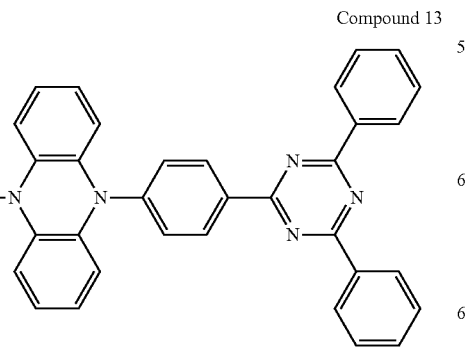
Compound 14
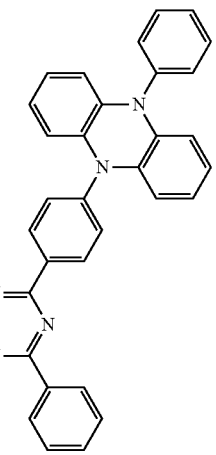
Compound 15
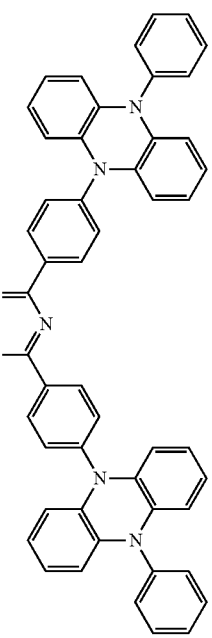
Compound 16
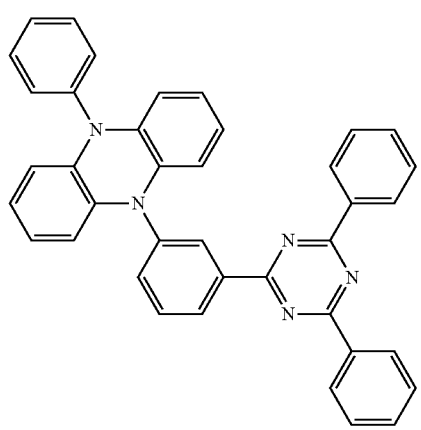

Compound 17
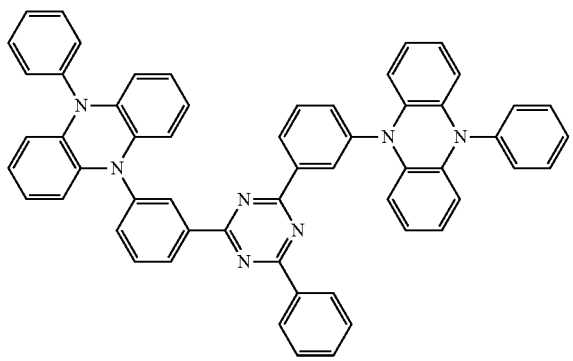
Compound 18
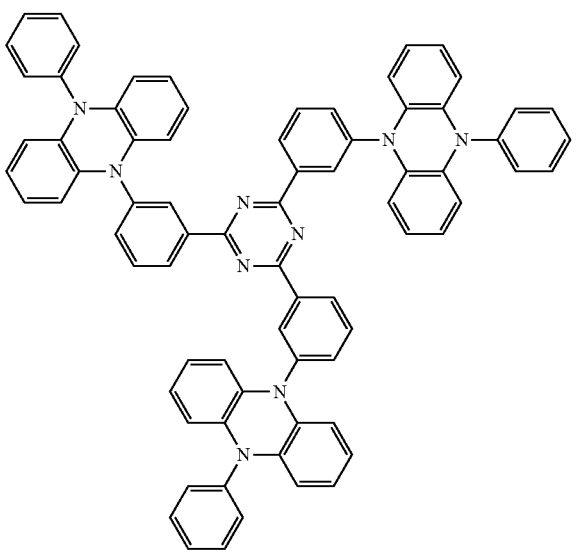
Compound 19
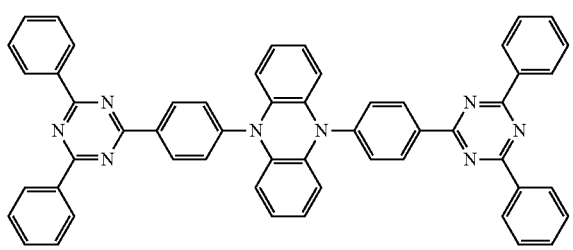
Compound 20
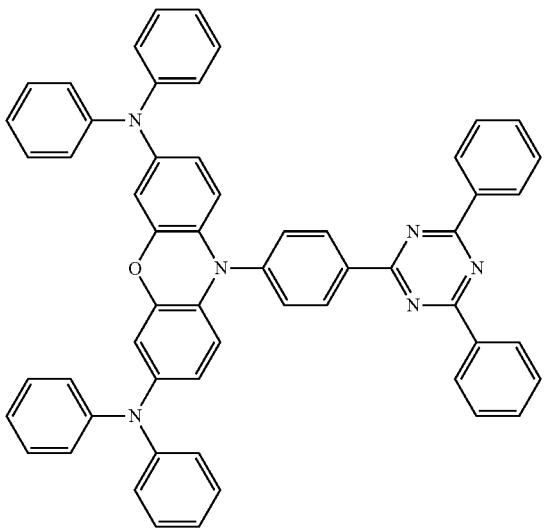
Compound 21
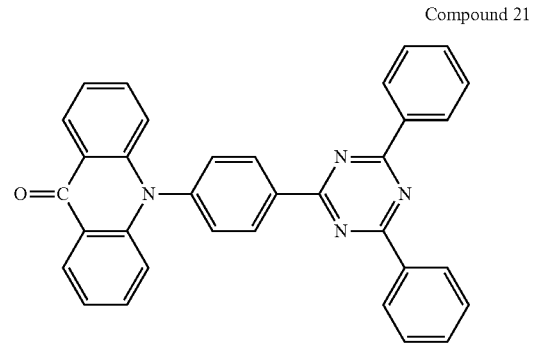
Compound 22
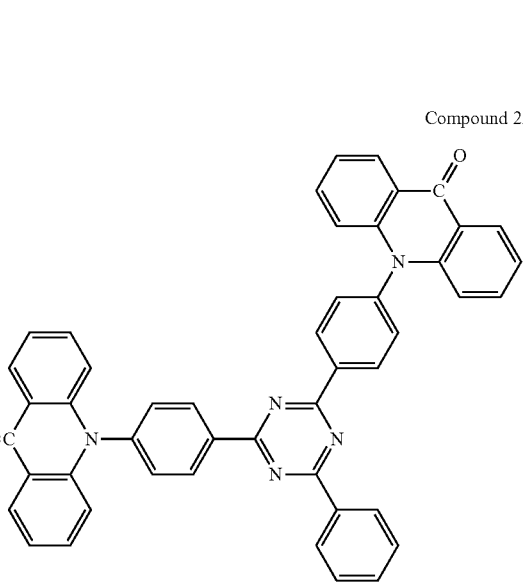

Compound 23

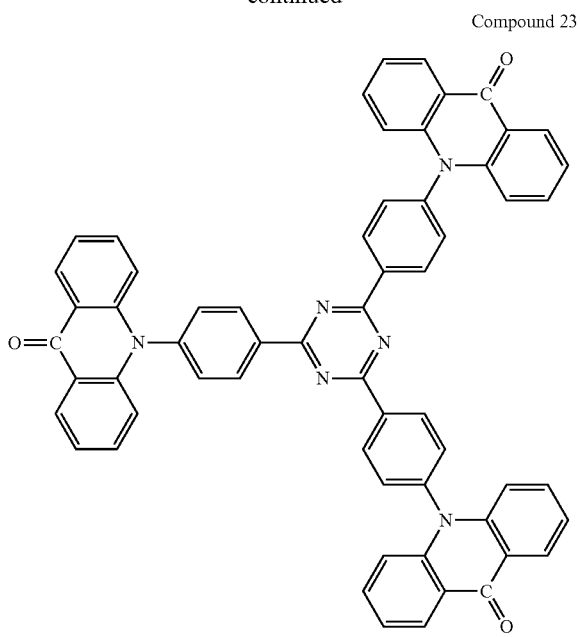

Compound 24

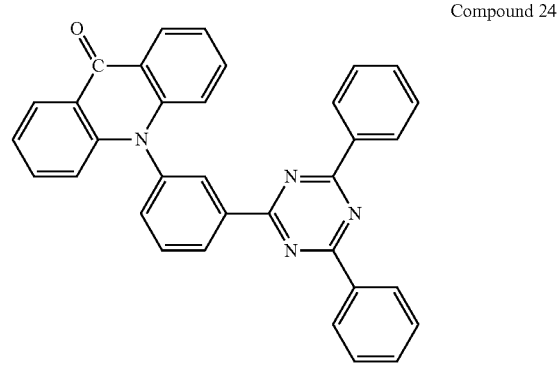

Compound 25

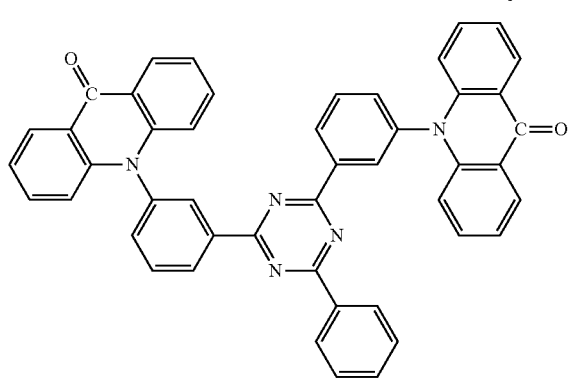

Compound 26

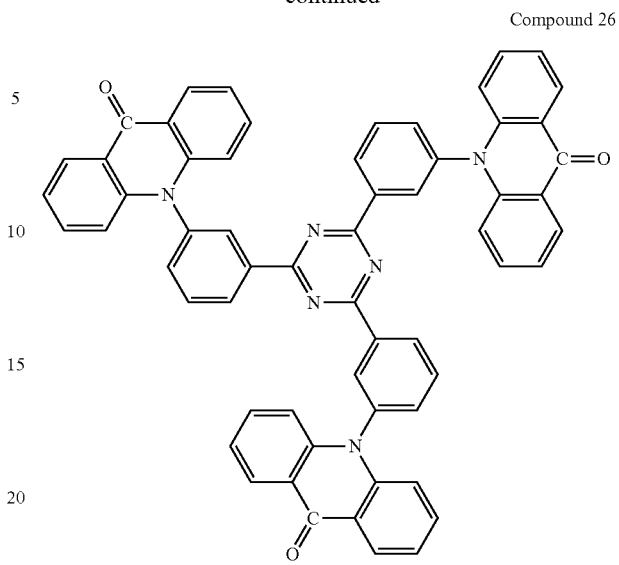

The molecular weight of the compound represented by the general formula (1) is preferably 1,500 or less, more preferably 1,200 or less, further preferably 1,000 or less, and still further preferably 800 or less, in the case where it is intended that an organic layer containing the compound represented by the general formula (1) is utilized by forming by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

In an application embodiment of the invention, a compound that contains plural structures each represented by the general formula (1) in the molecule thereof may be used as a light-emitting material.

For example, it is considered that a polymerizable group may be contained in advance in the structure represented by the general formula (1), and a polymer obtained by polymerizing the polymerizable group may be used as a light-emitting material. Specifically, it is considered that a monomer that contains a polymerizable functional group in one of $Ar^1$ to $Ar^3$ may be prepared, and may be homopolymerized or copolymerized with another monomer to prepare a polymer having repeating units, and the polymer may be used as a light-emitting material. In alternative, it is also considered that the compounds each having the structure represented by the general formula (1) may be coupled to provide a dimer or a trimer, which may be used as a light-emitting material.

Examples of the polymer having a repeating unit containing the structure represented by the general formula (1) include a polymer containing a structure represented by the following general formula (9) or (10):

General Formula (9)

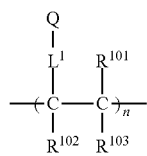

General Formula (10)

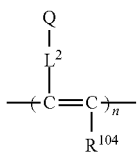

In the general formulae (9) and (10), Q represents a group containing the structure represented by the general formula (1), and L¹ and L² each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably represents an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking groups represented by L1 and L2 each are bonded to any one of $Ar^1$ to $Ar^3$ of the structure represented by the general formula (1) constituting the group represented by Q. Two or more of the linking groups may be bonded to one group represented by Q to form a crosslinked structure or a network structure.

Specific examples of the structure of the repeating unit include structures represented by the following formulae (11) to (14):

Formula (11)

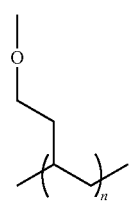

Formula (12)

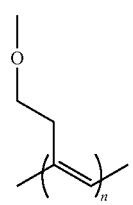

Formula (13)

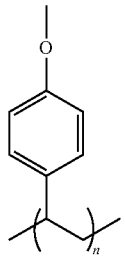

Formula (14)

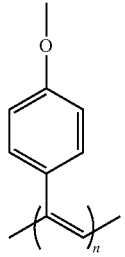

A polymer having a repeating unit containing a structure represented by the general formulae (11) to (14) may be synthesized in such a manner that a hydroxyl group is introduced as at least one of the substituents of $Ar^1$ to $Ar^3$ in the general formula (1), and the following compound is reacted with the hydroxyl group as a linker to introduce a polymerizable group, which is the polymerized.

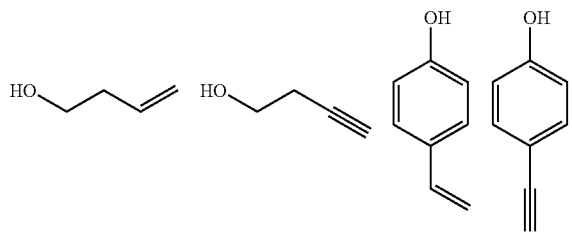

The polymer containing the structure represented by the general formula (1) in the molecule thereof may be a polymer that contains only a repeating unit having the structure represented by the general formula (1) or may be a polymer that contains another repeating unit in combination. One kind or two or more kinds of the repeating unit having the structure represented by the general formula (1) may be contained in the polymer. Examples of the repeating unit that does not have the structure represented by the general formula (1) include those derived from monomers that are used for ordinary copolymerization, and specific examples thereof include repeating units derived from monomers having an ethylenic unsaturated bond, such as ethylene and styrene.

Synthesis Method of Compound Represented by General Formula (1)

The compound represented by the general formula (1) may be synthesized by a combination of known reactions. For example, the synthesis in the case where $Ar^1$ in the general formula (1) is an aryl group substituted by the group represented by the general formula (2) may be performed by coupling a compound represented by the following general formula (15) and a compound represented by the following general formula (16) according the following scheme. The coupling reaction itself is a known reaction, and known reaction conditions may be appropriately selected. The compound represented by the general formula (16) may be synthesized, for example, by a corresponding chloride is converted to an amine and then further converted to a bromide.

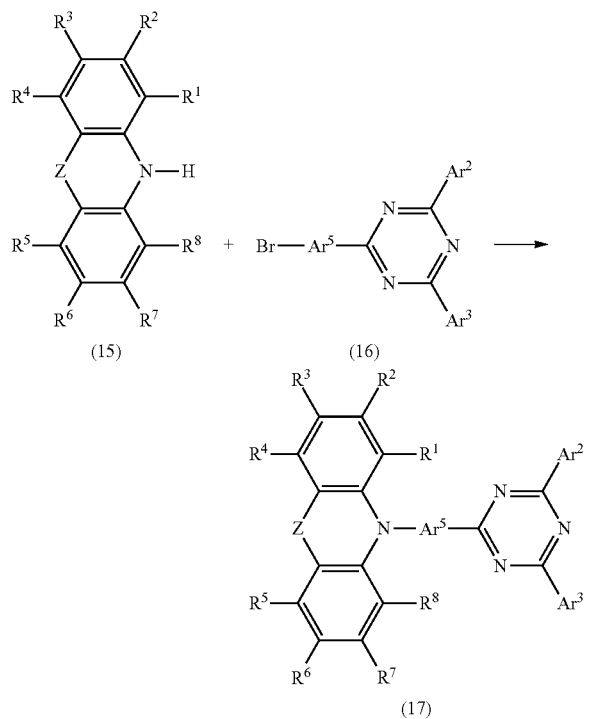

For the definitions for $R^1$ to $R^8$ and Z in the scheme, corresponding descriptions in the general formula (2) may be referenced. For the definitions for $Ar^2$, $Ar^3$ and $Ar^5$ in the scheme, corresponding descriptions in the general formula (6) may be referenced.

A compound having plural groups represented by the general formula (2) introduced thereto may be synthesized by changing the compound represented by the general formula (16) used in the scheme to a compound that is substituted with plural bromine atoms.

For the details of the reaction, synthesis examples described later may be referenced. The compound represented by the general formula (1) may be synthesized by a combination of other known reactions.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent material (delayed fluorescent emitter) emitting delayed fluorescent light. Accordingly, the invention also relates to a delayed fluorescent emitter having a structure represented by the general formula (1), use of a compound represented by the general formula (1) as a delayed fluorescent emitter, and a method for emitting delayed fluorescent light with a compound represented by the general formula (1). An organic light-emitting device that uses the compound as a light-emitting material thus has features that the device emits delayed fluorescent light and has a high light emission efficiency. The principle of the features may be described as follows for an organic electroluminescent device as an example.

In an organic electroluminescent device, carriers injected from an anode and a cathode form an excited state for the light-emitting material, from which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that excitons excited in the triplet state, which can be formed directly in that state or indirectly processes such as intersystem crossing from a singlet state, transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light after reverse intersystem crossing to the excited singlet state by absorbing the heat generated by the device. At this time, the light emitted after reverse intersystem crossing from the excited triplet state to the excited singlet state has the same wavelength as fluorescent light since it is light emission from the excited single state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited single state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of, as an electrode material, a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of, as an electrode material, a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. However, there are cases where a high light emission efficiency is obtained even though the singlet excitons and the triplet excitons may not be sufficiently confined, and therefore host materials capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer as the light-emitting material is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from diffusing outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The electron barrier layer or the exciton barrier layer referred herein means a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has lowest excited singlet energy and lowest excited triplet energy, at least one of which is higher than the lowest excited singlet energy and the lowest excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) may have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in layers other than the light-emitting layer. In this case, the compound represented by the general formula (1) used in the light-emitting layer and the compound represented by the general formula (1) used in the layers other than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R, R' and $R_1$ to $R_{10}$ each independently represent a hydrogen atom or a substituent; X represents a carbon atom or a heteroatom that forms a cyclic structure; n represents an integer of from 3 to 5; Y represents a substituent; and m represents an integer of 0 or more.

Preferred examples of a compound that may also be used as the host material of the light-emitting layer are shown below.

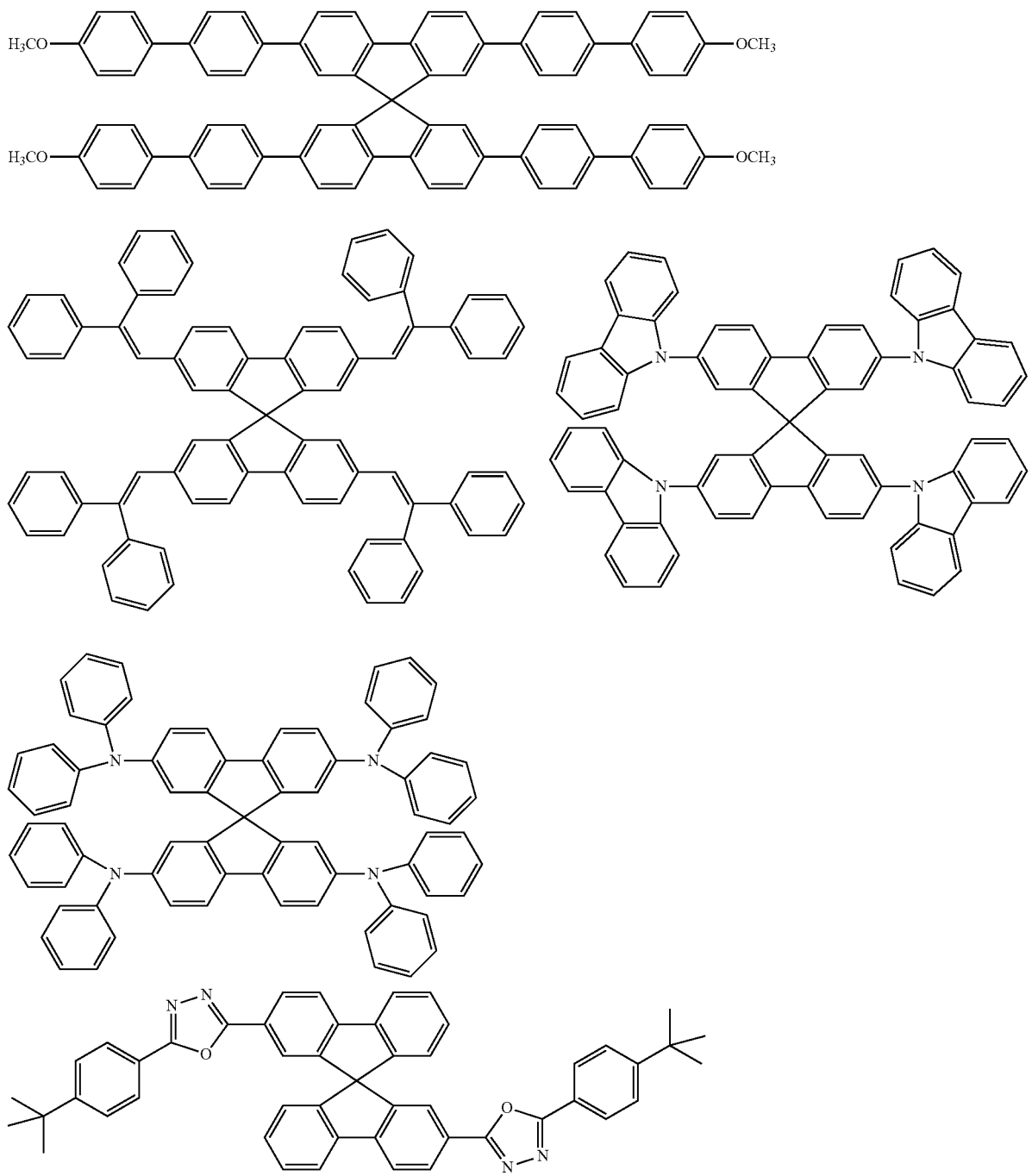

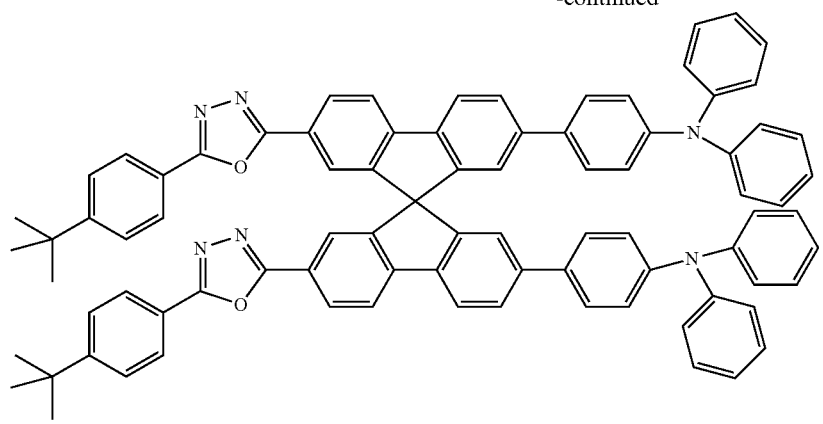
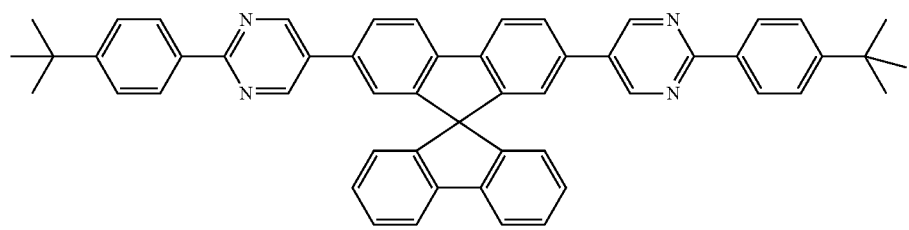
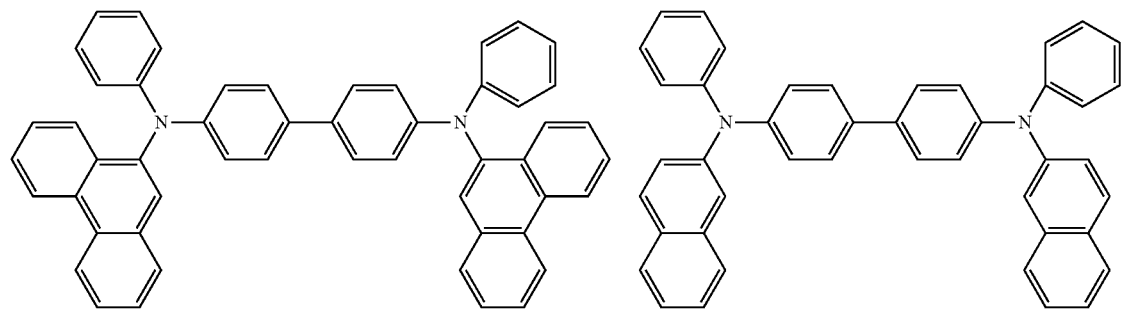
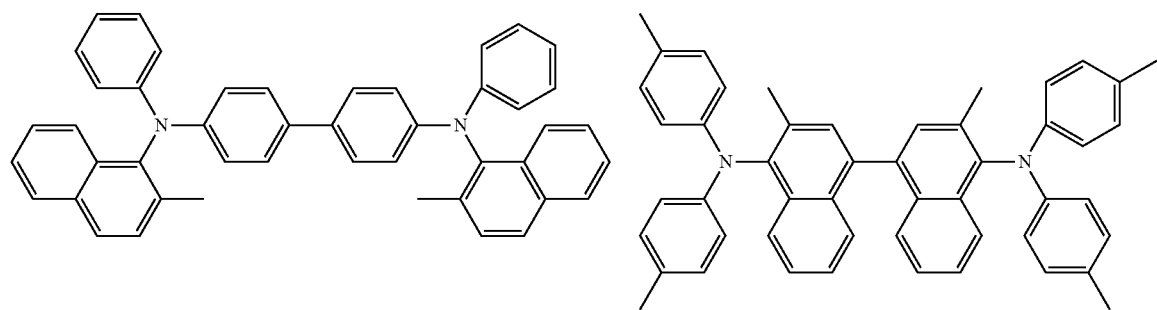

-continued
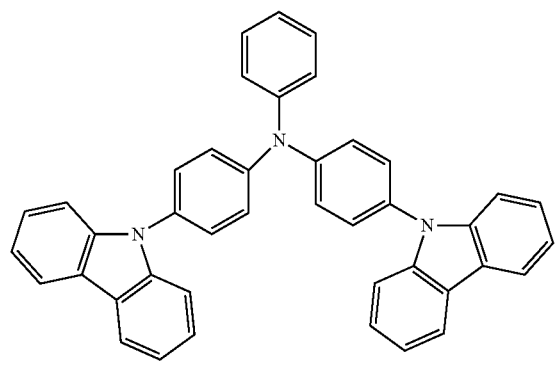
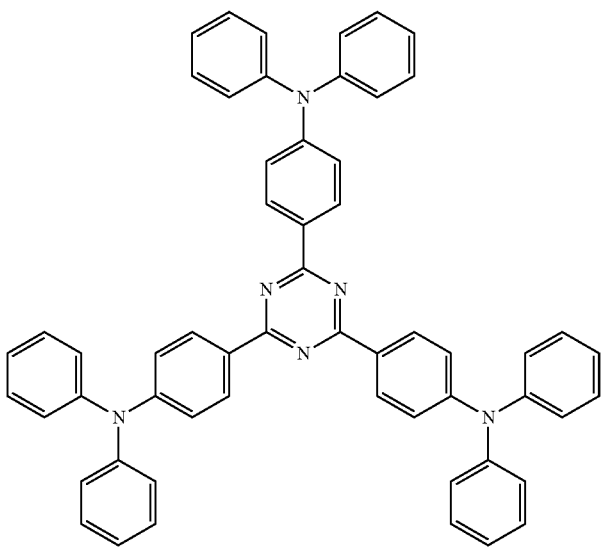
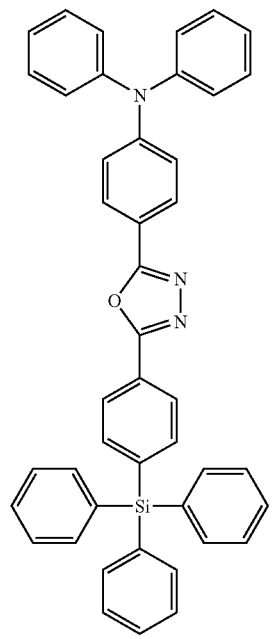
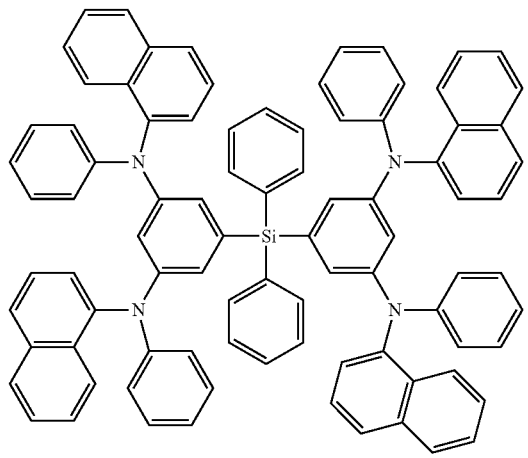
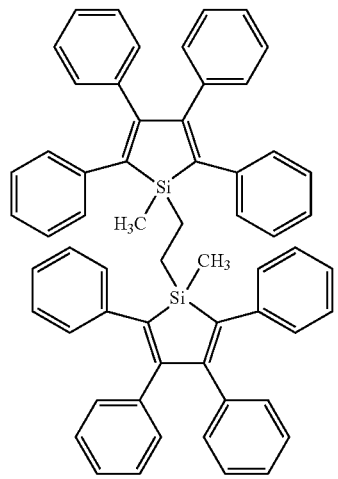
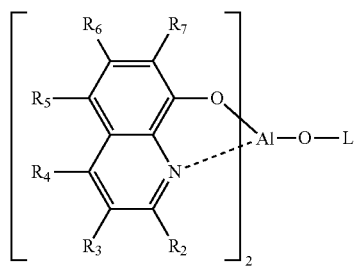
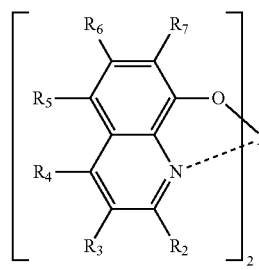
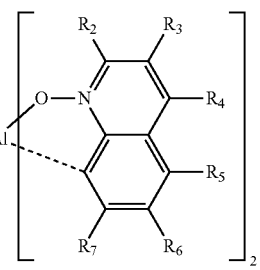
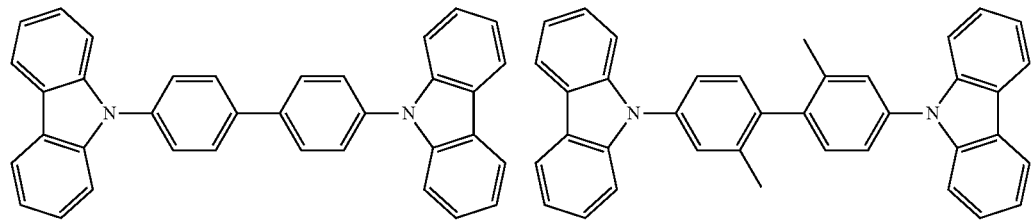

-continued
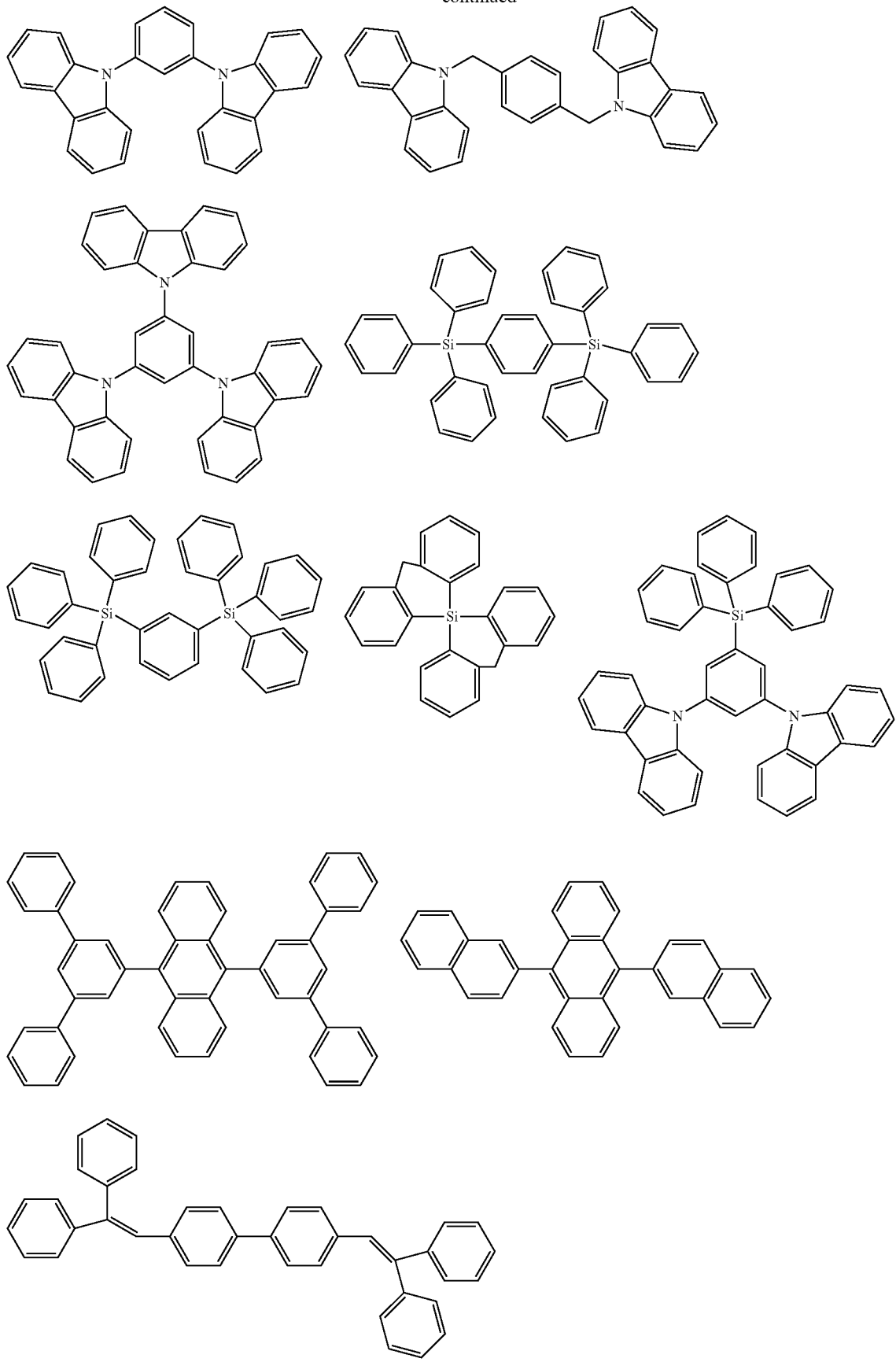

-continued
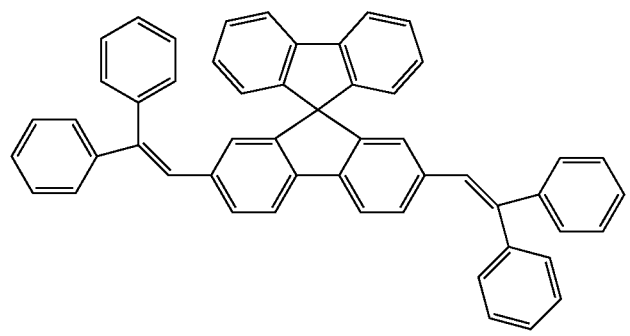
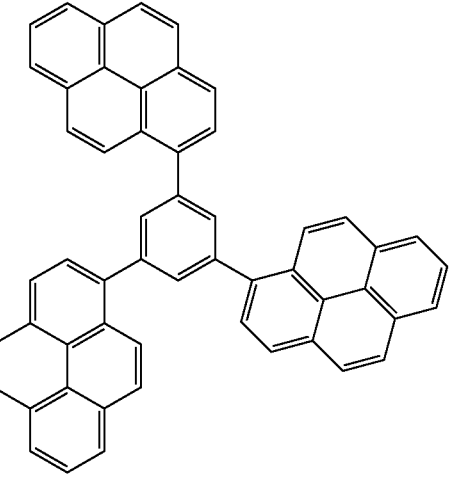
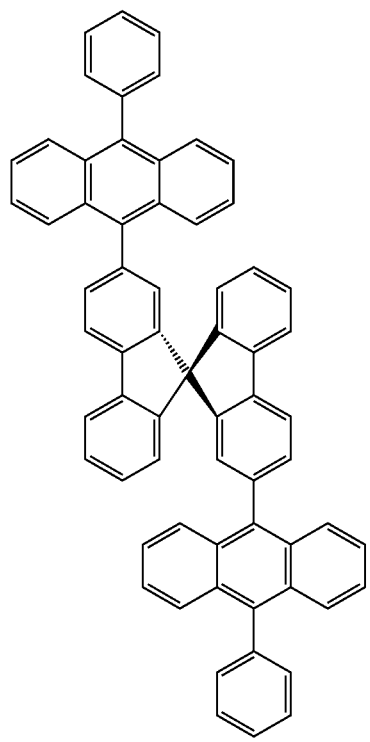
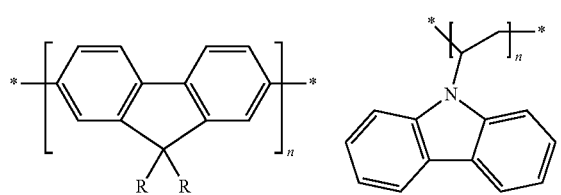
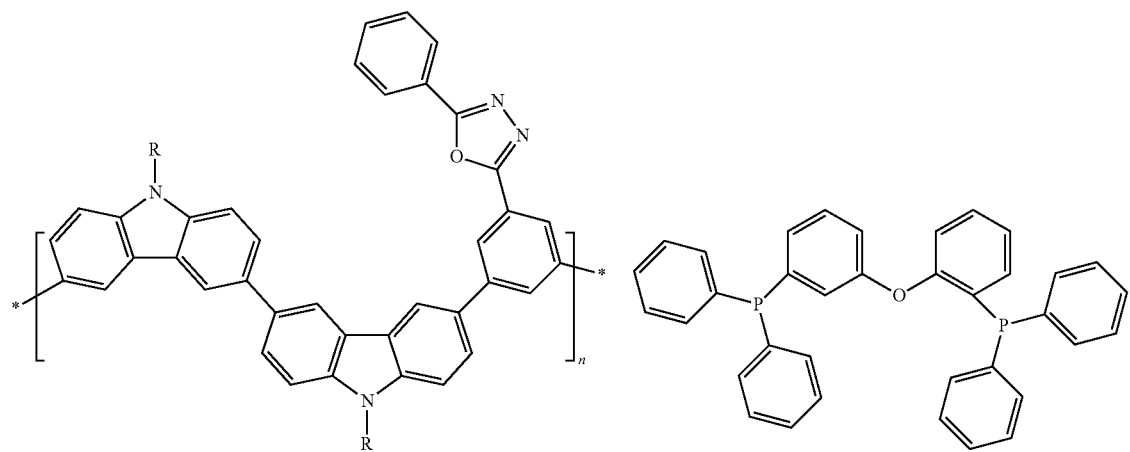

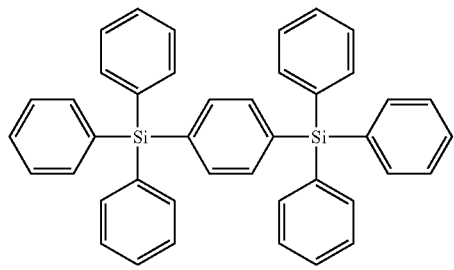
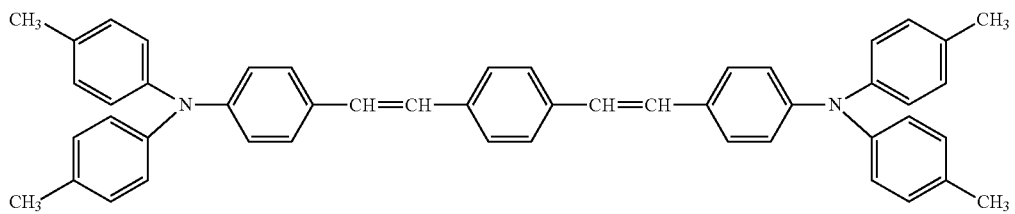
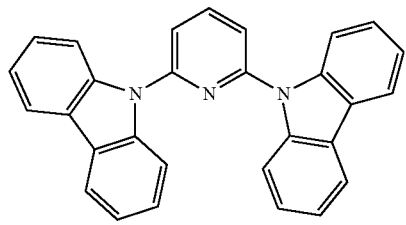
Preferred examples of a compound that may be used as the hole injection material are shown below.
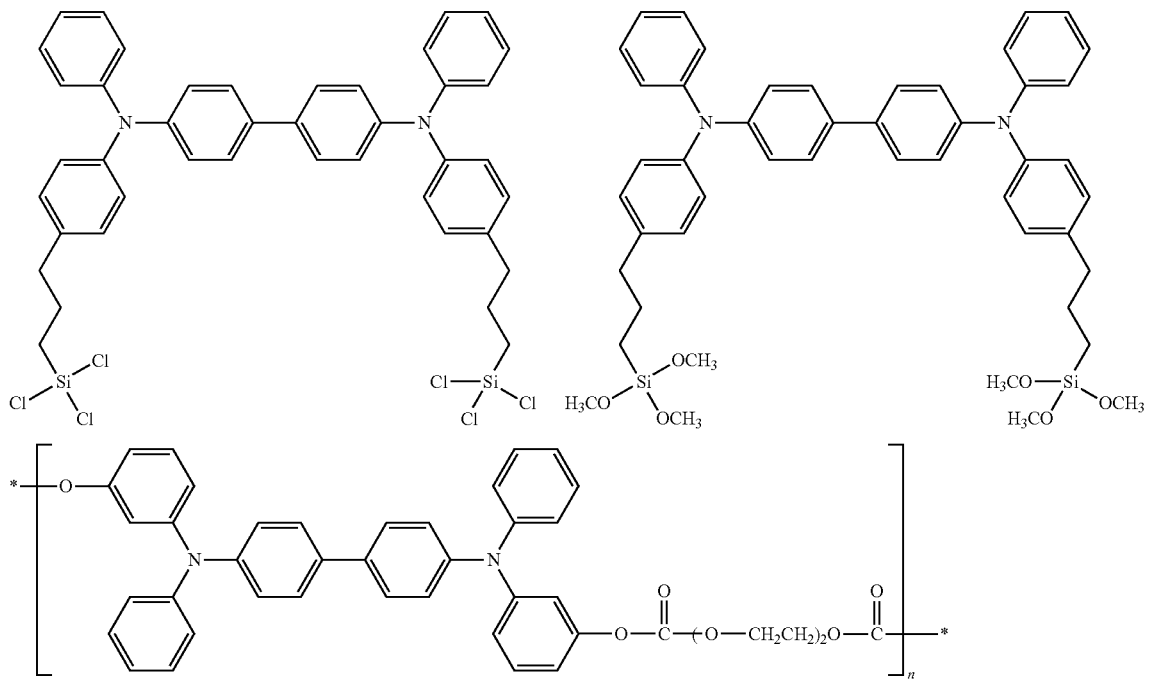

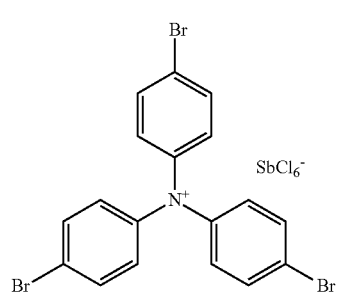
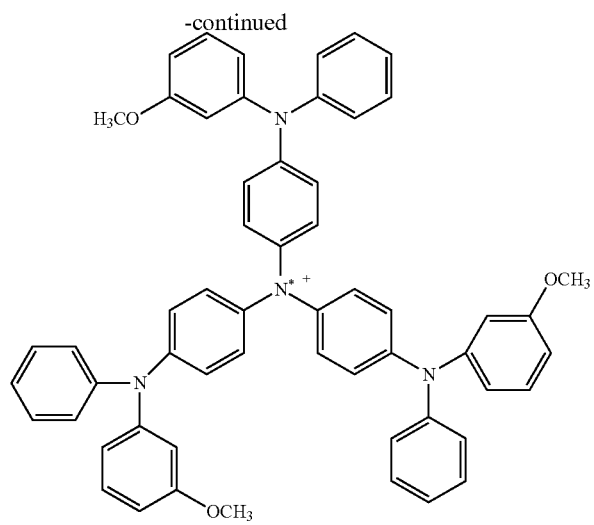
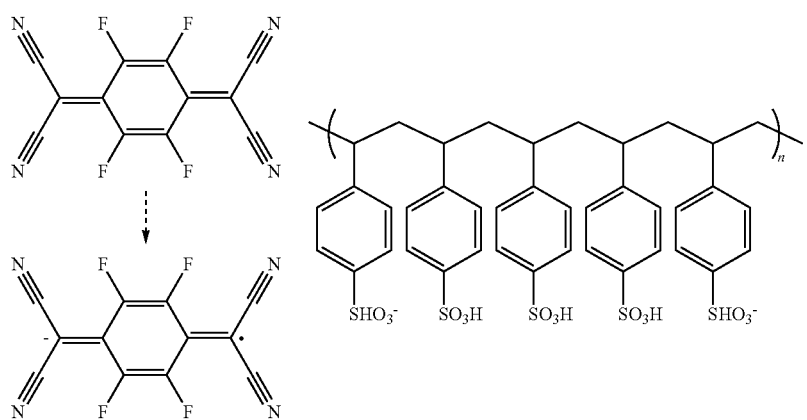
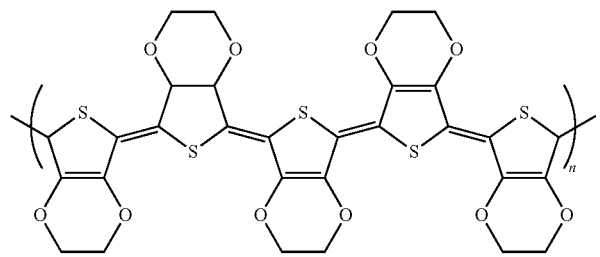
Preferred examples of a compound that may be used as the hole transporting material are shown below.
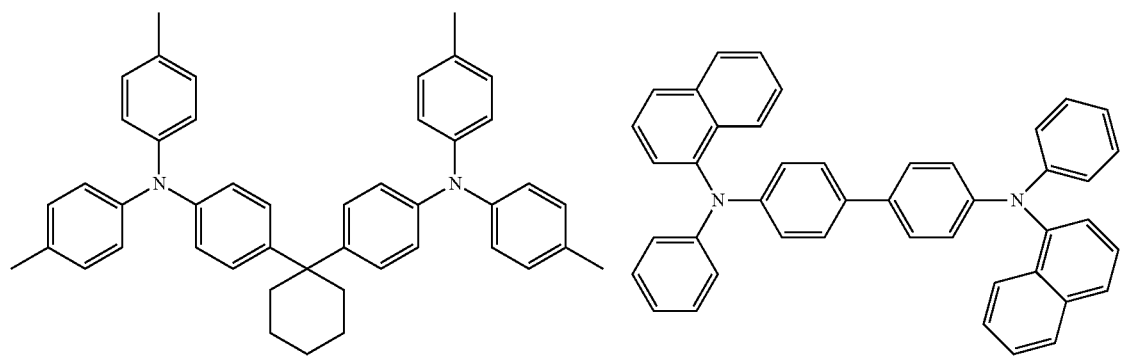

-continued
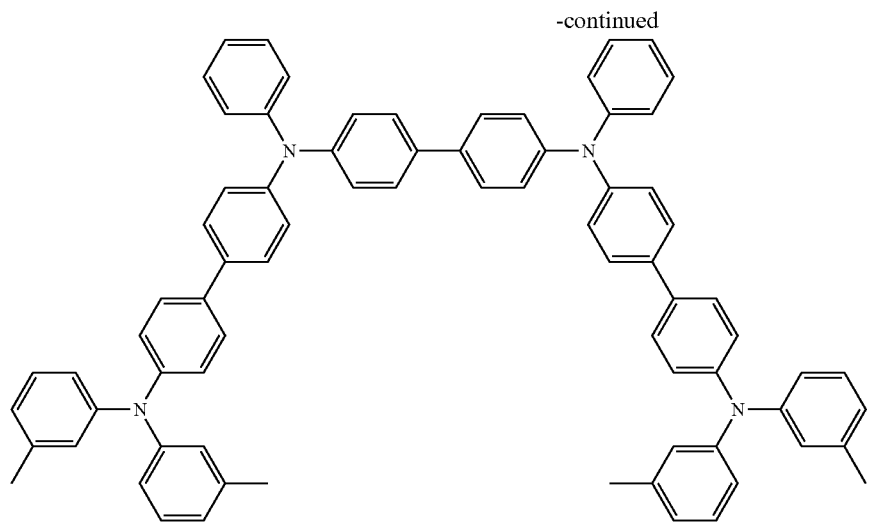
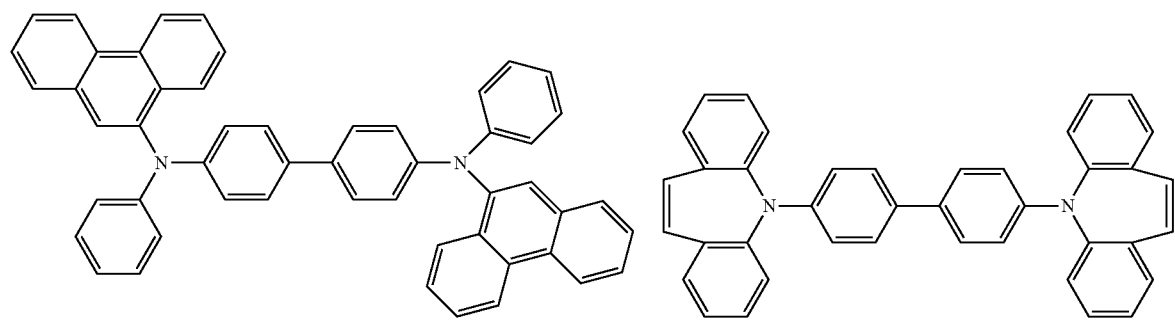
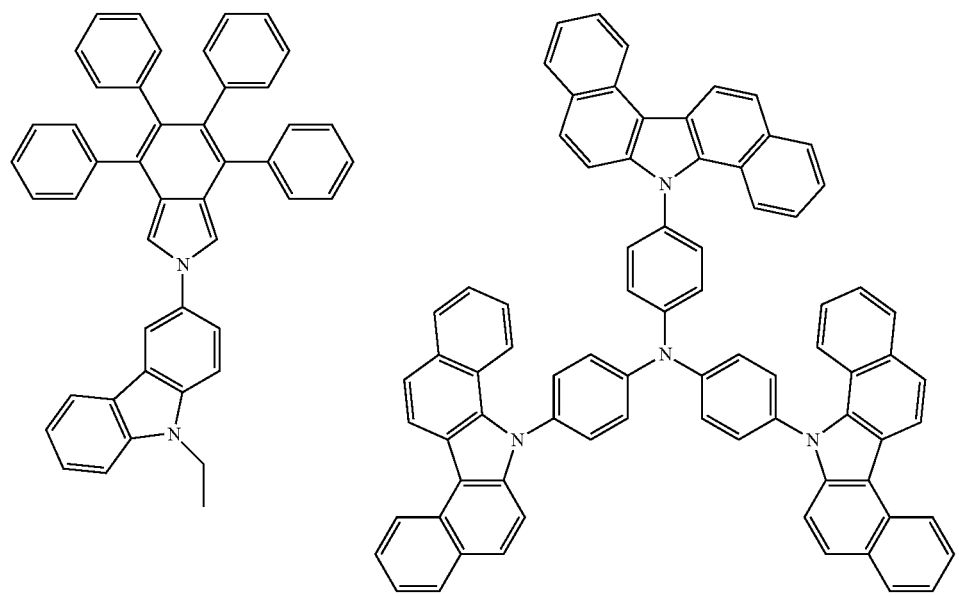

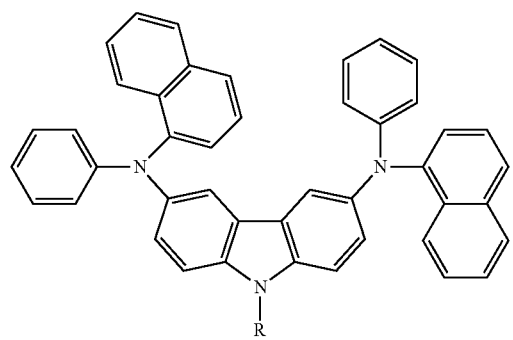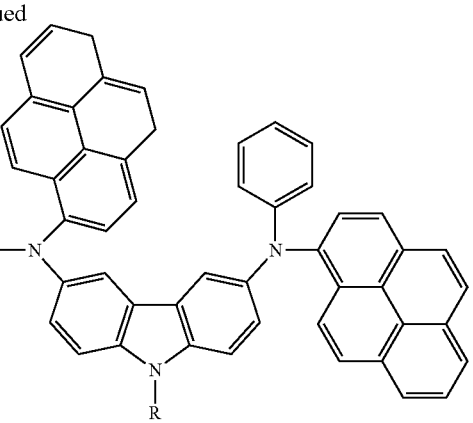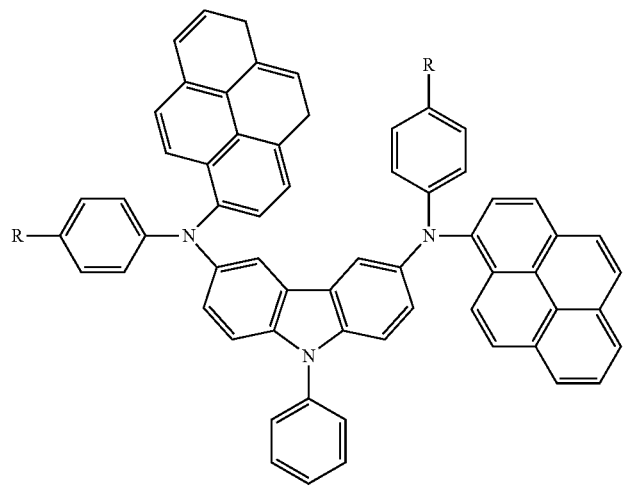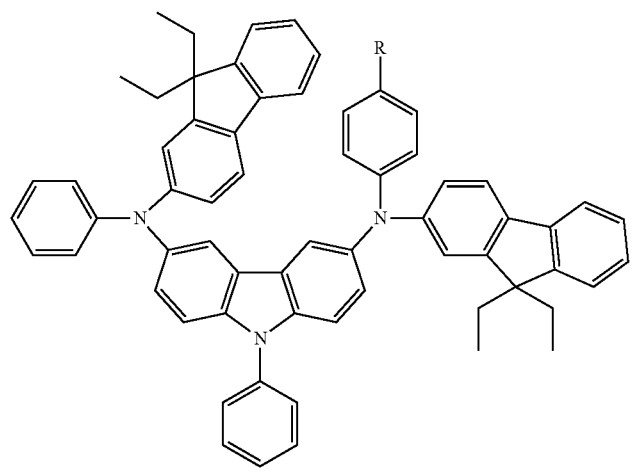

-continued
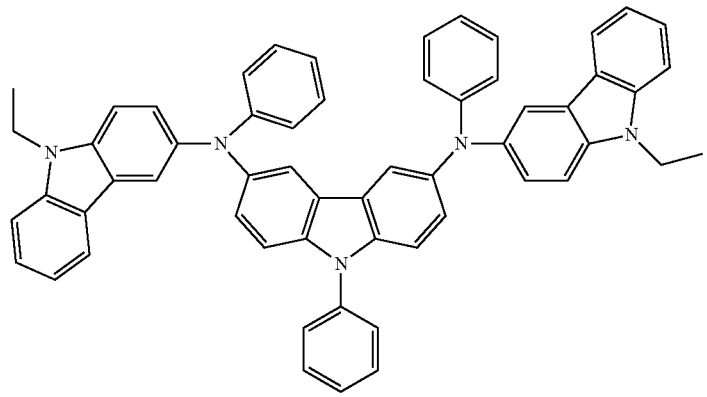
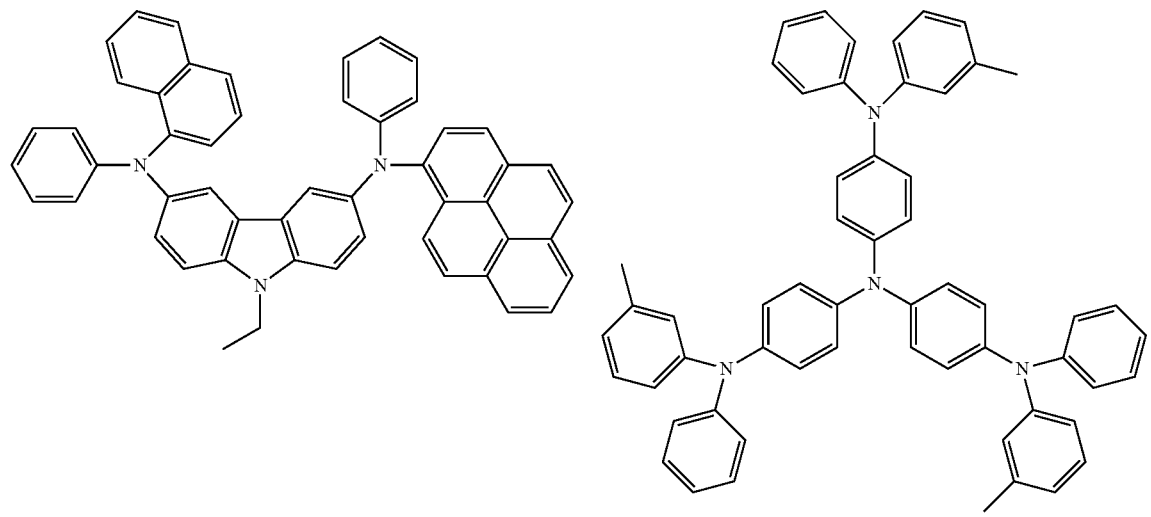
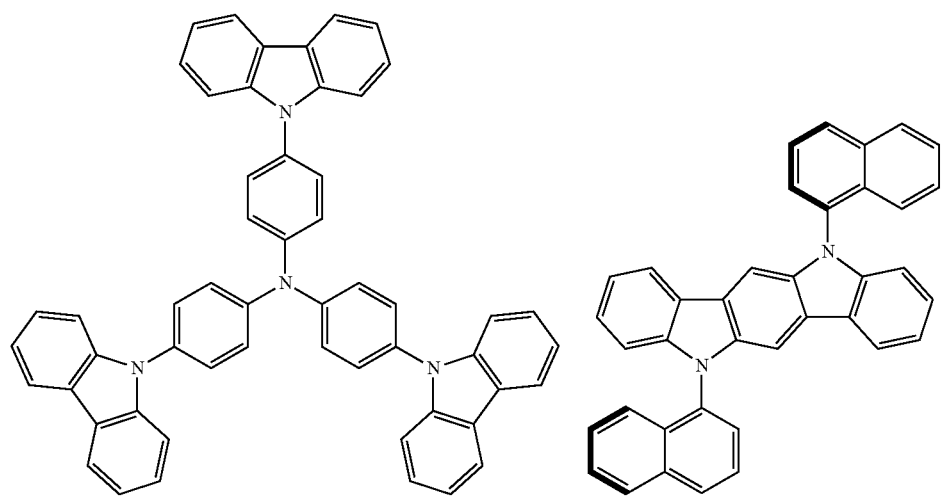

-continued
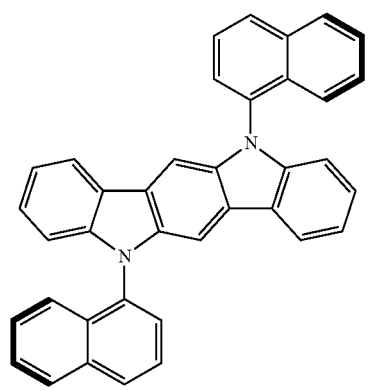
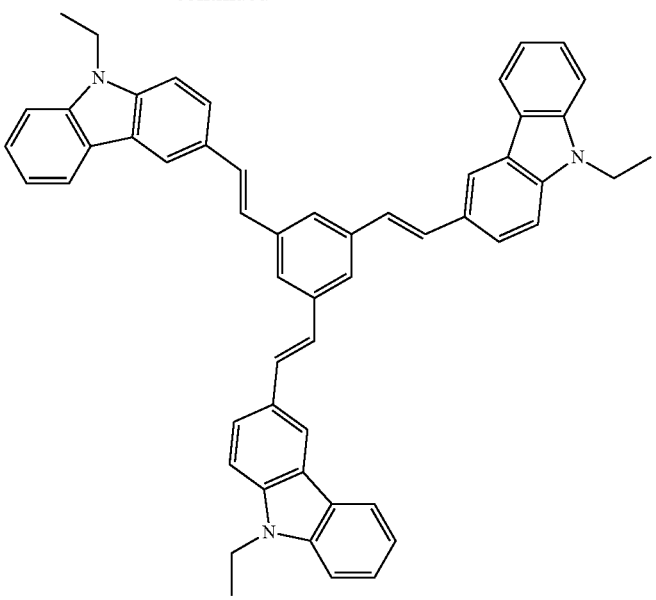
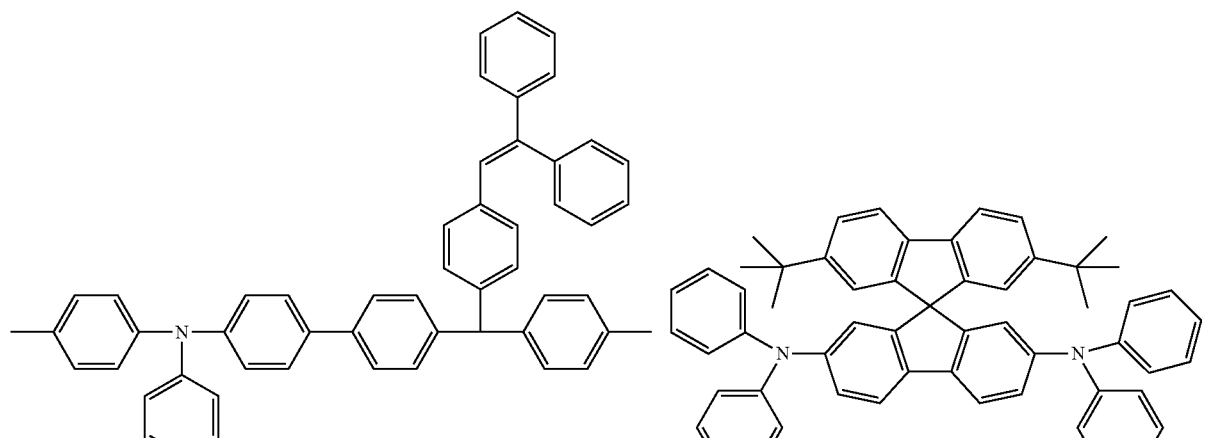
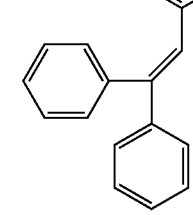
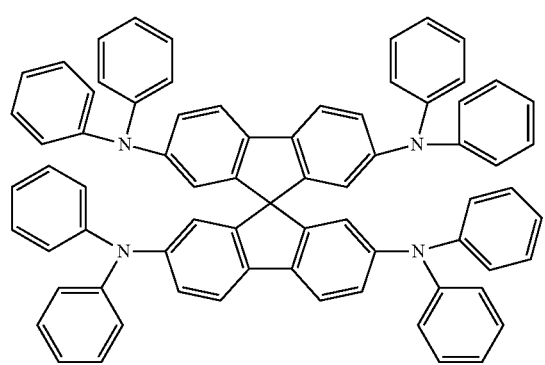
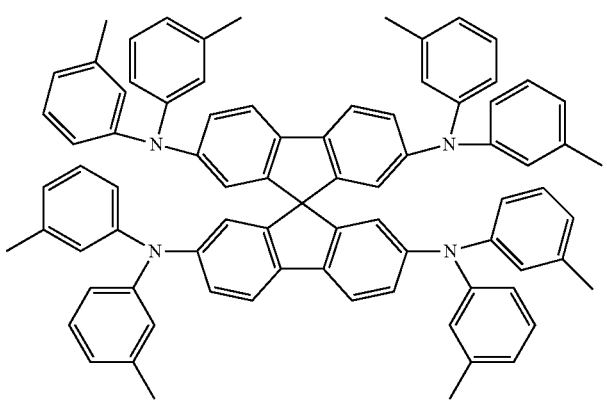

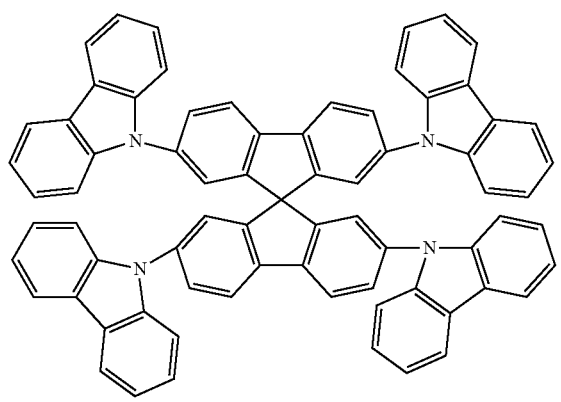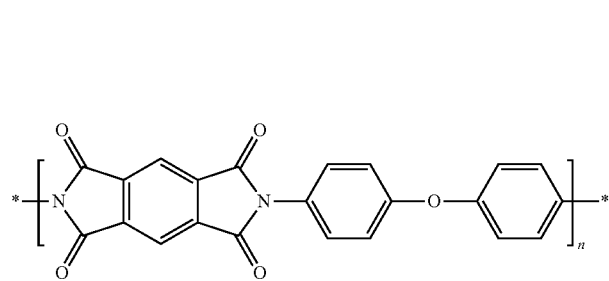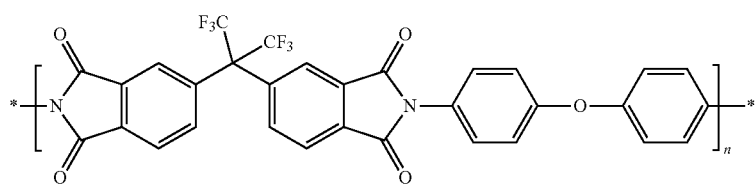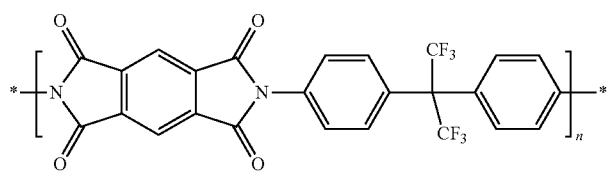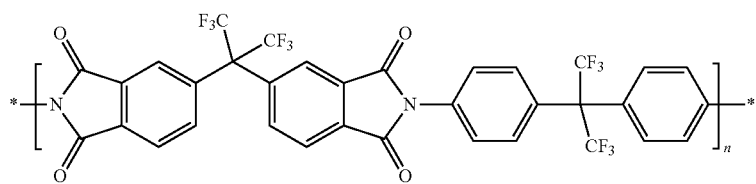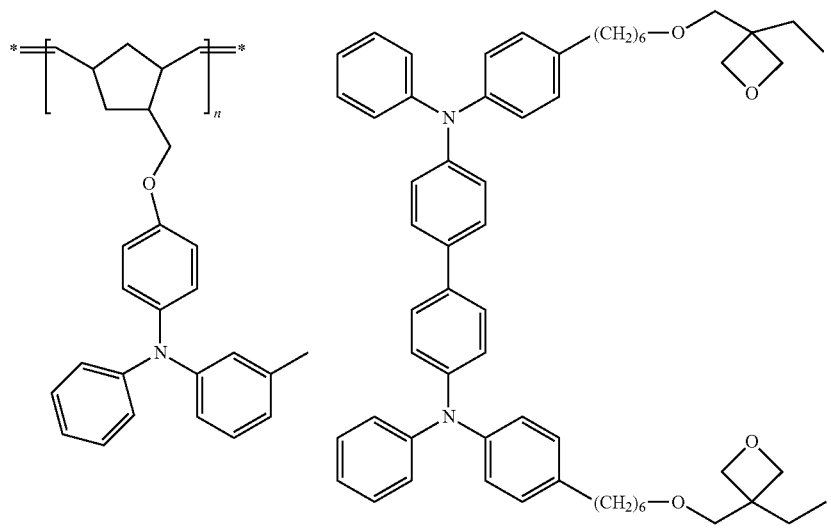

-continued
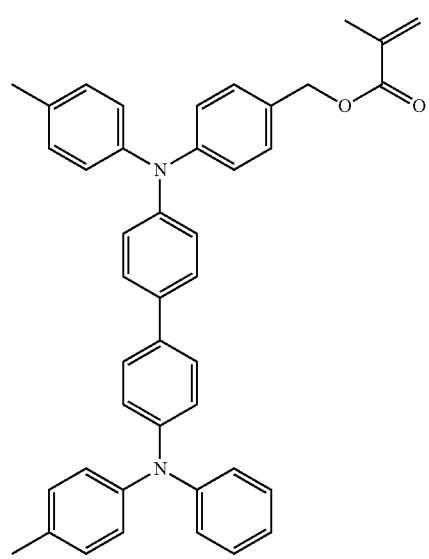
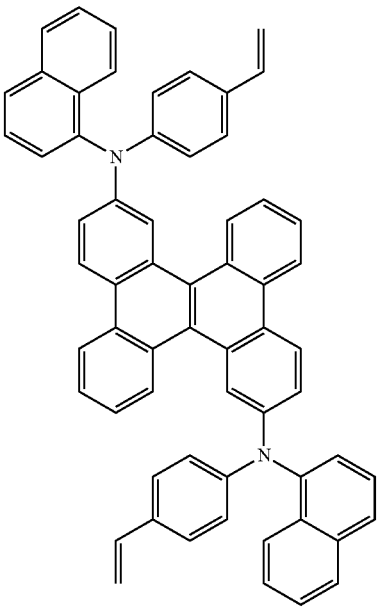
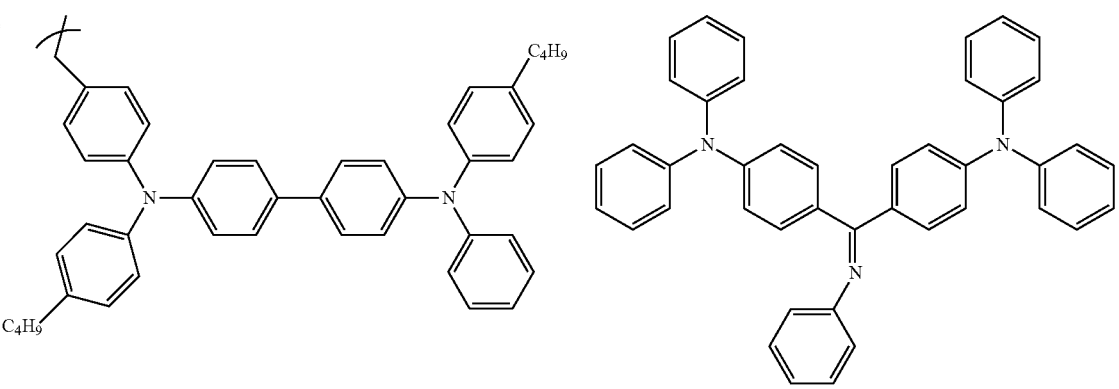
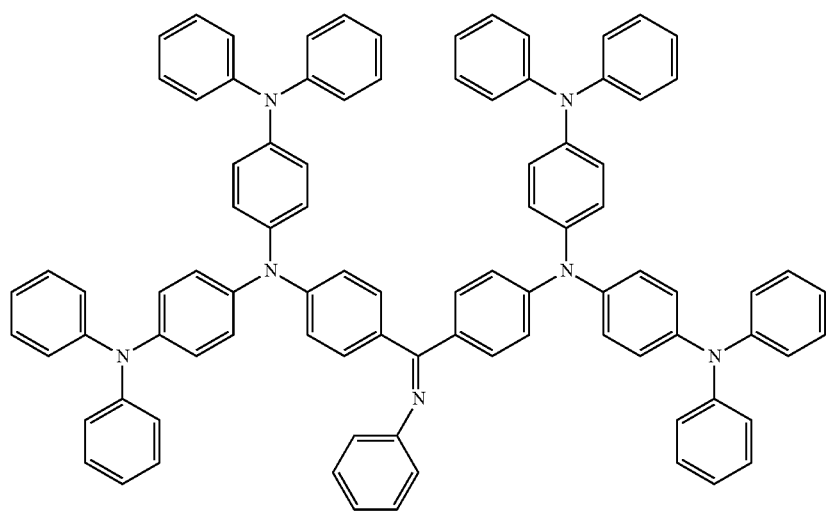

-continued
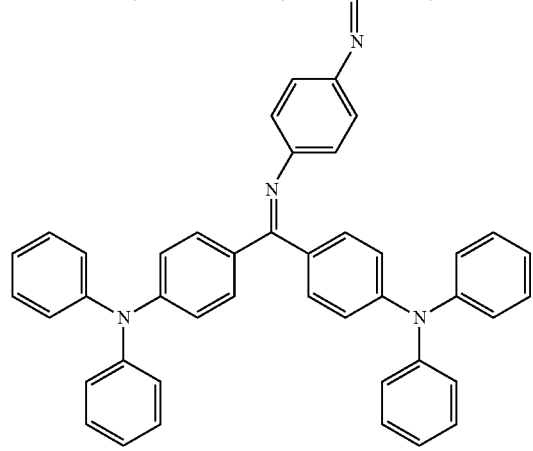
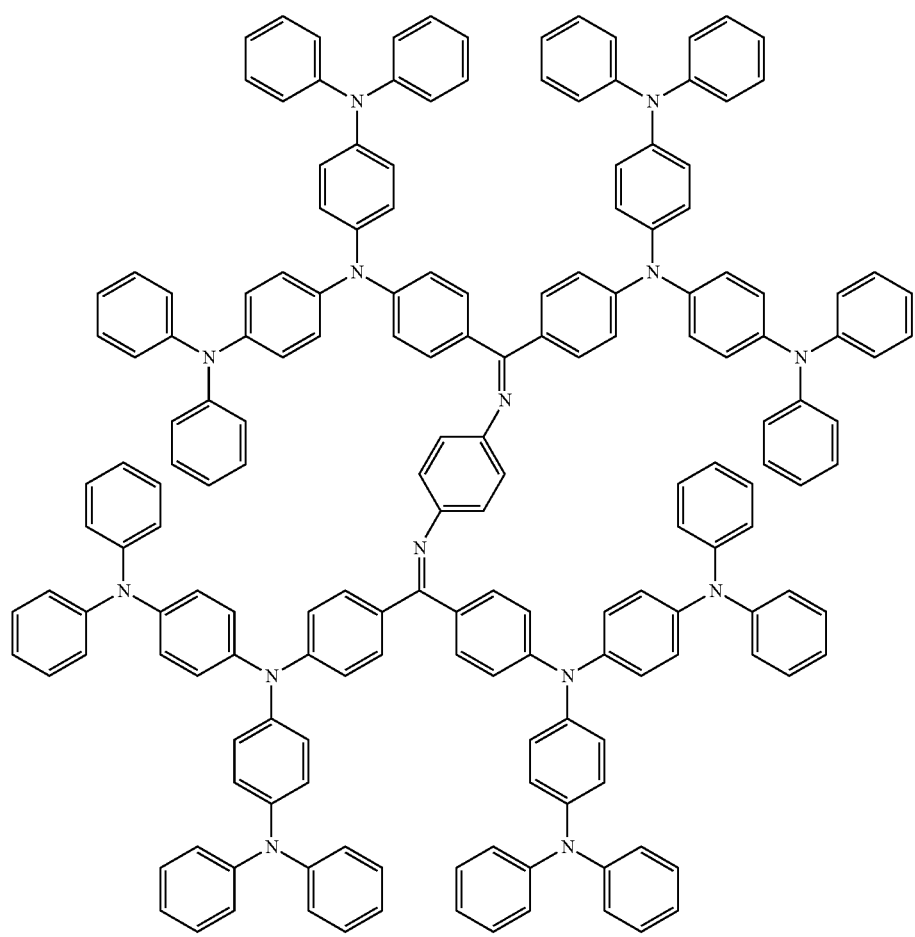 [SMILES: c1ccc(N(c2ccccc2)c2ccc(N(c3ccc(C(=Nc4ccc(N=C(c5ccc(N(c6ccc(N(c7ccccc7)c7ccccc7)cc6)c6ccc(N(c7ccccc7)c7ccccc7)cc6)cc5)c5ccc(N(c6ccc(N(c7ccccc7)c7ccccc7)cc6)c6ccc(N(c7ccccc7)c7ccccc7)cc6)cc5)cc4)c4ccc(N(c5ccc(N(c6ccccc6)c6ccccc6)cc5)c5ccc(N(c6ccccc6)c6ccccc6)cc5)cc4)cc3)c3ccc(N(c4ccccc4)c4ccccc4)cc3)cc2)cc1]

Preferred examples of a compound that may be used as the electron barrier material are shown below.
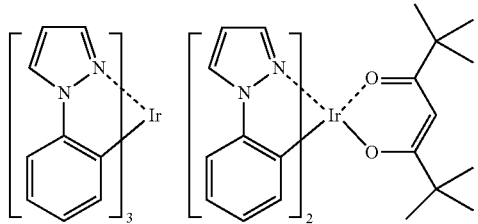
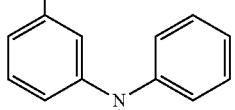
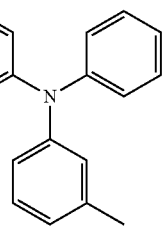
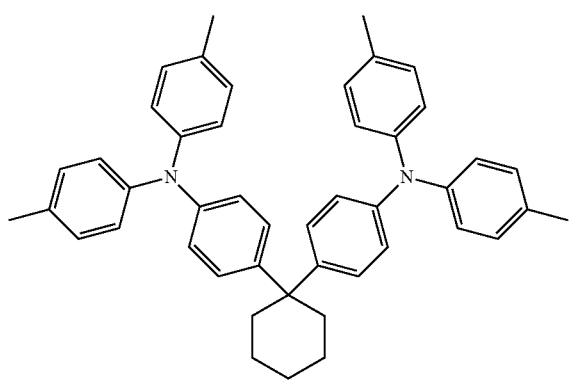
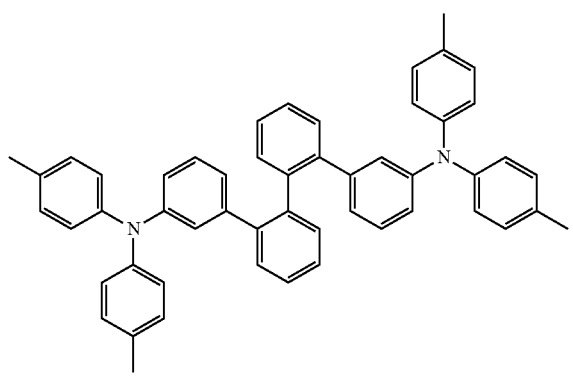
Preferred examples of a compound that may be used as the hole barrier material are shown below.
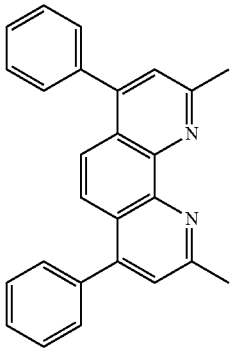

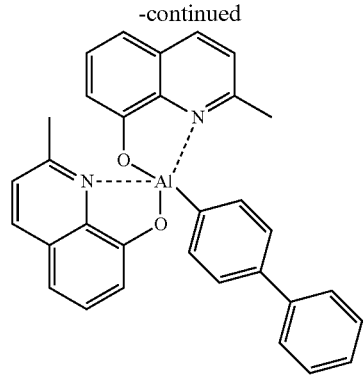
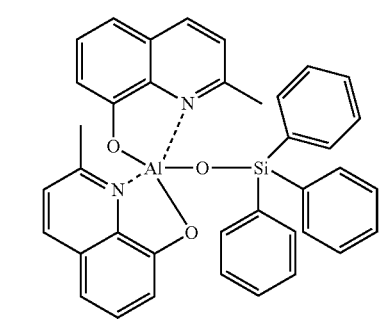
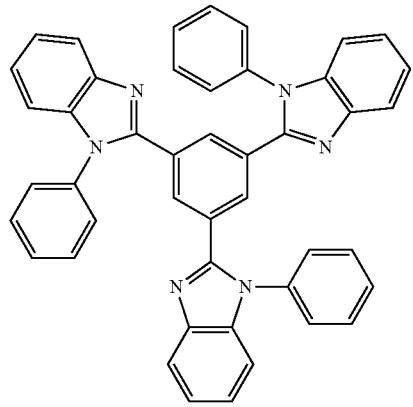
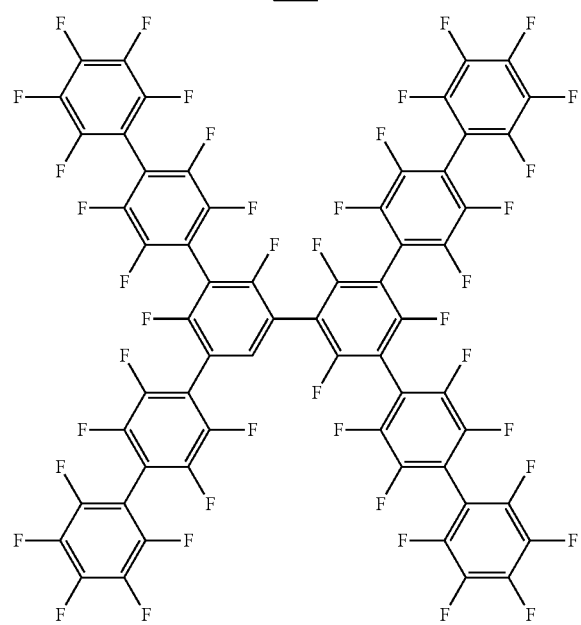
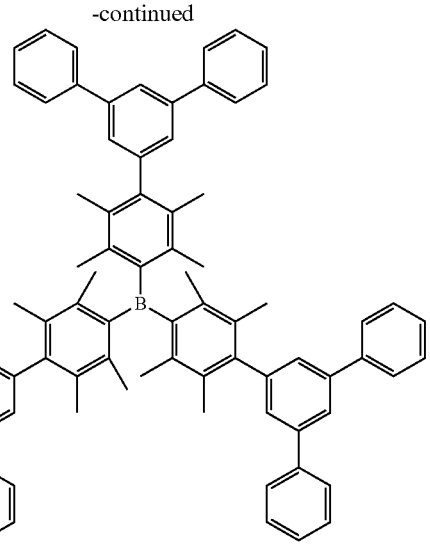
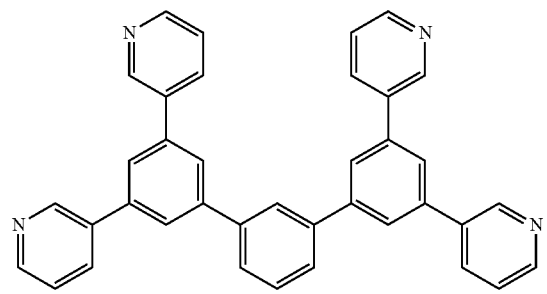
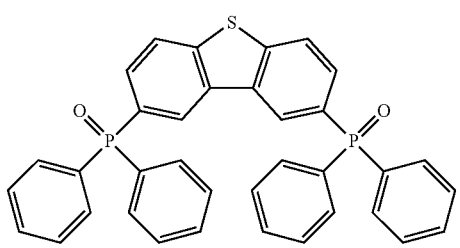
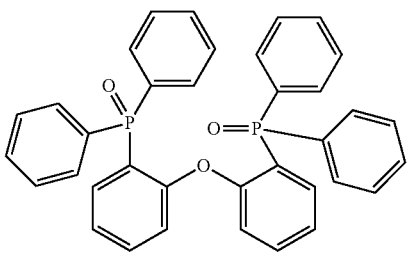
Preferred examples of a compound that may be used as the electron transporting material are shown below.

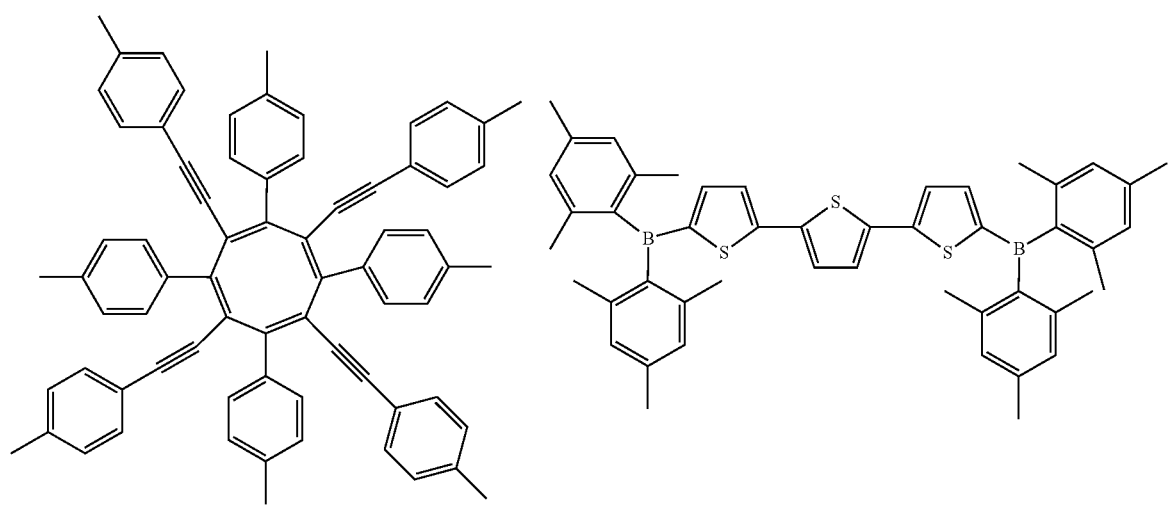
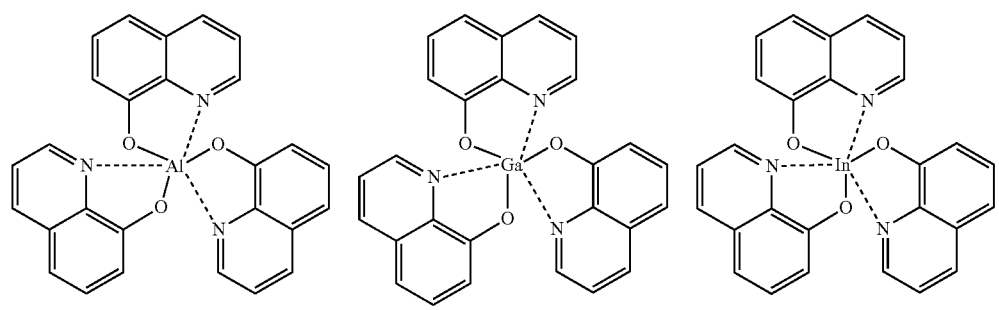
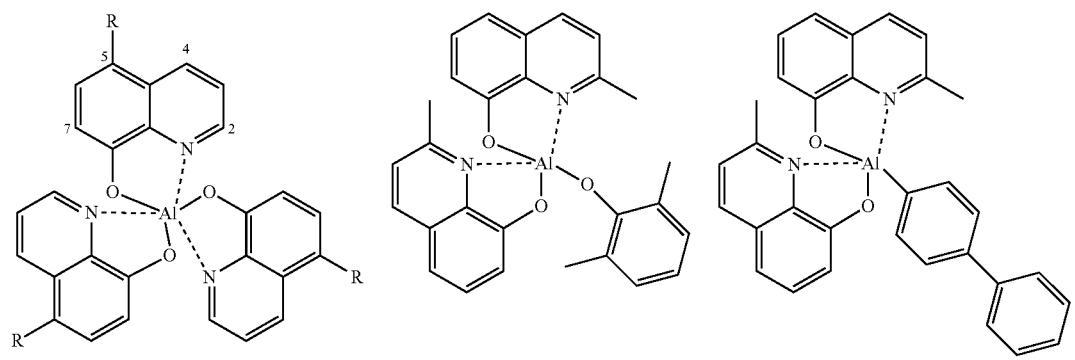
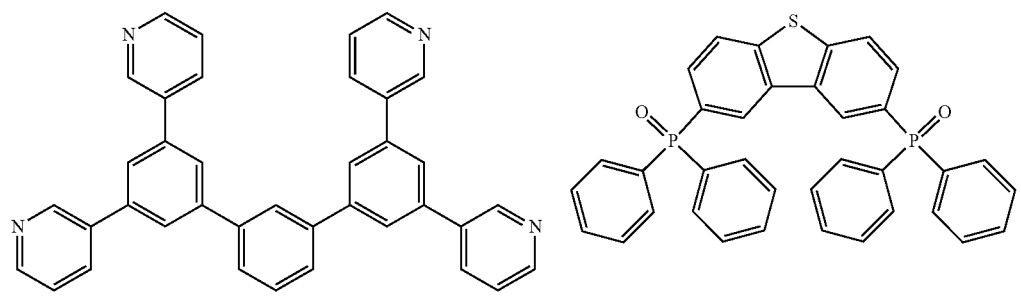

-continued
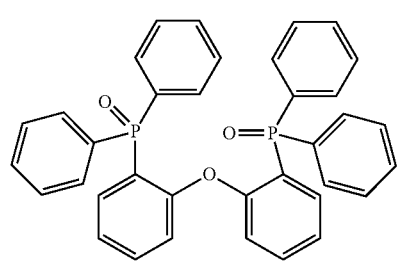
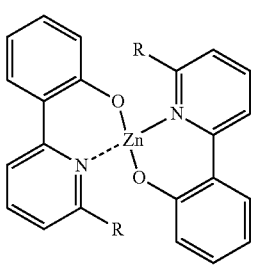
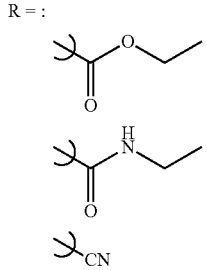
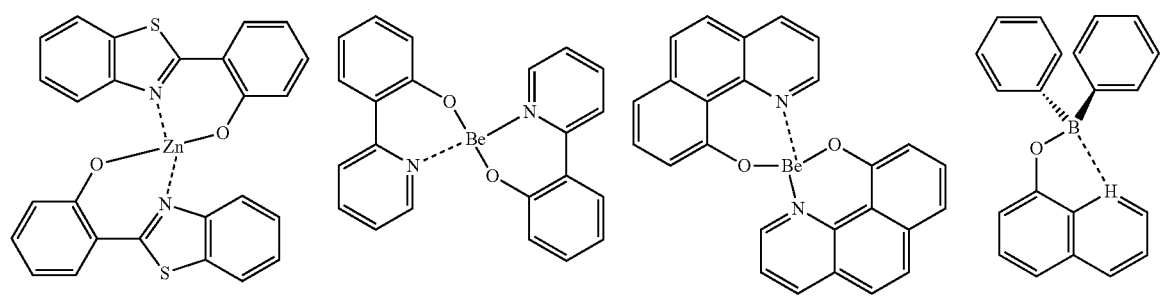
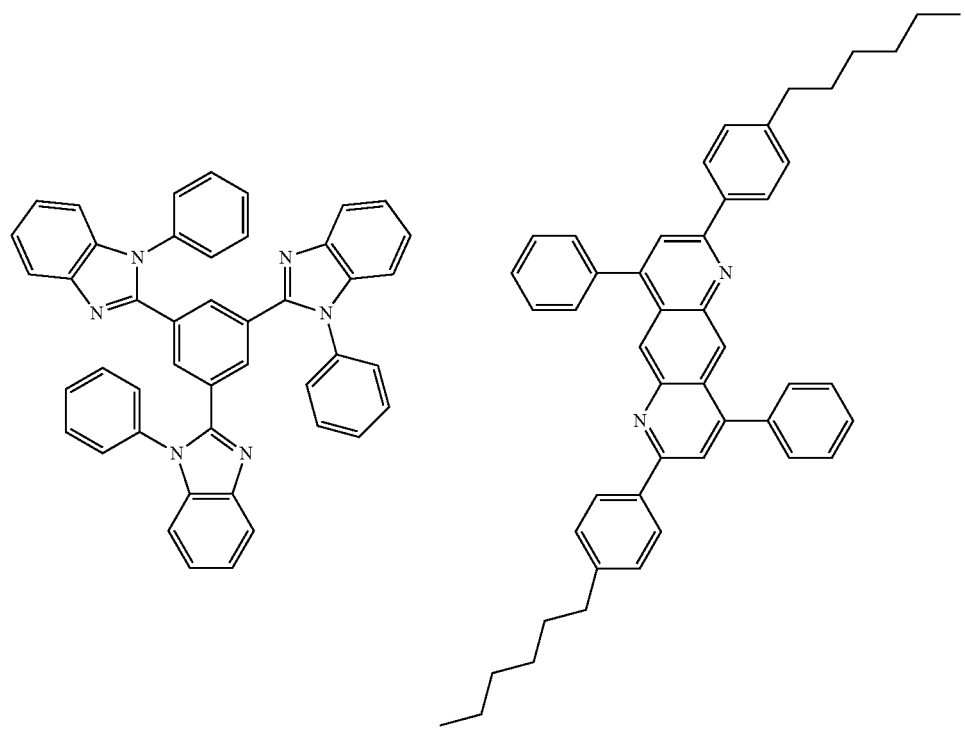

-continued
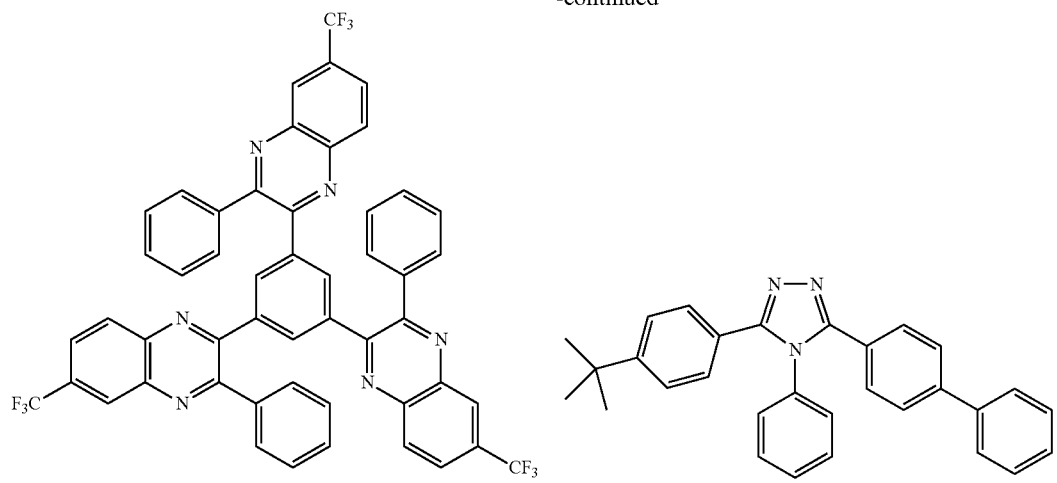
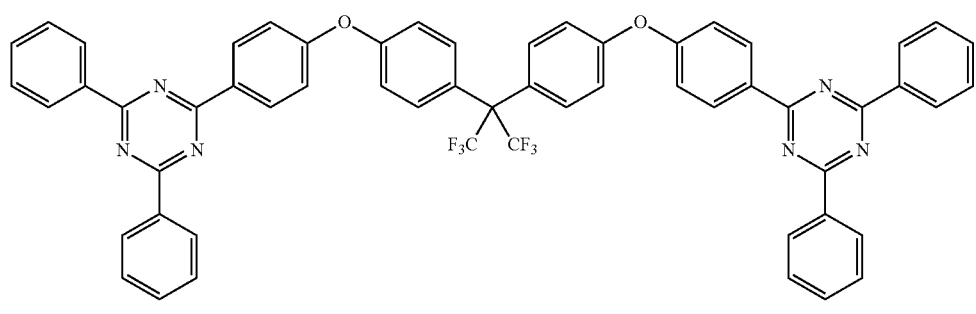
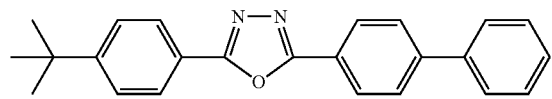
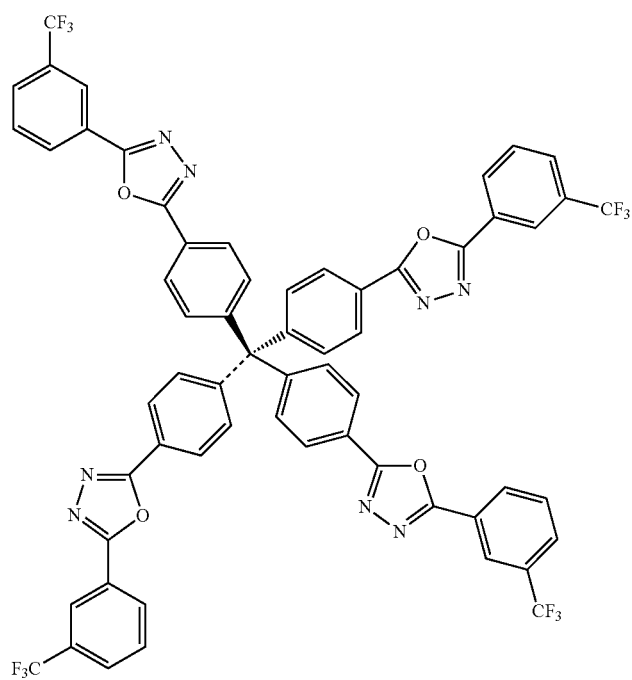

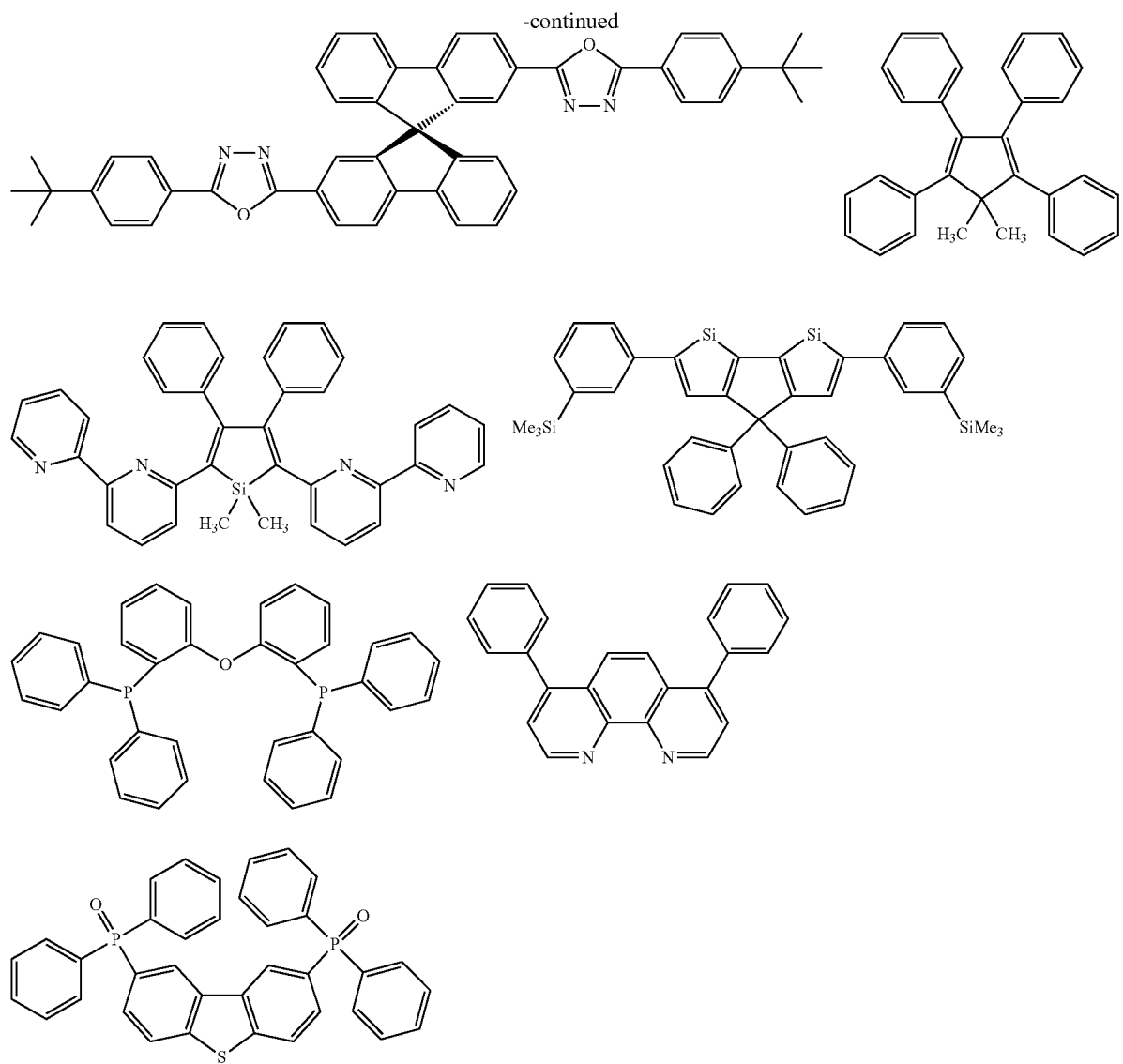
Preferred examples of a compound that may be used as the electron injection material are shown below.
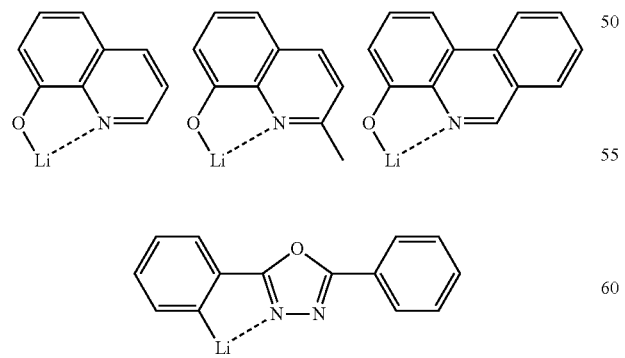
Preferred examples of a compound as a material that may be added are shown below. For example, the compound may be added as a stabilizing material.
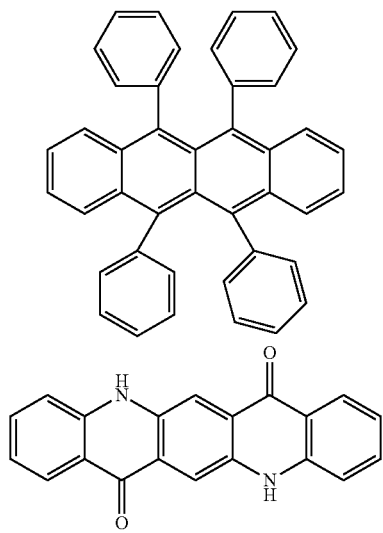

-continued

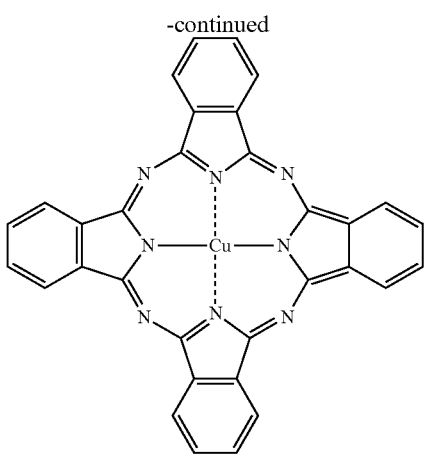

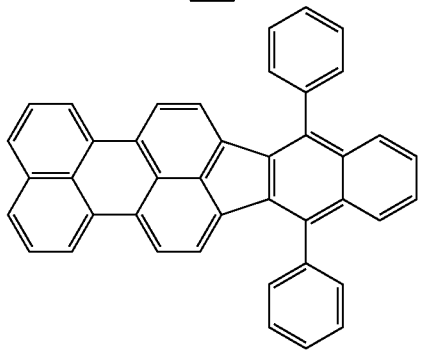

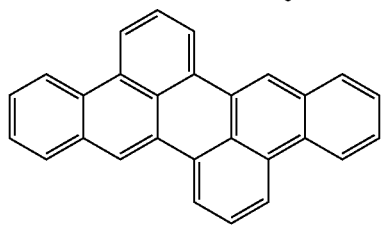

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light or delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not be observed with a normal organic compound, such as the compound of the invention, at room temperature since the excited triplet energy is converted to heat of the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a device having a structure with plural devices disposed in an array, and a device having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

Synthesis of Compound 1

(1) Synthesis of 2-(4-aminophenyl)-4,6-diphenyl-1,3,5-triazone

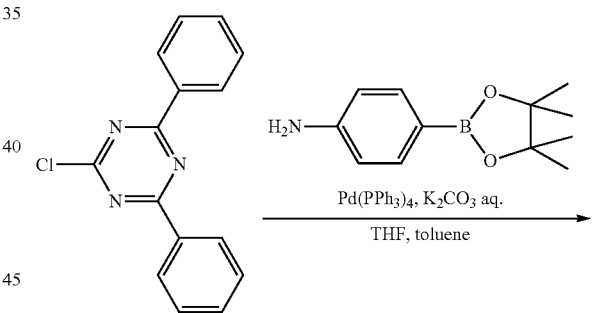

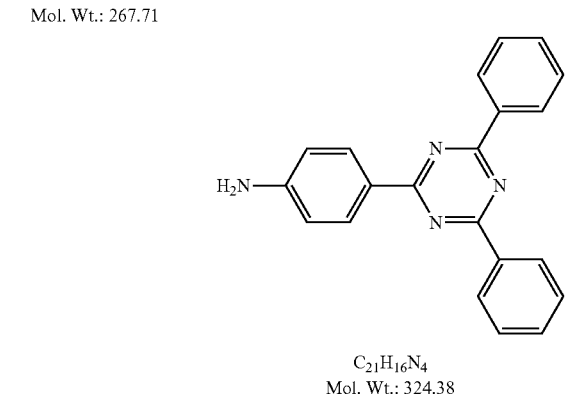

To a two-neck flask having been substituted with nitrogen, 2-chloro-4,6-diphenyl-1,3,5-triazine (20 mmol, 5.35 g), 4-(4,4,5,5-tetramethyl-1,3,2-dioxaborolan-2-yl) aniline (22 mmol, 4.82 g), tetrakis(triphenylphosphine) palladium(0) (1.0 mmol, 1.16 g), 150 mL of tetrahydrofuran (THF) and 100 mL of toluene were added, and stirred under room temperature for 10 minutes. An aqueous solution containing potassium carbonate (40 mmol, 5.53 g) and 100 mL of water was added thereto, and the mixture was heated under refluxing for 48 hours. After standing to cool to room temperature, ethyl acetate and a sodium chloride aqueous solution were added, and the organic layer was separated and extracted. The organic layer was dehydrated over anhydrous magnesium sulfate, and the solvent was distilled off to provide a brown solid matter. Chloroform was added thereto, and an insoluble solid matter was filtered off under suction, thereby providing 2-(4-aminophenyl)-4,6-diphenyl-1,3,5-triazine as the target product (yield amount: 4.60 g, yield: 71%).

$^1$H-NMR (CDCl$_3$, 300 MHz) δ=4.11 (s, 2H), 6.80 (d, 2H), 7.54-7.60 (m, 6H), 8.61 (s, 2H), 8.74 (d, 4H) MALDI-MS m/z: 324

(2) Synthesis of 2-(4-bromophenyl)-4,6-diphenyl-1,3,5-triazine

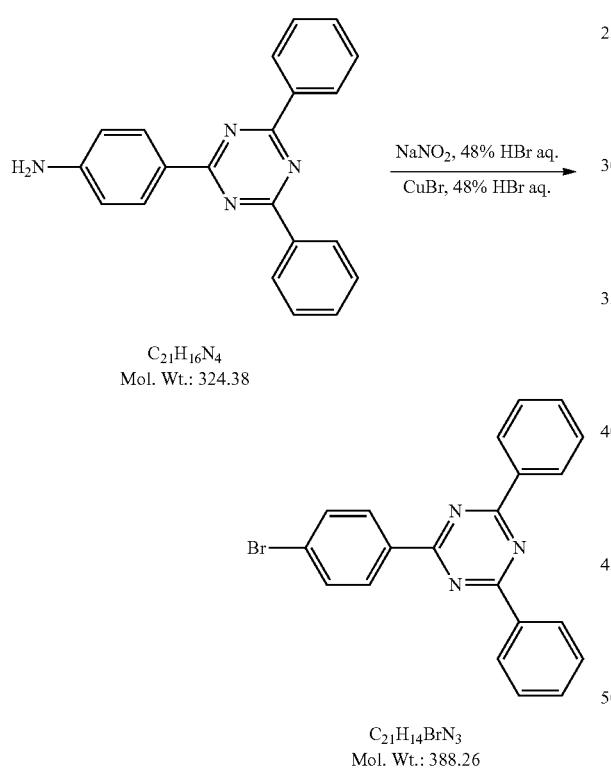

A mixed solution of 2-(4-aminophenyl) 4,6-diphenyl-1,3,5-triazine (13.7 mmol, 4.45 g) and 20 mL of hydrobromic acid (47%) was cooled to 0 to 5° C. over an ice bath. An aqueous solution containing sodium nitrite (13.7 mmol, 946.8 mg) and 20 mL of water was cooled over an ice bath, and slowly added dropwise to the reaction solution, which was stirred over an ice bath for 1 hour. After adding a mixed solution of copper(I) bromide (8.24 mmol, 1.18 g) and 8 mL of hydrobromic acid (47%) was slowly added dropwise to the cooled reaction solution, which was stirred for several minutes under room temperature. The reaction solution was heated to 115° C. over an oil bath and refluxed overnight. After standing to cool to room temperature, the reaction solution was cooled over an ice bath and neutralized with sodium hydrogencarbonate. Chloroform and a sodium chloride aqueous solution were added thereto, and the organic layer was separated and extracted. The organic layer was dehydrated over anhydrous magnesium sulfate, and the solvent was distilled off. 2-(4-Bromophenyl)-4,6-diphenyl-1,3,5-triazine as the target product was isolated and purified by silica gel chromatography with a mixed solvent of chloroform and hexane (1/4) (yield amount: 3.19 g, yield: 60%).

$^1$H-NMR (CDCl$_3$, 300 MHz) δ=7.58 (m, 6H), 7.70 (d, 2H), 8.64 (s, 2H), 8.76 (s, 4H) MALDI-MS m/z: 388

(3) Synthesis of Compound 1

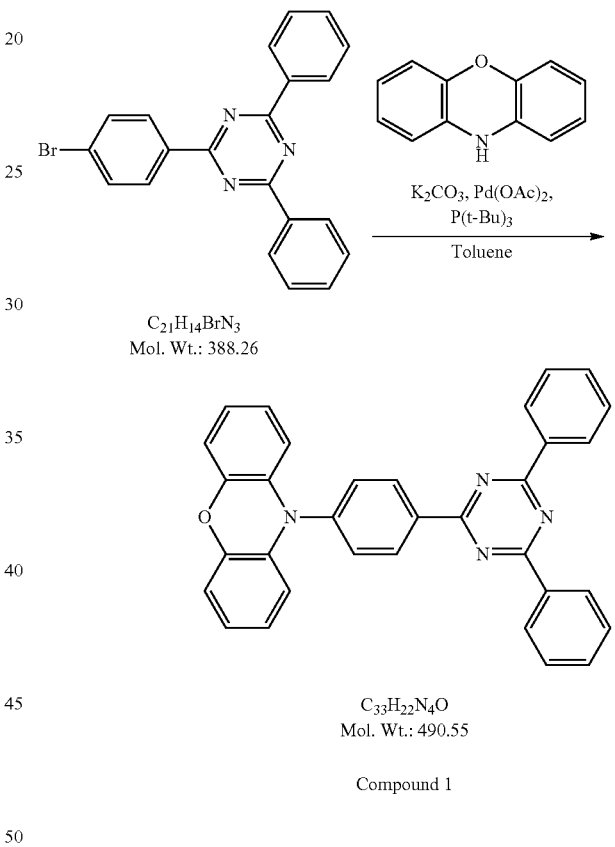

To a two-neck flask having been substituted with nitrogen, 2-(4-bromophenyl)-4,6-diphenyl-1,3,5-triazine (3.0 mmol, 1.17 g), phenoxazine (3.3 mmol, 611.2 mg), potassium carbonate (9.0 mmol, 1.24 g) and 30 mL of toluene were added, and stirred under room temperature for 10 minutes. A mixed solution of palladium(II) acetate (0.09 mmol, 20.2 mg), tri-tert-butylphosphine (0.33 mmol, 66.8 mg) and 30 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off. The compound 1 as the target product was isolated and purified by silica gel chromatography with a mixed solvent of chloroform and hexane (1/4) (yield amount: 912.4 mg, yield: 62%).

$^1$H-NMR (CDCl$_3$, 300 MHz) δ=6.04 (d, 2H), 6.60 (t, 2H), 6.66 (t, 2H), 6.72 (d, 2H), 7.57 (m, 8H), 8.80 (d, 4H), 8.99 (d, 2H) MALDI-MS m/z: 491

Synthesis Example 2

Synthesis of Compound 2

(1) Synthesis of 2,4-bis(4-bromophenyl)-6-phenyl-1,3,5-triazine

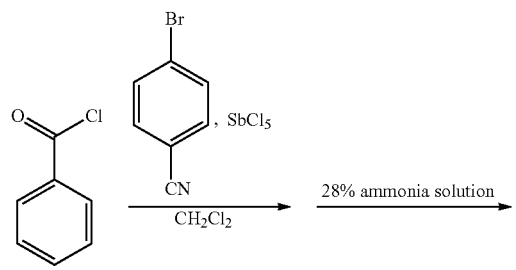

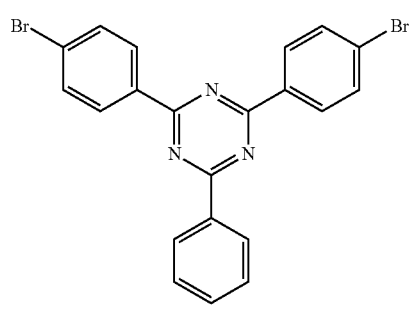

To a two-neck flask having been substituted with nitrogen, benzoyl chloride (11.0 mmol, 1.55 g), 4-bromobenzonitrile (22.0 mmol, 4.00 g) and 15 mL of methylene chloride were added, and stirred under cooling (0 to 5° C.) over an ice bath for 30 minutes. Antimony chloride (11.0 mmol, 3.30 g) was added dropwise thereto, and the mixture was stirred at room temperature for 1 hour. Thereafter, the mixture was heated under refluxing for 12 hours. After standing to cool to room temperature, the yellow solid matter thus deposited was collected by filtering under suction and dried in vacuum. The resulting yellow solid matter was added to 75 mL of 28% aqueous ammonia cooled (0 to 5° C.) over an ice bath, and the mixture was stirred for 30 minutes. Thereafter, the mixture was stirred at room temperature for 3 hours. The white solid matter thus deposited was collected by filtering under suction, washed with water, and then dried in vacuum. The resulting white solid matter was added to 30 mL of N,N-dimethylformamide having been heated to 155° C., the mixture was stirred for 10 minutes, and the insoluble solid matter was filtered off under suction. The operation was repeated twice for purifying the product. Thereafter, N,N-dimethylformamide was distilled off under heating and reduced pressure, thereby providing 2,4-bis(4-bromophenyl)-6-phenyl-1,3,5-triazine as the target product (yield amount: 2.55 g, yield: 49.60).

(2) Synthesis of Compound 2

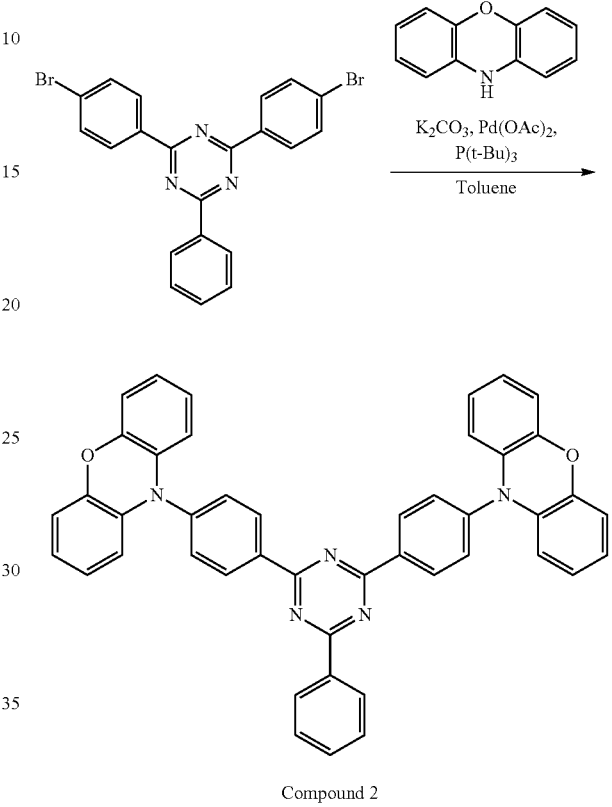

Compound 2

To a two-neck flask having been substituted with nitrogen, 2,4-bis(4-bromophenyl)-6-phenyl-1,3,5-triazine (1.28 mmol, 600 mg), phenoxazine (2.82 mmol, 522 mg), potassium carbonate (8.46 mmol, 1.17 g) and 25 mL of toluene were added, and stirred under room temperature for 10 minutes. A mixed solution of palladium(II) acetate (0.09 mmol, 20.2 mg), tri-tert-butylphosphine (0.31 mmol, 62.7 mg) and 25 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off. 2,4-bis(4-N-Phenoxazyl-phenyl)-6-phenyl-1,3,5-triazine as the target product was isolated and purified by silica gel chromatography with chloroform as a developing solvent (yield amount: 723 mg, yield: 84.1%).

$^1$H-NMR (CDCl$_3$, 300 MHz) δ=6.05 (d, 4H), 6.62 (t, 4H), 6.68 (t, 4H), 6.72 (d, 4H), 7.58 (m, 7H), 8.81 (d, 2H), 9.00 (d, 4H)

MS MALDI-MS m/z: 671

Synthesis Example 3

Synthesis of Compound 3

(1) Synthesis of 2,4,6-tri(4-bromophenyl)-1,3,5-triazine

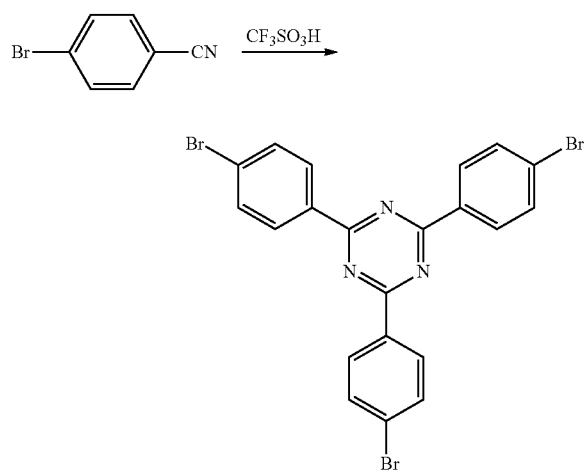

To a two-neck flask having been substituted with nitrogen, trifluoromethanesulfonic acid (66.6 mmol, 9.99 g) was added, and cooled (0 to 5° C.) over an ice bath. 4-Bromobenzonitrile (19.6 mmol, 3.57 g) was added thereto, and the mixture was stirred for 30 minutes. Thereafter, the mixture was stirred at room temperature for 12 hours. Water was added to the mixture, which was then neutralized with NaOH, and then washed with a mixed solvent of chloroform and acetone (50/50), and the organic layer was extracted. The organic layer was dehydrated over anhydrous magnesium sulfate, and the solvent was distilled off, thereby providing 2,4,6-tri(4-bromophenyl)-1,3,5-triazine as the target product (yield amount: 3.34 g, yield: 93.60).

(2) Synthesis of Compound 3

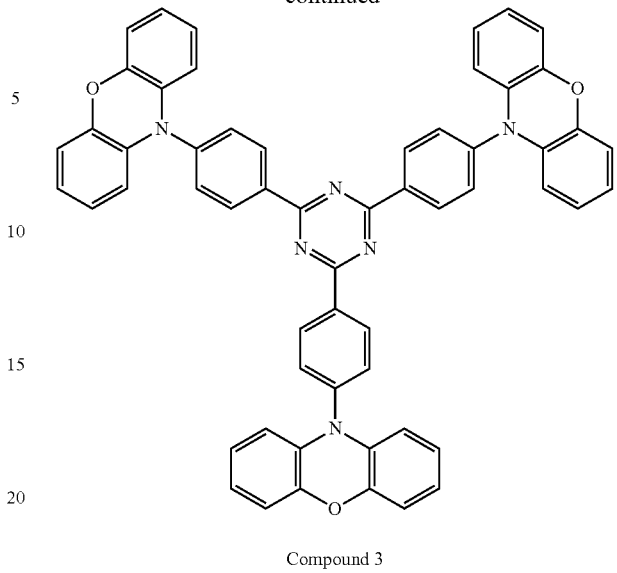

Compound 3

To a two-neck flask having been substituted with nitrogen, 2,4,6-tri(4-bromophenyl)-1,3,5-triazine (2.0 mmol, 1.09 g), phenoxazine (6.6 mmol, 1.22 g), potassium carbonate (19.8 mmol, 2.74 g) and 60 mL of toluene were added, and stirred under room temperature for 10 minutes. A mixed solution of palladium(II) acetate (0.20 mmol, 45.0 mg), tri-tert-butylphosphine (0.73 mmol, 147.7 mg) and 60 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off. 2,4,6-tri(4-N-Phenoxazylphenyl)-1,3,5-triazine as the target product was isolated and purified by silica gel chromatography with a mixed solvent of chloroform and hexane (1/1) (yield amount: 1.65 g, yield: 96.50).

$^1$H-NMR (CDCl$_3$, 300 MHz) δ=6.06 (d, 6H), 6.63 (t, 6H), 6.69 (t, 6H), 6.73 (d, 6H), 7.60 (d, 6H), 9.01 (d, 6H)

MS MALDI-MS m/z: 852

Synthesis Example 4

Synthesis of Compound 4

(1) Synthesis of 2-(3-bromophenyl)-4,6-diphenyl-1,3,5-triazine

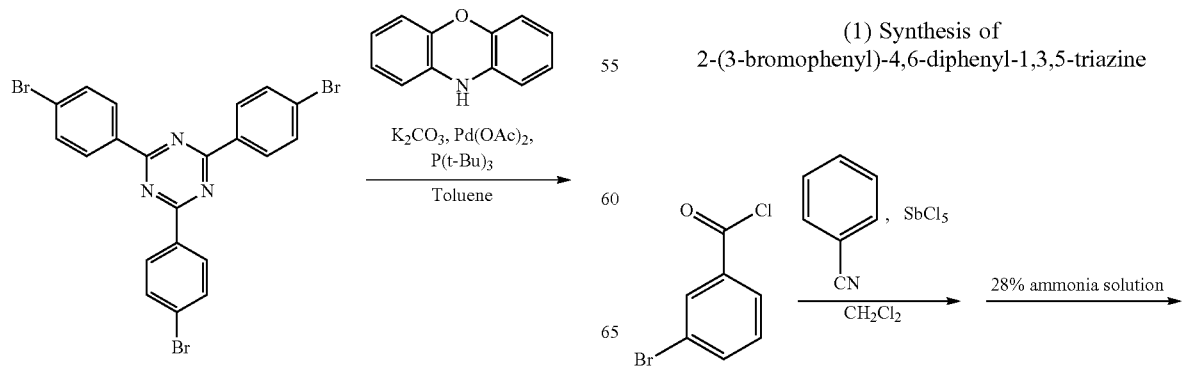

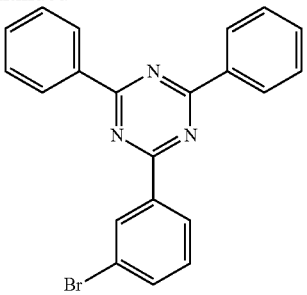

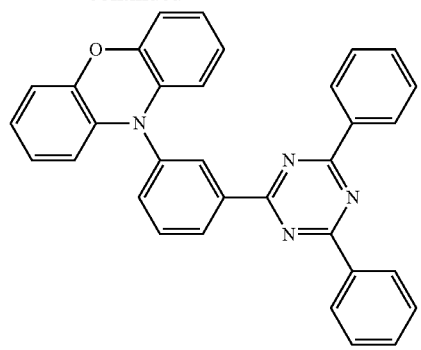

Compound 4

To a two-neck flask having been substituted with nitrogen, 3-bromobenzoyl chloride (11.0 mmol, 2.41 g), benzonitrile (22.0 mmol, 2.27 g) and 15 mL of methylene chloride were added, and stirred under cooling (0 to 5° C.) over an ice bath for 30 minutes. Antimony chloride (11.0 mmol, 3.30 g) was added dropwise thereto, and then the mixture was stirred at room temperature for 1 hour. Thereafter, the mixture was heated under refluxing for 12 hours. After standing to cool to room temperature, the yellow solid matter thus deposited was collected by filtering under suction and dried in vacuum. The resulting yellow solid matter was added to 75 mL of 28% aqueous ammonia cooled (0 to 5° C.) over an ice bath, and the mixture was stirred for 30 minutes. Thereafter, the mixture was stirred at room temperature for 3 hours. The white solid matter thus deposited was collected by filtering under suction, washed with water, and then dried in vacuum. The resulting white solid matter was added to 30 mL of N,N-dimethylformamide having been heated to 155° C., the mixture was stirred for 10 minutes, and the insoluble solid matter was filtered off under suction. The operation was repeated twice for purifying the product. Thereafter, N,N'-dimethylformamide was distilled off under heating and reduced pressure, thereby providing 2-(3-bromophenyl)-4,6-diphenyl-1,3,5-triazine as the target product (yield amount: 2.85 g, yield: 66.7%).

$^1$H-NMR (CDCl$_3$, 300 MHz) δ=5.99 (d, 2H), 6.61 (t, 2H), 6.67 (t, 2H), 6.73 (d, 2H), 7.55 (m, 7H), 7.82 (t, 1H), 8.75 (s, 1H), 8.76 (d, 4H), 8.90 (d, 1H)

MS MALDI-MS m/z: 490

(2) Synthesis of Compound 4

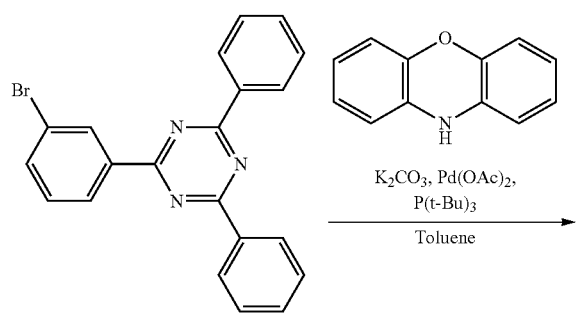

To a two-neck flask having been substituted with nitrogen, 2-(3-bromophenyl)-4,6-diphenyl-1,3,5-triazine (3.50 mmol, 1.36 g), phenoxazine (3.85 mmol, 713.1 mg), potassium carbonate (11.6 mmol, 1.60 g) and 20 mL of toluene were added, and stirred under room temperature for 10 minutes. A mixed solution of palladium(II) acetate (0.12 mmol, 27.0 mg), tri-tert-butylphosphine (0.42 mmol, 85.0 mg) and 20 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off. The compound 4 was isolated and purified by silica gel chromatography with a mixed solvent of chloroform and hexane (1/1) (yield amount: 1.45 g, yield: 84.3%).

$^1$H-NMR (CDCl$_3$, 300 MHz) δ=5.99 (d, 2H), 6.61 (t, 2H), 6.67 (t, 2H), 6.73 (d, 2H), 7.55 (m, 7H), 7.82 (t, 1H), 8.75 (s, 1H), 8.76 (d, 4H), 8.90 (d, 1H)

MS MALDI-MS m/z: 490

Synthesis Example 5

Synthesis of Compound 5

(1) Synthesis of 2,4-bis(3-bromophenyl)-6-phenyl-1,3,5-triazine

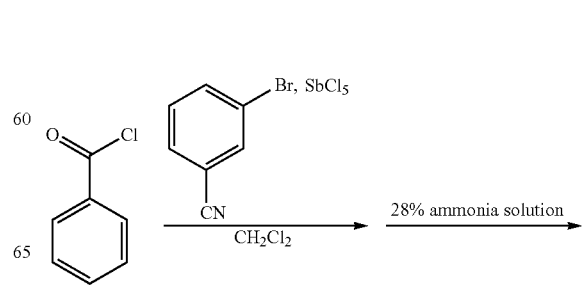

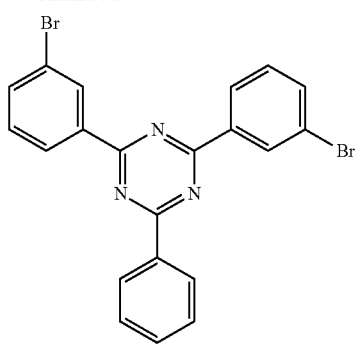

To a two-neck flask having been substituted with nitrogen, benzoyl chloride (11.0 mmol, 1.55 g), 3-bromobenzonitrile (22.0 mmol, 4.01 g) and 15 mL of methylene chloride were added, and stirred under cooling (0 to 5° C.) over an ice bath for 30 minutes. Antimony chloride (11.0 mmol, 3.30 g) was added dropwise thereto, and then the mixture was stirred at room temperature for 1 hour. Thereafter, the mixture was heated under refluxing for 12 hours. After standing to cool to room temperature, the yellow solid matter thus deposited was collected by filtering under suction, washed with methylene chloride, and then dried in vacuum. The resulting yellow solid matter was added to 75 mL of 28% aqueous ammonia cooled (0 to 5° C.) over an ice bath, and the mixture was stirred for 30 minutes. Thereafter, the mixture was stirred at room temperature for 3 hours. The white solid matter thus deposited was collected by filtering under suction, washed with water, and then dried in vacuum. The resulting white solid matter was added to 30 mL of N,N-dimethylformamide having been heated to 155° C., the mixture was stirred for 10 minutes, and the insoluble solid matter was filtered off under suction. The operation was repeated twice for purifying the product. Thereafter, N,N'-dimethylformamide was distilled off under heating and reduced pressure, thereby providing 2,4-bis(3-bromophenyl)-6-phenyl-1,5-triazine as the target product (yield amount: 2.67 g, yield: 51.9%).

(2) Synthesis of Compound 5

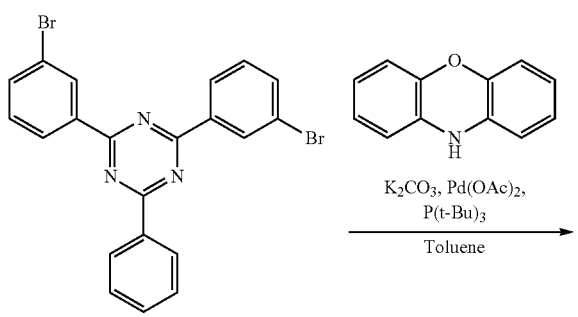

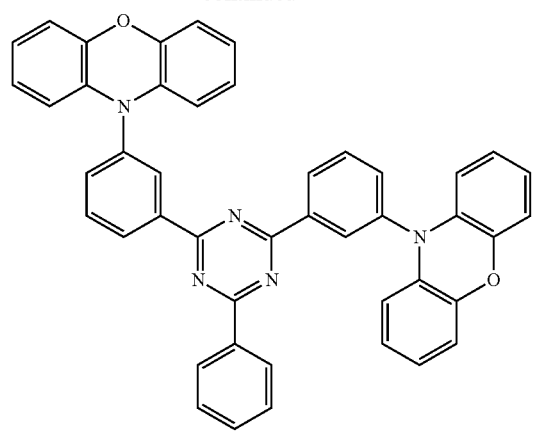

Compound 5

To a two-neck flask having been substituted with nitrogen, 2,4-bis(3-bromophenyl)-6-phenyl-1,3,5-triazine (3.00 mmol, 1.40 g), phenoxazine (6.60 mmol, 1.22 g), potassium carbonate (19.8 mmol, 2.74 g) and 55 mL of toluene were added, and stirred under room temperature for 10 minutes. A mixed solution of palladium(II) acetate (0.20 mmol, 45.0 mg), tri-tert-butylphosphine (0.73 mmol, 147.7 mg) and 55 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off under heating and reduced pressure. The resulting solid matter was washed with chloroform, thereby providing 2,4-bis(3-N-phenoxazylphenyl)-6-phenyl-1,3,5-triazine as the target product (yield amount: 1.55 g, yield: 76.7%).

$^1$H-NMR (CDCl$_3$, 300 MHz) δ=5.95 (d, 4H), 6.58 (t, 4H), 6.66 (t, 4H), 6.71 (d, 4H), 7.55 (m, 5H), 7.81 (t, 2H), 8.75 (s, 2H), 8.75 (d, 2H), 8.87 (d, 2H)

MS MALDI-MS m/z: 671

Synthesis Example 6

(1) Synthesis of 2,4,6-tri(3-bromophenyl)-1,3,5-triazine

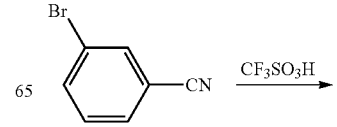

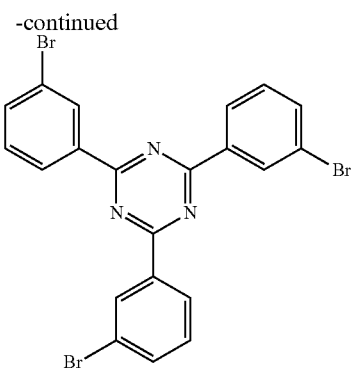

To a two-neck flask having been substituted with nitrogen, trifluoromethanesulfonic acid (66.6 mmol, 9.99 g) was added, and cooled (0 to 5° C.) over an ice bath. 3-Bromobenzonitrile (19.6 mmol, 3.57 g) was added thereto, and the mixture was stirred for 30 minutes. Thereafter, the mixture was stirred at room temperature for 12 hours. Water was added to the mixture, which was then neutralized with NaOH, and then washed with a mixed solvent of chloroform and acetone (50/50), and the organic layer was extracted. The organic layer was dehydrated over anhydrous magnesium sulfate, and the solvent was distilled off, thereby providing 2,4,6-tri(3-bromophenyl)-1,3,5-triazine as the target product (yield amount: 3.32 g, yield: 93.0%).

(2) Synthesis of Compound 6

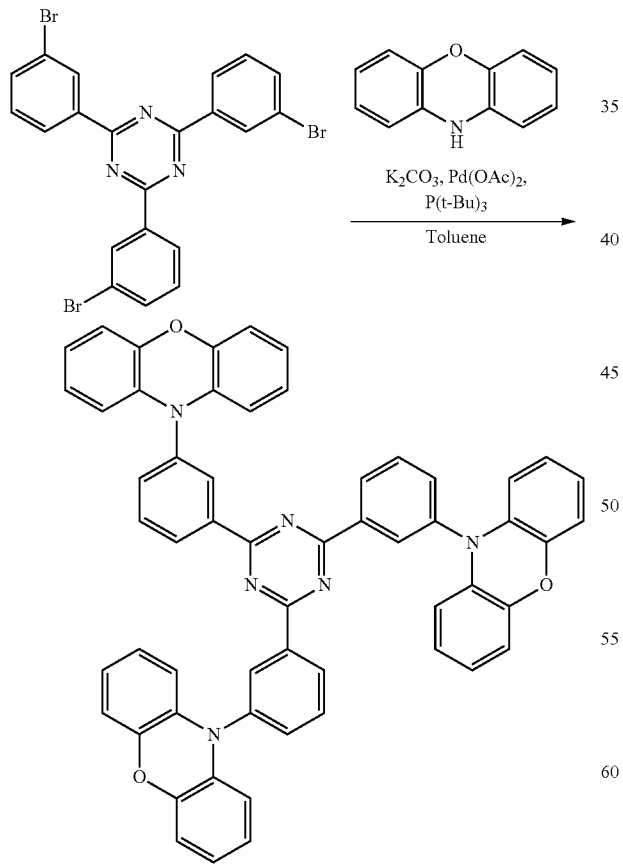

Compound 6

To a two-neck flask having been substituted with nitrogen, 2,4,6-tri(3-bromophenyl)-1,3,5-triazine (2.00 mmol, 1.09 g), phenoxazine (6.60 mmol, 1.22 g), potassium carbonate (19.8 mmol, 2.74 g) and 60 mL of toluene were added, and stirred under room temperature for 10 minutes. A mixed solution of palladium(II) acetate (0.20 mmol, 45.0 mg), tri-tert-butylphosphine (0.73 mmol, 147.7 mg) and 60 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off under heating and reduced pressure. The resulting solid matter was washed with chloroform, thereby providing 2,4,6-tri(3-N-phenoxazylphenyl)-1,3,5-triazine as the target product (yield amount: 1.63 g, yield: 95.30).

$^1$H-NMR (CDCl$_3$, 300 MHz) δ=5.91 (d, 6H), 6.52 (t, 6H), 6.63 (t, 6H), 6.68 (d, 6H), 7.57 (d, 3H), 7.78 (t, 3H), 8.75 (s, 3H), 8.85 (d, 3H)

MS MALDI-MS m/z: 852

Synthesis Example 7

Synthesis of Compound 7

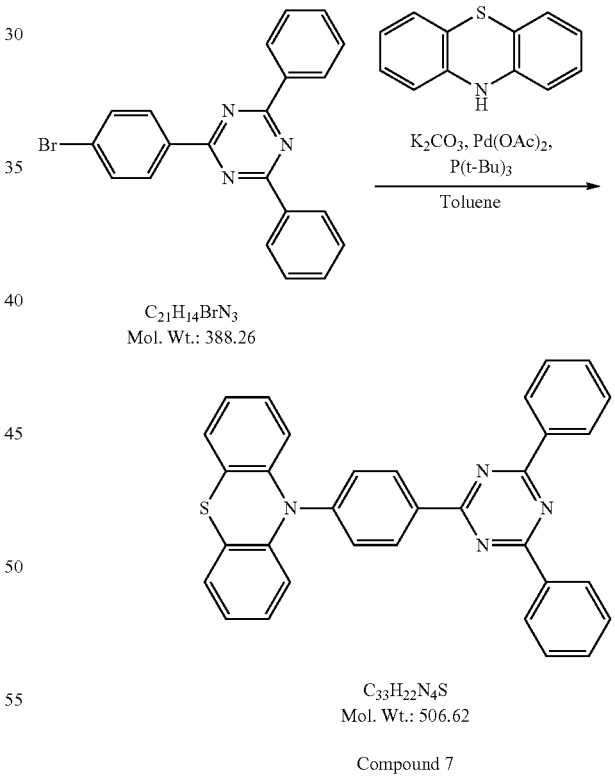

Compound 7

To a two-neck flask having been substituted with nitrogen, 2-(4-bromophenyl)-4,6-diphenyl-1,3,5-triazine (3.0 mmol, 1.17 g), phenothiazine (3.3 mmol, 657.6 mg), potassium carbonate (9.0 mmol, 1.24 g) and 30 mL of toluene were added, and stirred under room temperature for 10 minutes. A mixed solution of palladium(II) acetate (0.09 mmol, 20.2 mg), tri-tert-butylphosphine (0.33 mmol, 66.8 mg) and 30 mL of toluene was added thereto, and the mixture was heated under refluxing for 24 hours. After standing to cool to room temperature, chloroform and a sodium chloride aqueous solution were added thereto, and the organic layer was separated and extracted. The organic layer was dehydrated over anhydrous magnesium sulfate, and the solvent was distilled off. The compound 7 as the target product was isolated and purified by silica gel chromatography with a mixed solvent of chloroform and hexane (1/4) (yield amount: 1.03 g, yield: 68%).

$^1$H-NMR (CDCl$_3$, 300 MHz) δ=6.72 (d, 2H), 6.95 (t, 2H), 7.02 (t, 2H), 7.19 (d, 2H), 7.46 (d, 2H), 7.56 (m, 6H), 8.77 (d, 4H), 8.86 (d, 2H)

MALDI-MS m/z: 506

Synthesis Example 8

Synthesis of Compound 13

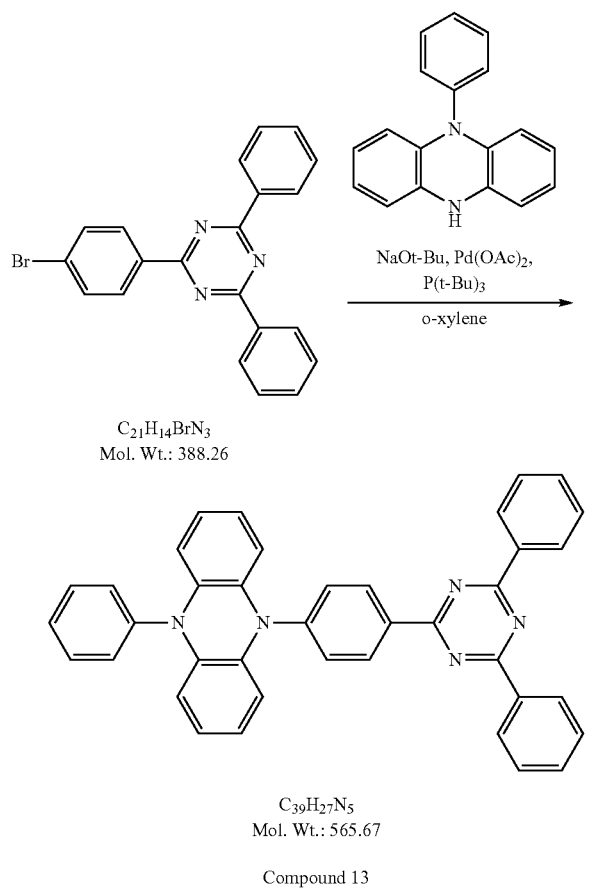

C$_{39}$H$_{27}$N$_5$
Mol. Wt.: 565.67

Compound 13

To a two-neck flask having been substituted with nitrogen, 2-(4-bromophenyl)-4,6-diphenyl-1,3,5-triazine (2.57 mmol, 1.0 g), 5-hydro-10-phenylphenazine (4.0 mmol), sodium tert-butoxide (3.87 mmol, 371.9 mg) and 15 mL of o-xylene were added, and stirred under room temperature for 10 minutes. A mixed solution of palladium(II) acetate (0.16 mmol, 35 mg), tri-tert-butylphosphine (0.49 mmol, 100 mg) and 15 mL of o-xylene was added thereto, and the mixture was heated under refluxing overnight. After standing to cool to room temperature, chloroform and a sodium chloride aqueous solution were added thereto, and the organic layer was separated and extracted. The organic layer was dehydrated over anhydrous magnesium sulfate, and the solvent was distilled off. The compound 13 as the target product was isolated and purified by silica gel chromatography with a mixed solvent of chloroform and hexane (1/4) (yield amount: 654.2 mg, yield: 45%).

$^1$H-NMR (CDCl$_3$, 300 MHz) δ=7.59 (m, 17H), 8.81 (d, 10H)

MALDI-MS m/z: 566

Synthesis Example 9

Synthesis of Compound 19

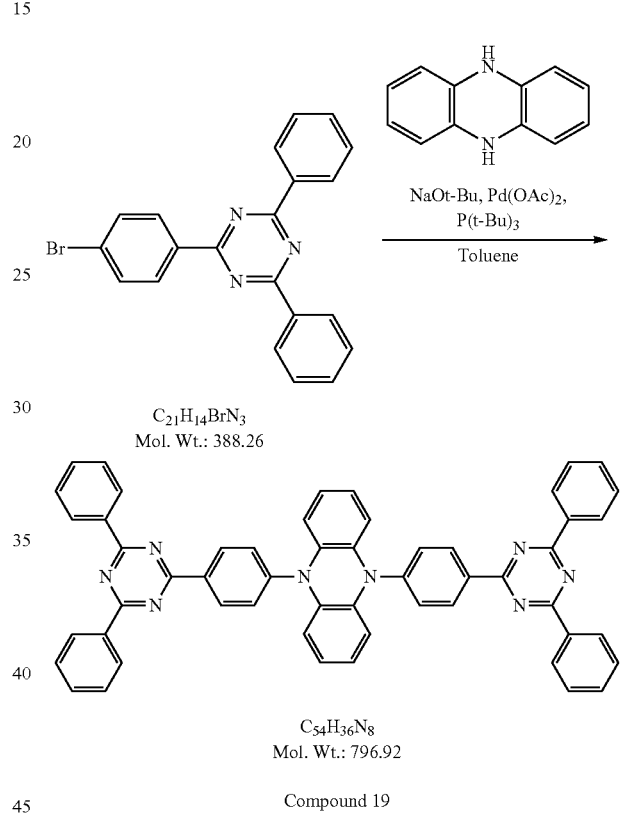

C$_{54}$H$_{36}$N$_8$
Mol. Wt.: 796.92

Compound 19

To a two-neck flask having been substituted with nitrogen, 2-(4-bromophenyl)-4,6-diphenyl-1,3,5-triazine (1.0 mmol, 388.3 mg), 5,10-dihydrophenazine (0.5 mmol, 91.1 mg), sodium tert-butoxide (1.5 mmol, 144.2 mg) and 5 mL of toluene were added, and stirred under room temperature for 10 minutes. A mixed solution of palladium(II) acetate (0.04 mmol, 4.5 mg), tri-tert-butylphosphine (0.11 mmol, 11.2 mg) and 5 mL of toluene was added thereto, and the mixture was heated under refluxing overnight. After standing to cool to room temperature, chloroform and a sodium chloride aqueous solution were added thereto, and the organic layer was separated and extracted. The organic layer was dehydrated over anhydrous magnesium sulfate, and the solvent was distilled off. The compound 19 as the target product was isolated and purified by silica gel chromatography with a mixed solvent of chloroform and hexane (1/4) (yield amount: 446.3 mg, yield: 560).

$^1$H-NMR (CDCl$_3$, 300 MHz) δ=7.58 (m, 20H), 8.79 (d, 16H)

MALDI-MS m/z: 796

Example 1

Production and Evaluation of Organic Photoluminescent Device (Solution)

Figure 2:
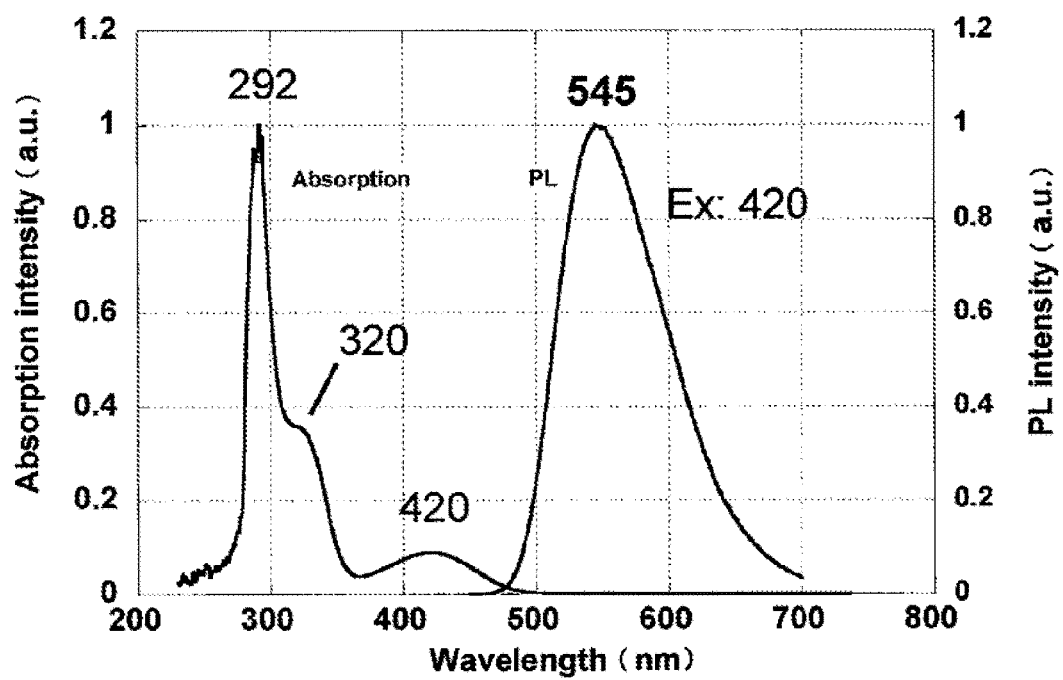
FIG. 2 is a light emission spectrum of a toluene solution of a compound 1 of Example 1.
Figure 3:
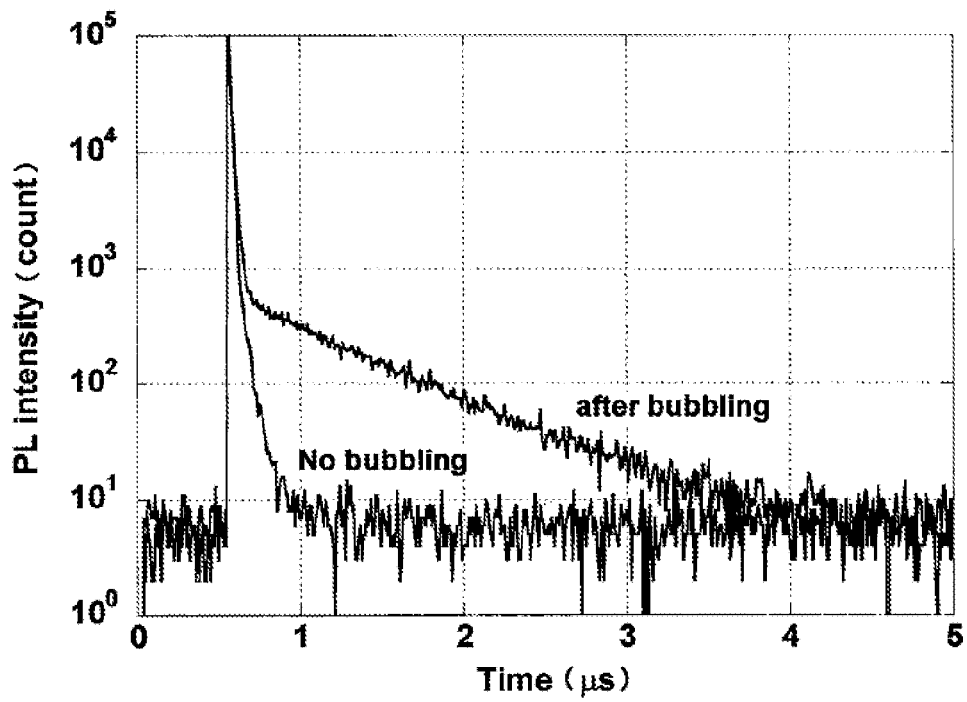
FIG. 3 is a time resolved spectrum of a toluene solution of a compound 1 of Example 1.

A toluene solution of the compound 1 synthesized in Synthesis Example 1 (concentration: $10^{-4}$ mol/L) was prepared and irradiated with ultraviolet light at 300 K under bubbling with nitrogen, and thus fluorescent light having a peak wavelength of 545 nm was observed as shown in FIG. 2. The solution was observed with a compact fluorescence lifetime spectrometer (Quantaurus-tau, produced by Hamamatsu Photonics K.K.) before and after bubbling with nitrogen, thereby providing the time resolved spectrum shown in FIG. 3. Fluorescent light having an excitation lifetime of 0.019 μs and delayed fluorescent light having an excitation lifetime of 0.676 μs were observed. The photoluminescent quantum efficiency of the compound 1 in the toluene solution was measured at 300 K with an absolute PL quantum yields measurement system (Quantaurus-QY, produced by Hamamatsu Photonics K.K.), and was 14.5% before bubbling with nitrogen and 29.5% after bubbling with nitrogen.

Figure 4:
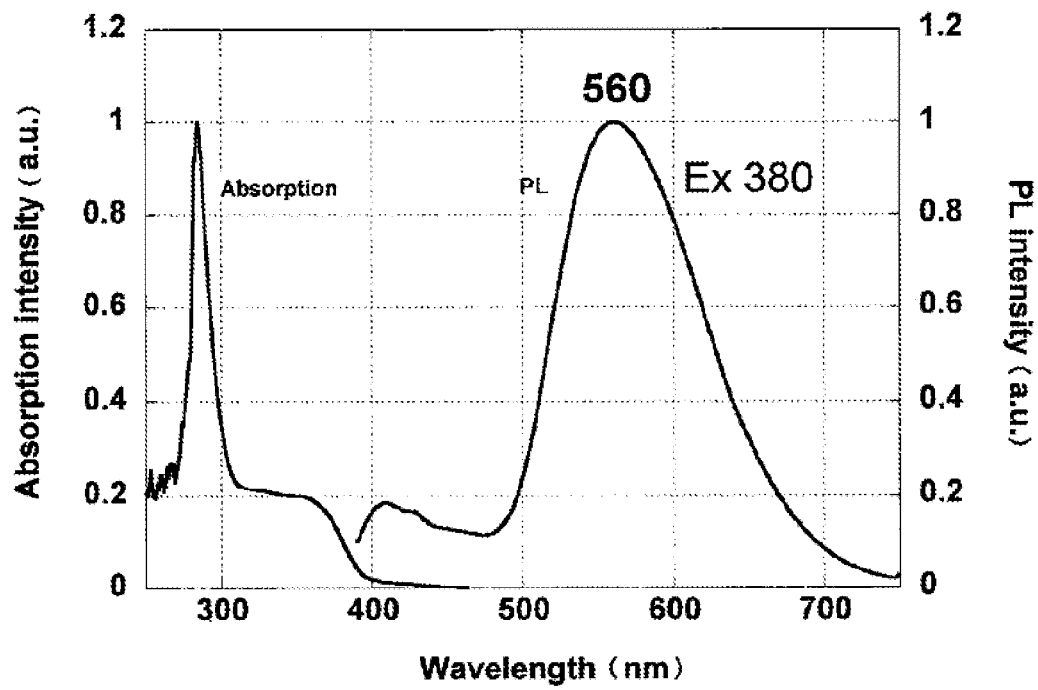
FIG. 4 is a light emission spectrum of a toluene solution of a compound 7 of Example 1.
Figure 5:
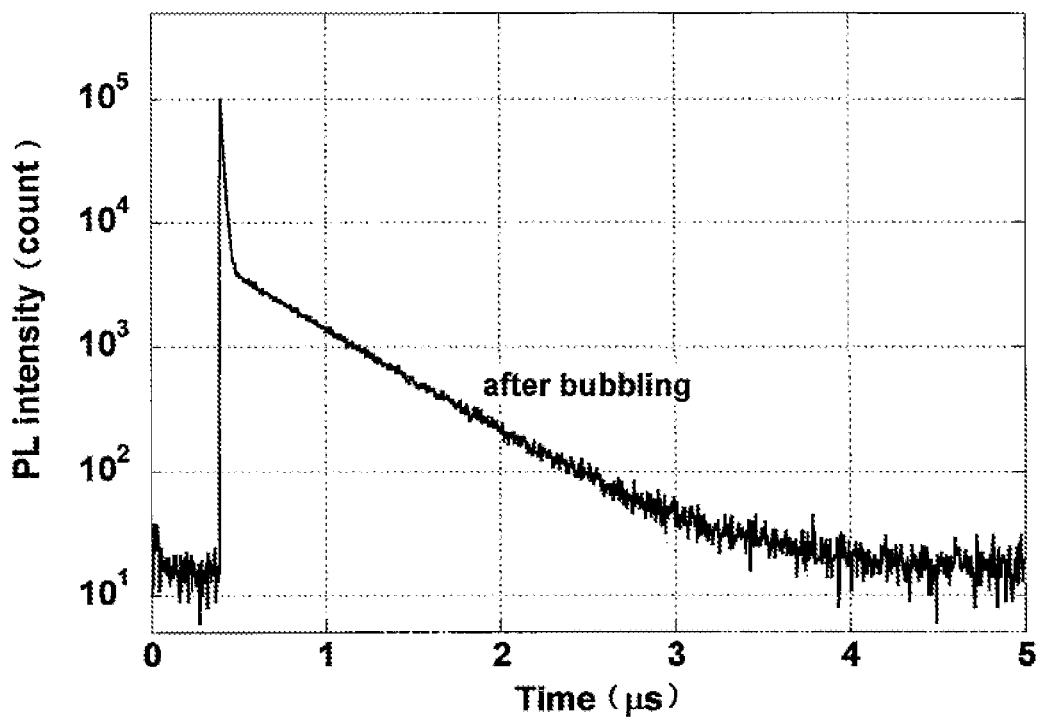
FIG. 5 is a time resolved spectrum of a toluene solution of a compound 7 of Example 1.

The production and evaluation of a toluene solution were performed in the same manner by using the compound 7 synthesized in Synthesis Example 7 instead of the compound 1. FIG. 4 shows the light emission spectrum, and FIG. 5 shows the time resolved spectrum after bubbling with nitrogen. Fluorescent light having an excitation lifetime of 0.016 μs and delayed fluorescent light having an excitation lifetime of 0.527 μs were observed. The photoluminescent quantum efficiency was 7.4% before bubbling with nitrogen and 21.8% after bubbling with nitrogen.

For the compound 2 synthesized in Synthesis Example 2, the compound 3 synthesized in Synthesis Example 3, the compound 4 synthesized in Synthesis Example 4, the compound 13 synthesized in Synthesis Example 8 and the compound 19 synthesized in Synthesis Example 9, light emission in the visible region was observed similarly. The photoluminescent quantum efficiency of the compound 2 was 14.1% before bubbling with nitrogen and 28.8% after bubbling with nitrogen. The photoluminescent quantum efficiency of the compound 3 was 12.6% before bubbling with nitrogen and 23.1% after bubbling with nitrogen. The photoluminescent quantum efficiency of the compound 4 was 1.6% before bubbling with nitrogen and 5.2% after bubbling with nitrogen.

Example 2

Production and Evaluation of Organic Photoluminescent Device (Thin Film)

Figure 6:
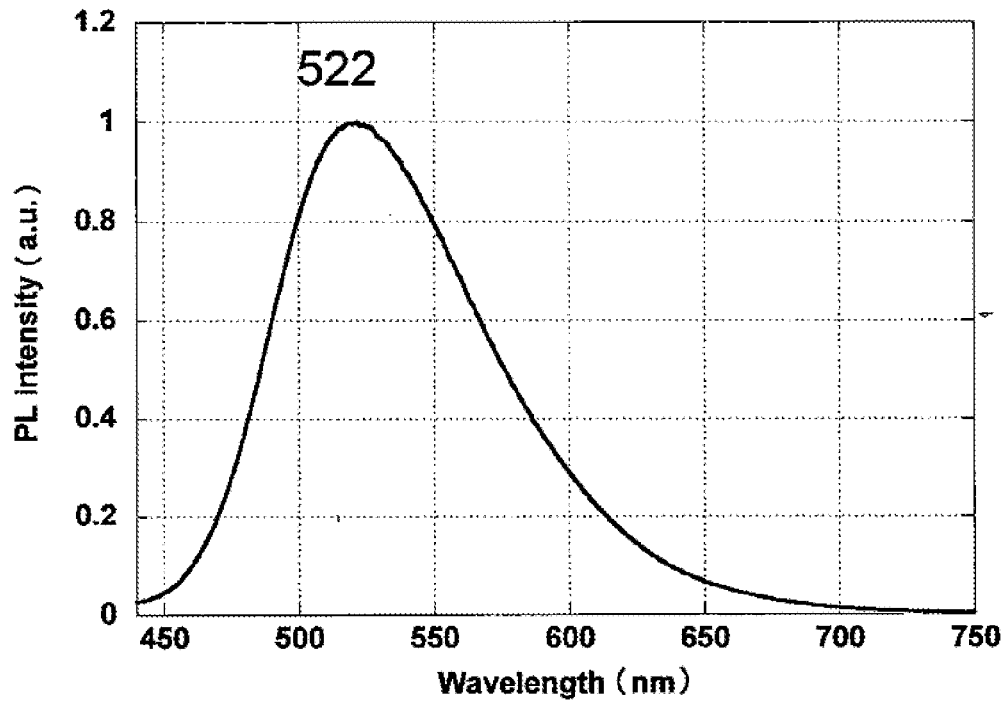
FIG. 6 is a light emission spectrum of a thin film organic photoluminescent device using a compound 1 of Example 2.
Figure 7:
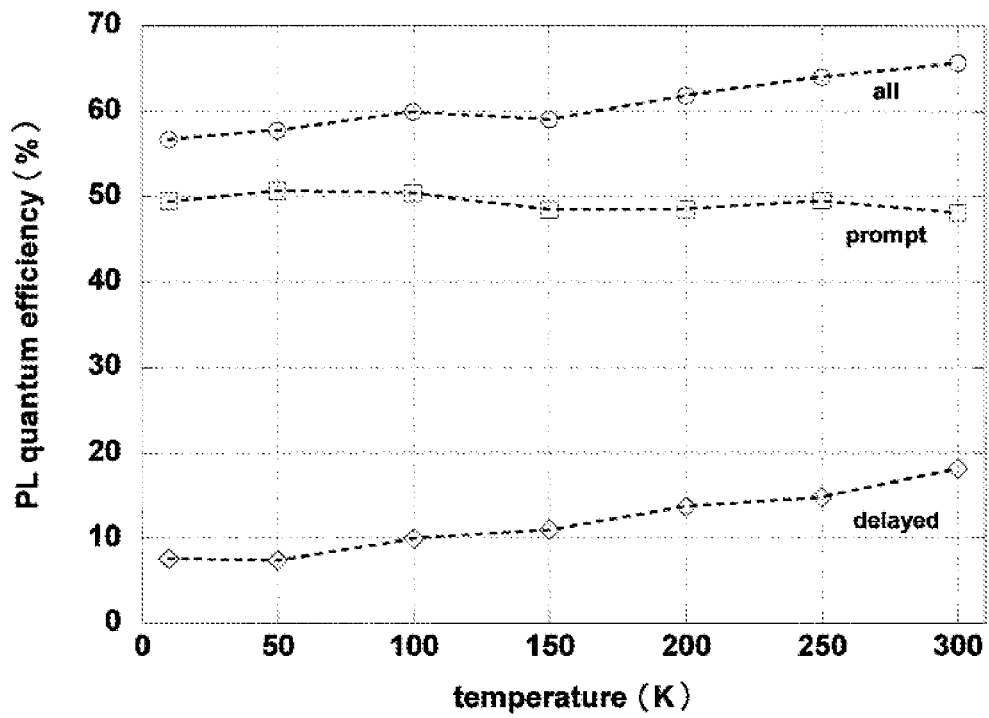
FIG. 7 is a graph showing changes of quantum efficiency of fluorescent components of a thin film organic photoluminescent device using a compound 1 of Example 2 depending on the temperature.

On a silicon substrate, the compound 1 and CBP were vapor-deposited from separate vapor deposition sources respectively by a vacuum vapor deposition method under condition of a vacuum degree of $5.0\times10^{-4}$ Pa, thereby forming a thin film having a thickness of 100 nm and a concentration of the compound 1 of 6.0% by weight at a rate of 0.3 nm/min, which was designated as an organic photoluminescent device. FIG. 6 shows the light emission spectrum of the device measured with the same measuring equipment as in Example 1. The photoluminescent quantum efficiency at 300 K was 65.7%. Time resolved spectra were obtained at temperatures of 20 K, 50 K, 100 K, 150 K, 200 K, 250 K and 300 K, and the temperature dependency of the quantum efficiency was evaluated for the component with a short light emission lifetime and the component with a long light emission lifetime (FIG. 7). As a result, it was confirmed that the compound 1 was a thermal activation type delayed fluorescent material.

Figure 8:
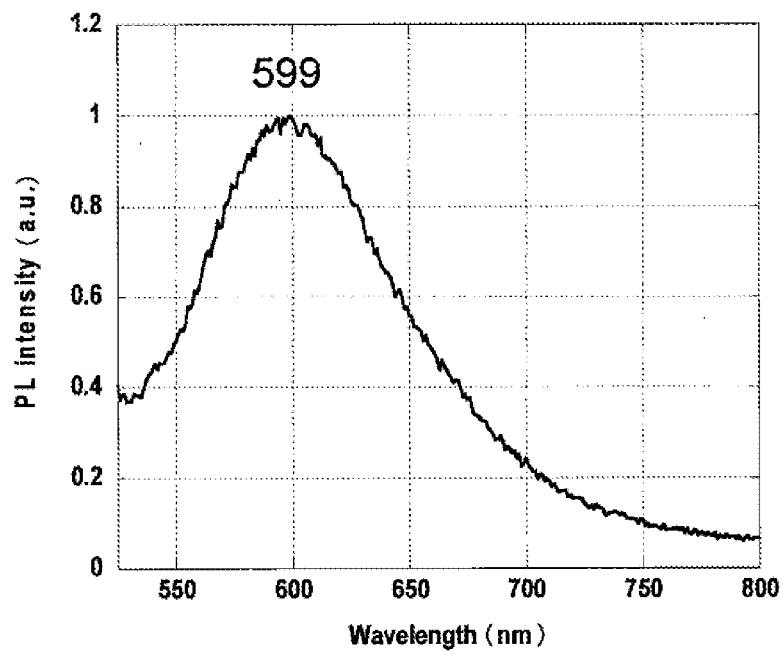
FIG. 8 is a light emission spectrum of a thin film organic photoluminescent device using a compound 13 of Example 2.

Organic photoluminescent devices were produced by using the compound 2, the compound 3, the compound 4, the compound 5, the compound 7, the compound 13 and the compound 19 instead of the compound 1, and light emission was confirmed with the devices. FIG. 8 shows the light emission spectrum of the organic photoluminescent device using the compound 13. The photoluminescent quantum efficiency of the photoluminescent device having a compound concentration of 2.0% by weight was 69% for the compound 2, 69% for the compound 3, 32% for the compound 4 and 22% for the compound 5.

Example 3

Production and Evaluation of Organic Electroluminescent Device

Thin films each were formed by a vacuum vapor deposition method at a vacuum degree of $5.0\times10^{-4}$ Pa on a glass substrate having formed thereon an anode formed of indium tin oxide (ITO) having a thickness of 100 nm. First, α-NPD was formed to a thickness of 35 nm on ITO. The compound 1 and CBP were then vapor-deposited from separate vapor deposition sources respectively to form a layer having a thickness of 15 nm, which was designated as a light-emitting layer. The concentration of the compound 1 herein was 6.0% by weight. TPBi was then formed to a thickness of 65 nm, lithium fluoride (LiF) was further vapor-deposited to a thickness of 0.8 nm, and then aluminum (Al) was vapor-deposited to a thickness of 80 nm, which was designated as a cathode, thereby completing an organic electroluminescent device.

Figure 9:
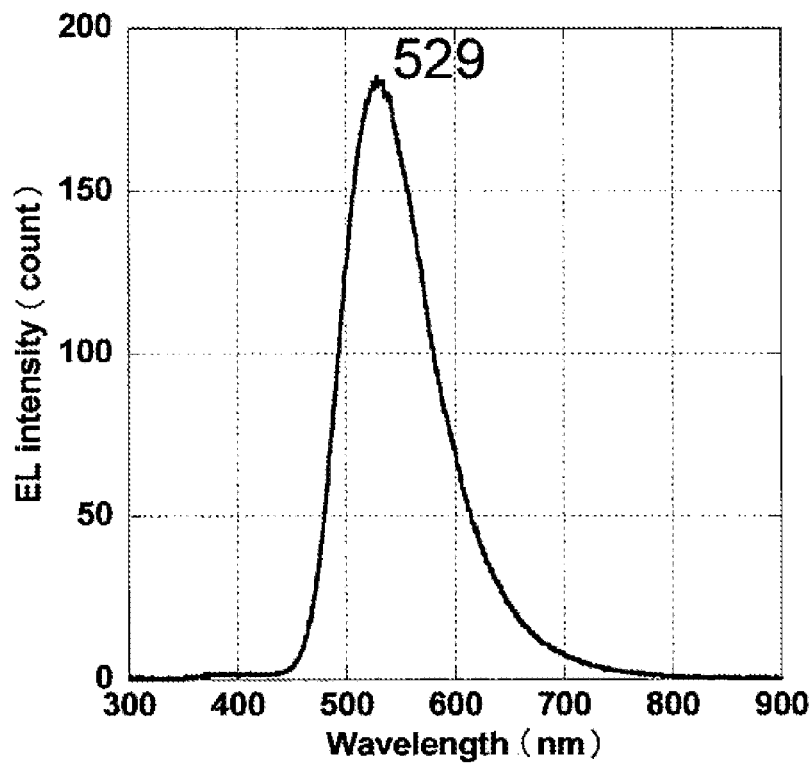
FIG. 9 is a light emission spectrum of an organic electroluminescent device using a compound 1 of Example 3.
Figure 10:
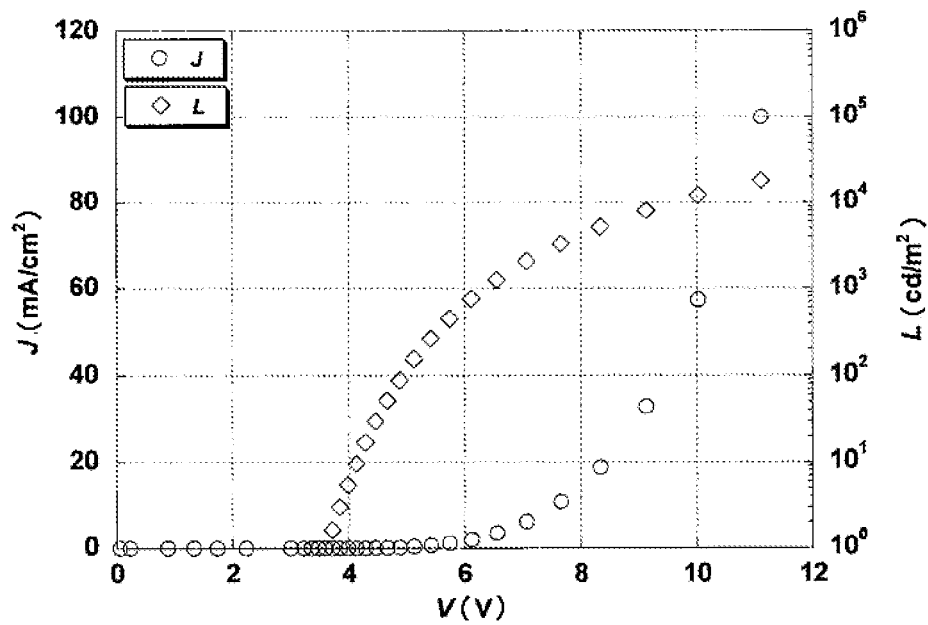
FIG. 10 is a graph showing electric current density-voltage-luminance characteristics of an organic electroluminescent device using a compound 1 of Example 3.
Figure 11:
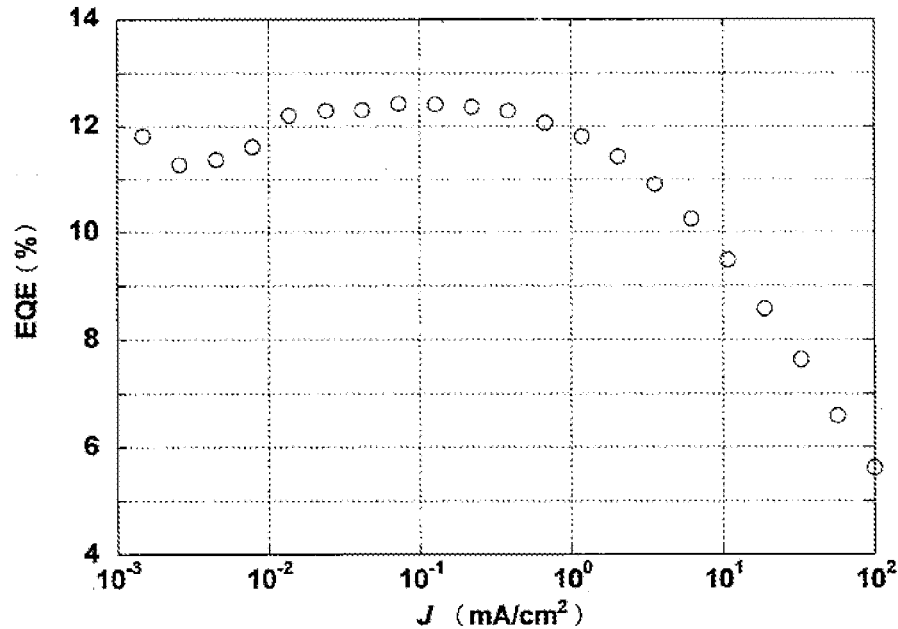
FIG. 11 is a graph showing external quantum efficiency-electric current density characteristics of an organic electroluminescent device using a compound 1 of Example 3.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.), and thus light emission was observed at 592 nm as shown in FIG. 9. FIG. 10 shows the electric current density-voltage-luminance characteristics of the device, and FIG. 11 shows the electric current density-external quantum efficiency characteristics of the device. The organic electroluminescent device using the compound 1 as a light-emitting material achieved a high external quantum efficiency of 12.5%.

Figure 12:
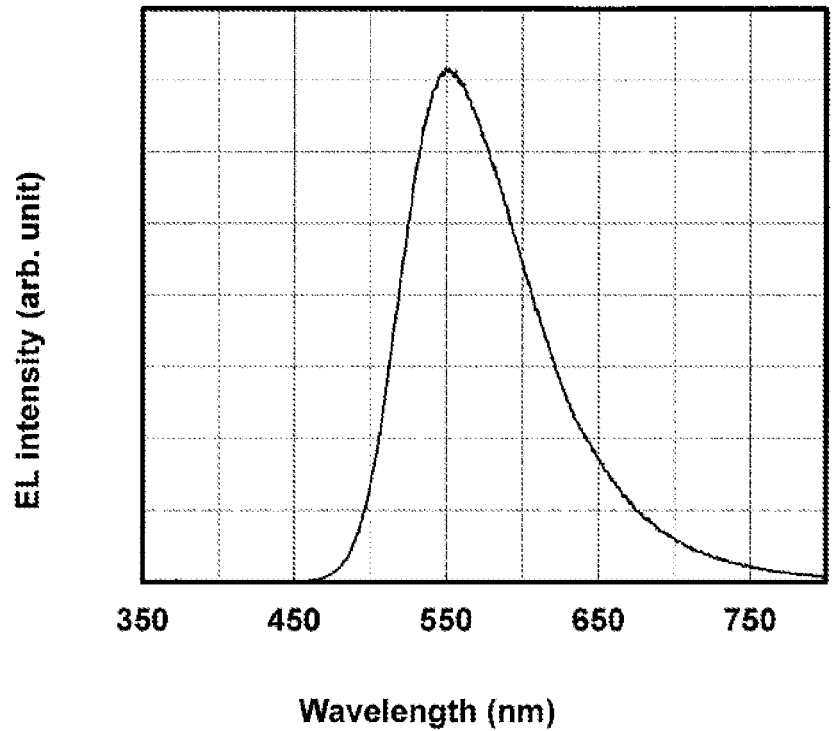
FIG. 12 is a light emission spectrum of an organic electroluminescent device using a compound 2 of Example 3.
Figure 13:
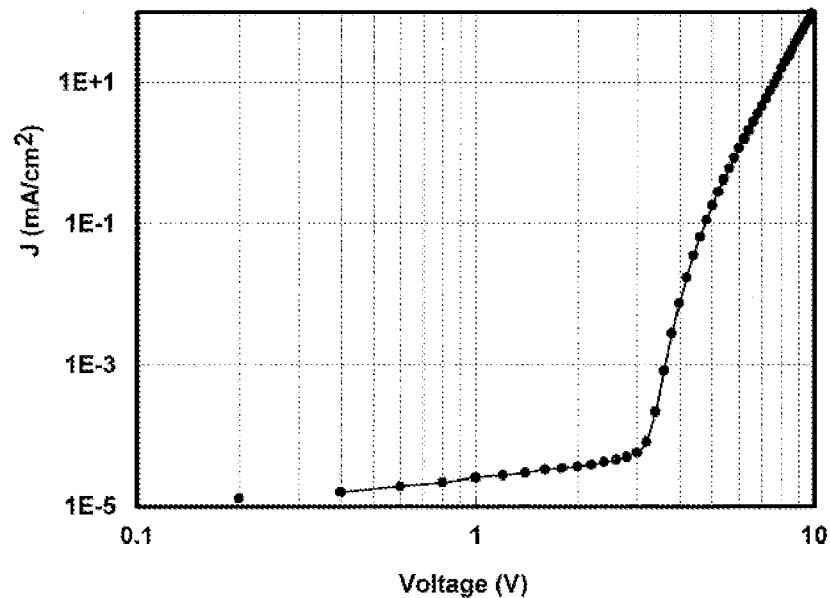
FIG. 13 is a graph showing electric current density-voltage characteristics of an organic electroluminescent device using a compound 2 of Example 3.
Figure 14:
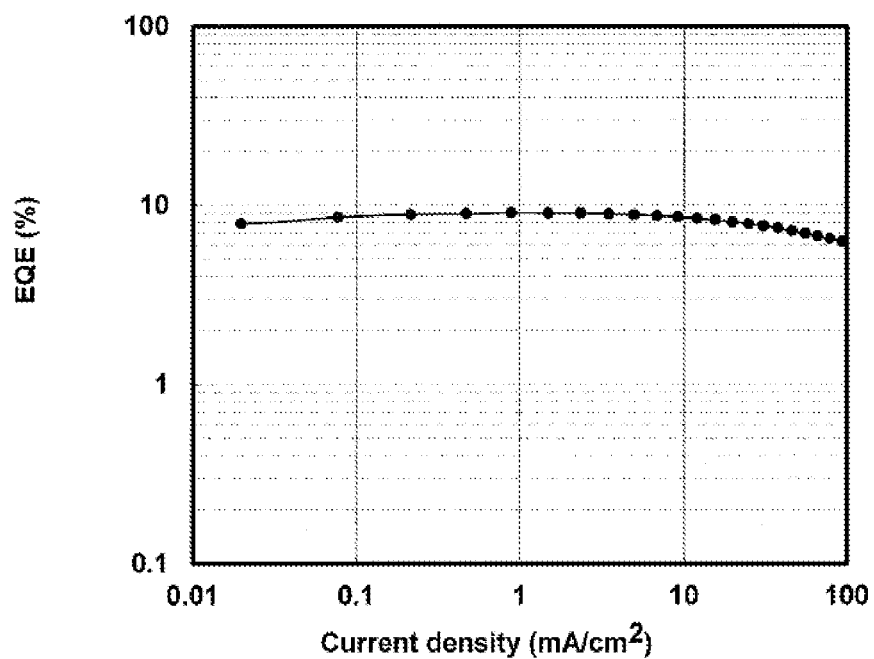
FIG. 14 is a graph showing external quantum efficiency-electric current density characteristics of an organic electroluminescent device using a compound 2 of Example 3.
Figure 15:
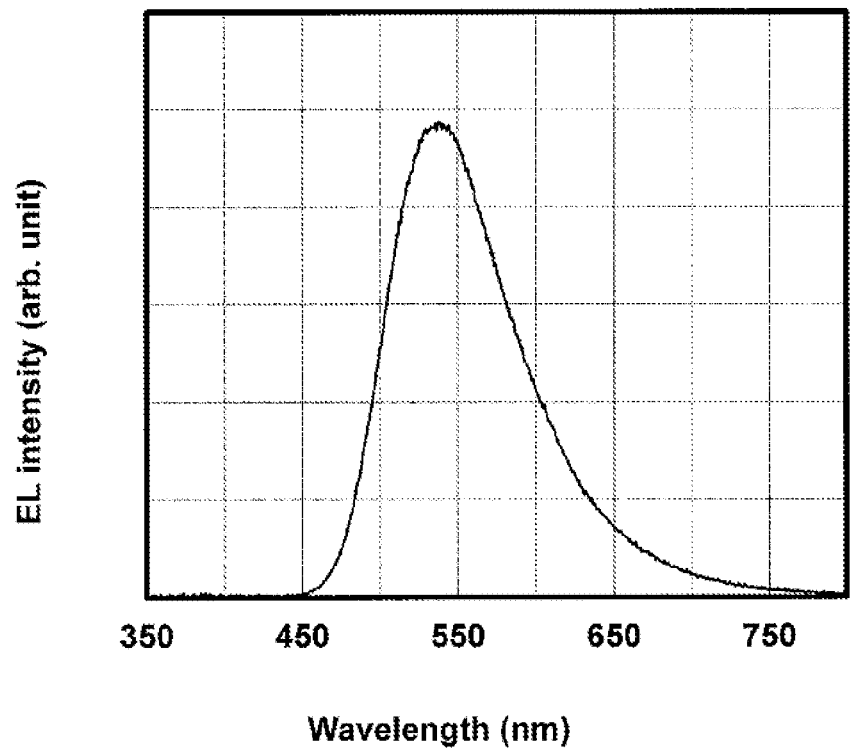
FIG. 15 is a light emission spectrum of another organic electroluminescent device using a compound 2 of Example 3.
Figure 16:
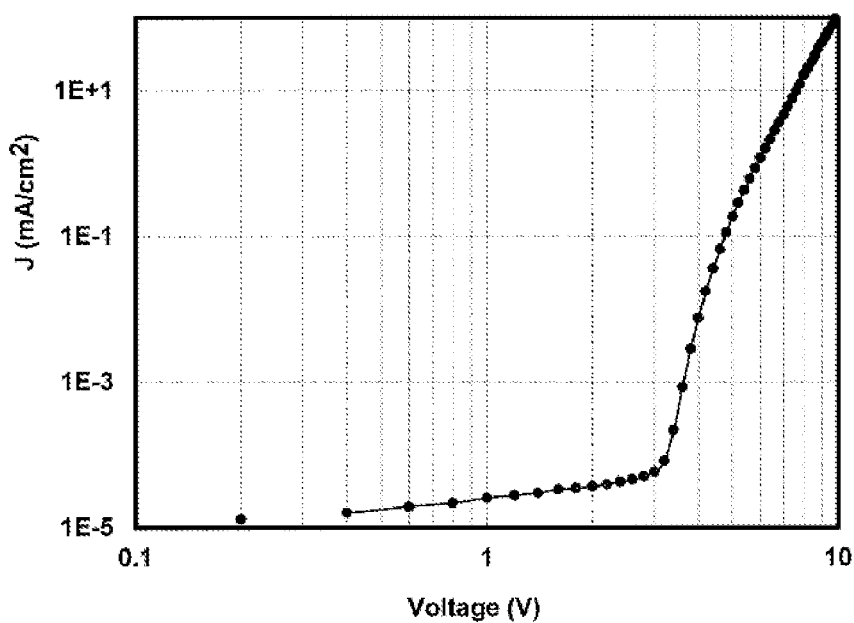
FIG. 16 is a graph showing electric current density-voltage characteristics of another organic electroluminescent device using a compound 2 of Example 3.
Figure 17:
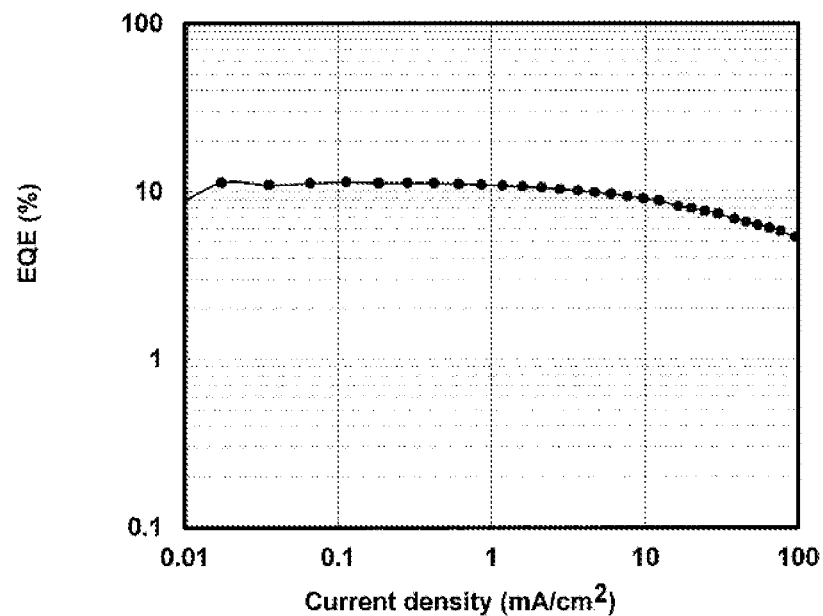
FIG. 17 is a graph showing external quantum efficiency-electric current density characteristics of another organic electroluminescent device using a compound 2 of Example 3.

FIG. 12 shows the light emission spectrum of an organic electroluminescent device produced by using the compound 2 instead of the compound 1 (the concentration of the compound 2 in the light-emitting layer is 6.0% by weight), FIG. 13 shows the electric current density-voltage characteristics of the device, and FIG. 14 shows the electric current density-external quantum efficiency characteristics of the device. An organic electroluminescent device was further produced by changing the concentration of the compound 2 in the light-emitting layer to 2.0% by weight. FIG. 15 shows the light emission spectrum of the device, FIG. 16 shows the electric current density-voltage characteristics of the device, and FIG. 17 shows the electric current density-external quantum efficiency characteristics of the device. The organic electroluminescent device using the compound 2 as a light-emitting material achieved a high external quantum efficiency of 11.0%.

Figure 18:
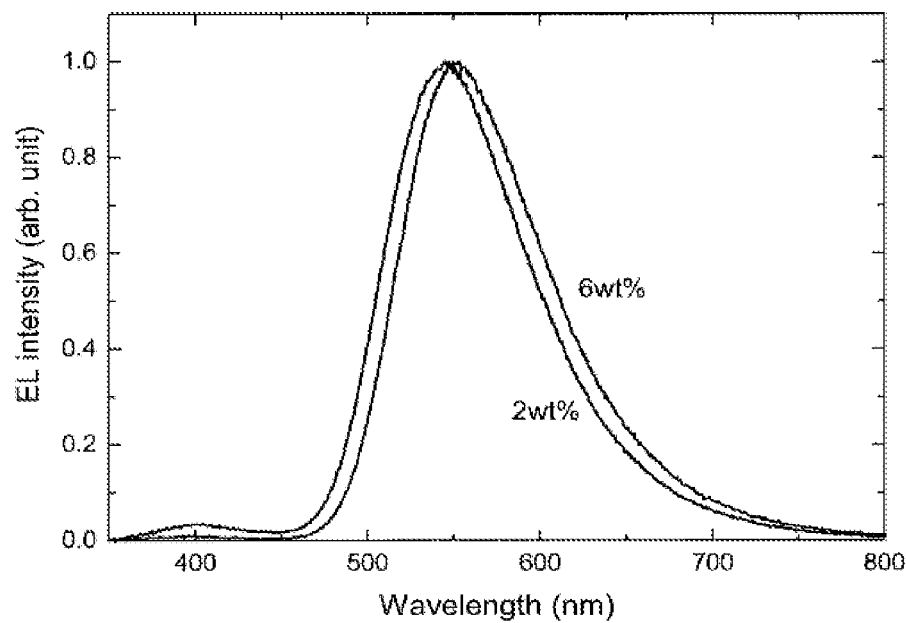
FIG. 18 is a light emission spectrum of an organic electroluminescent device using a compound 3 of Example 3.
Figure 19:
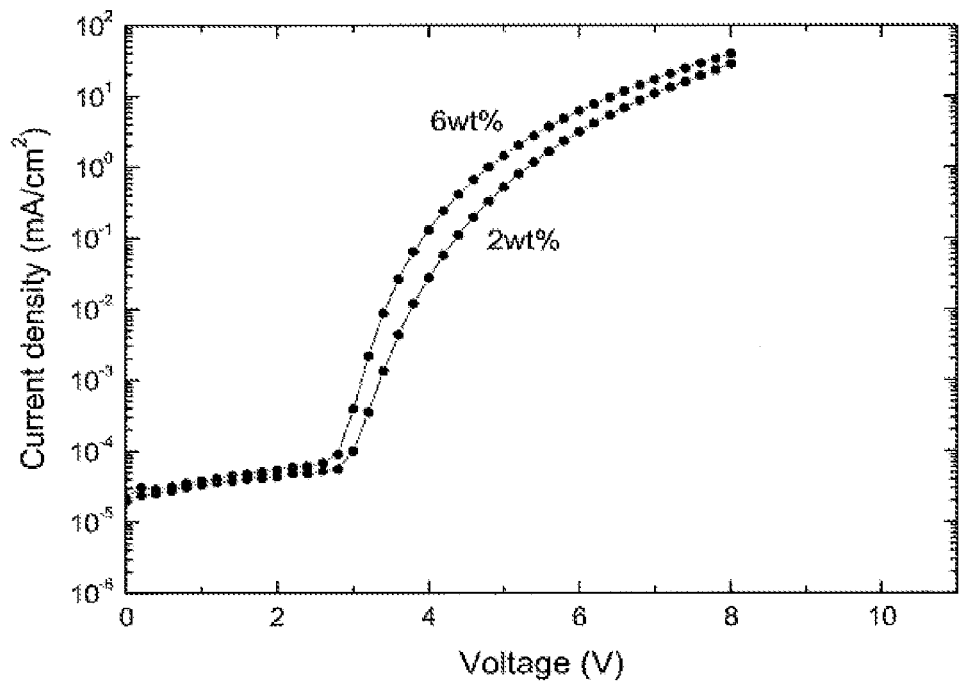
FIG. 19 is a graph showing electric current density-voltage characteristics of an organic electroluminescent device using a compound 3 of Example 3.
Figure 20:
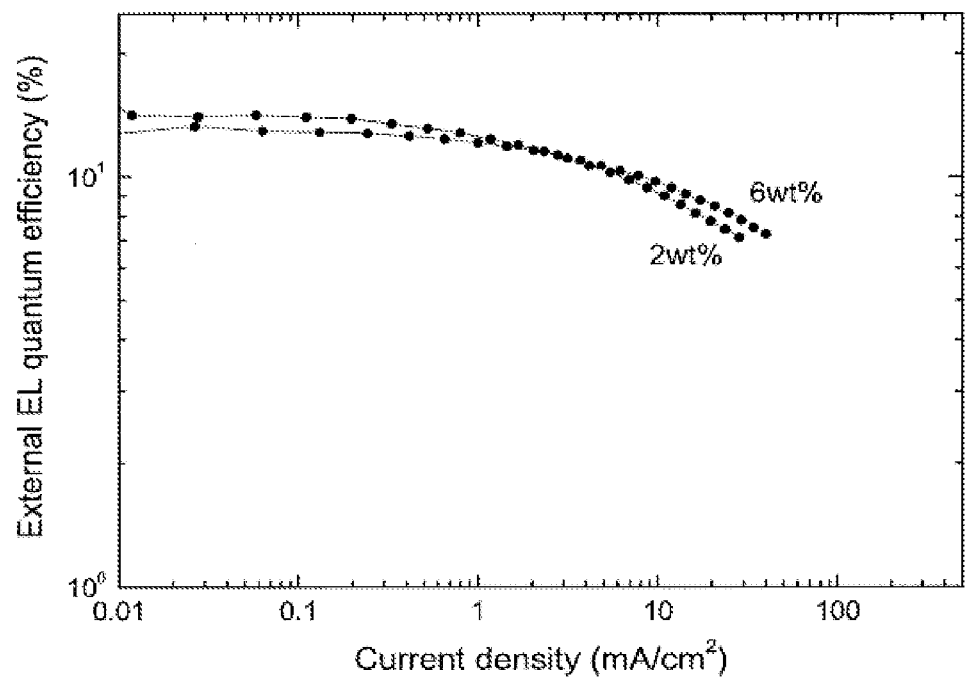
FIG. 20 is a graph showing external quantum efficiency-electric current density characteristics of an organic electroluminescent device using a compound 3 of Example 3.

By using the compound 3 instead of the compound 1, an organic electroluminescent device having a concentration of the compound 3 in the light-emitting layer of 2.0% by weight and an organic electroluminescent device having a concentration of the compound 3 in the light-emitting layer of 6.0% by weight were produced. FIG. 18 shows the light emission spectra of the devices, FIG. 19 shows the electric current density-voltage characteristics of the devices, and FIG. 20 shows the electric current density-external quantum efficiency characteristics of the devices. The organic electroluminescent device using the compound 3 as a light-emitting material achieved a high external quantum efficiency of 14.2%.

Figure 21:
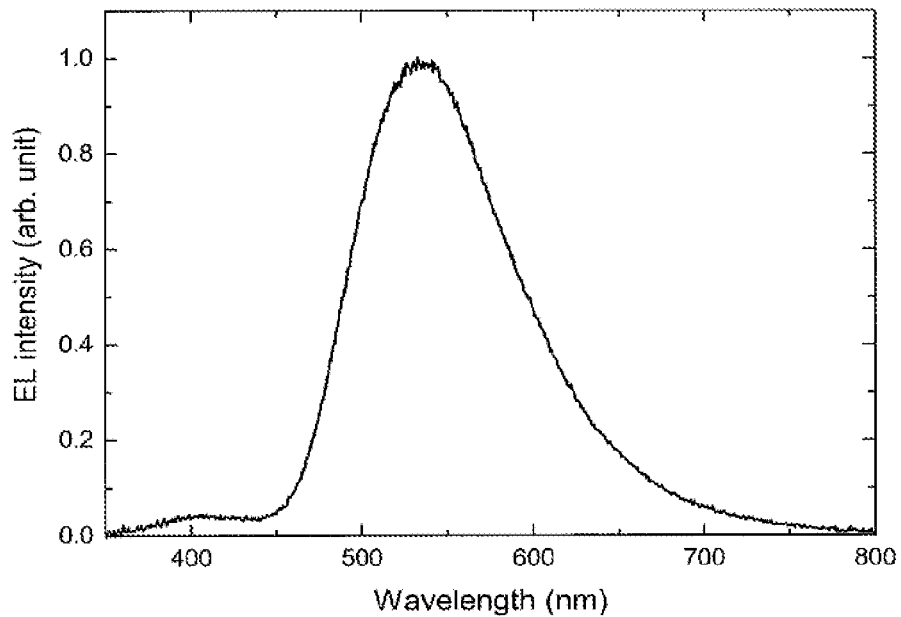
FIG. 21 is a light emission spectrum of an organic electroluminescent device using a compound 4 of Example 3.
Figure 22:
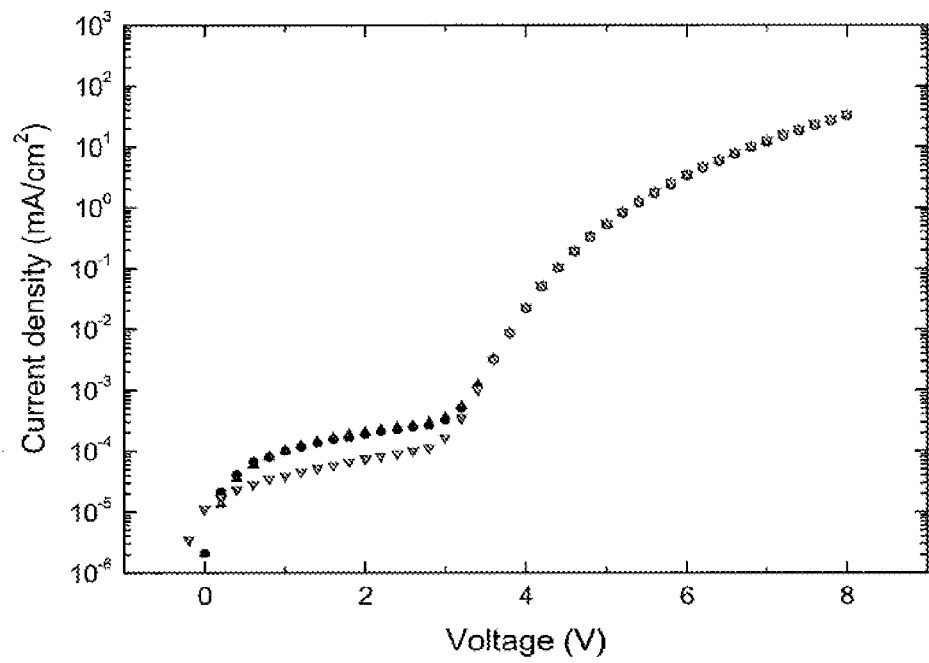
FIG. 22 is a graph showing electric current density-voltage characteristics of an organic electroluminescent device using a compound 4 of Example 3.
Figure 23:
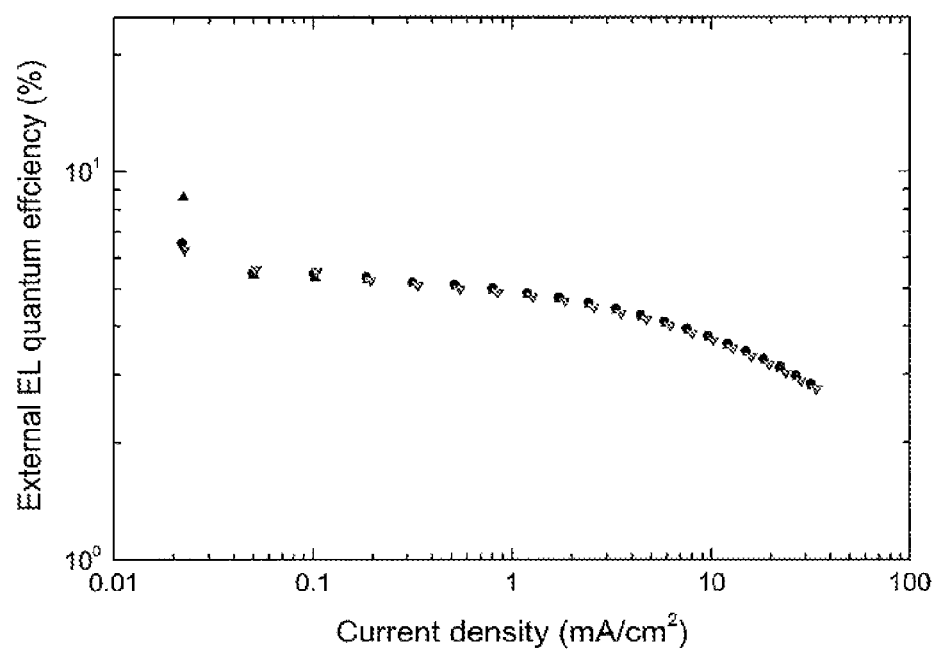
FIG. 23 is a graph showing external quantum efficiency-electric current density characteristics of an organic electroluminescent device using a compound 4 of Example 3.

By using the compound 4 instead of the compound 1, an organic electroluminescent device having a concentration of the compound 4 in the light-emitting layer of 2.0% by weight was produced. FIG. 21 shows the light emission spectrum of the device, FIG. 22 shows the electric current density-voltage characteristics of the device, and FIG. 23 shows the electric current density-external quantum efficiency characteristics of the device.

Figure 24:
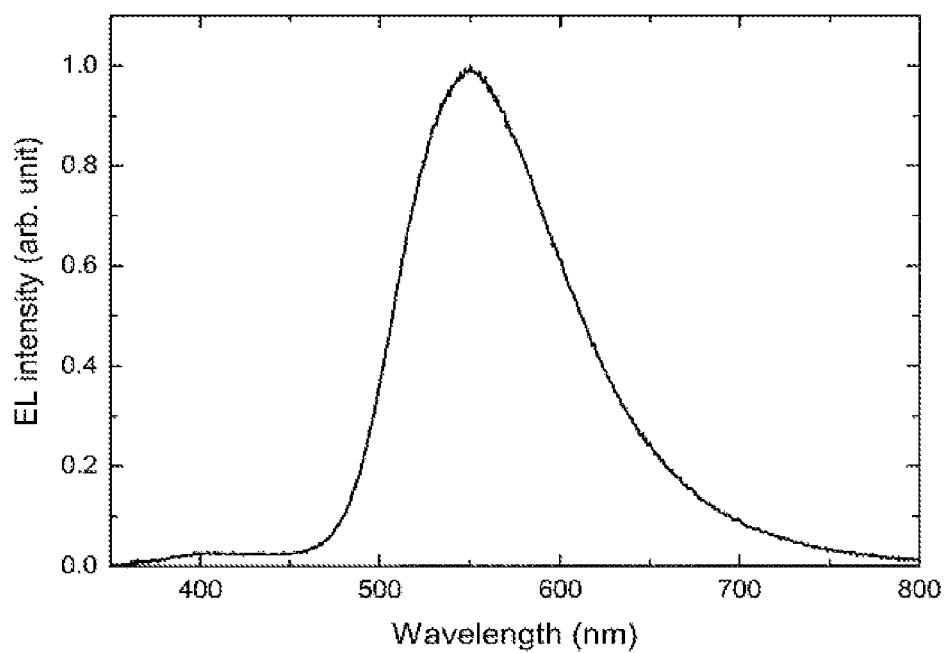
FIG. 24 is a light emission spectrum of an organic electroluminescent device using a compound 5 of Example 3.
Figure 25:
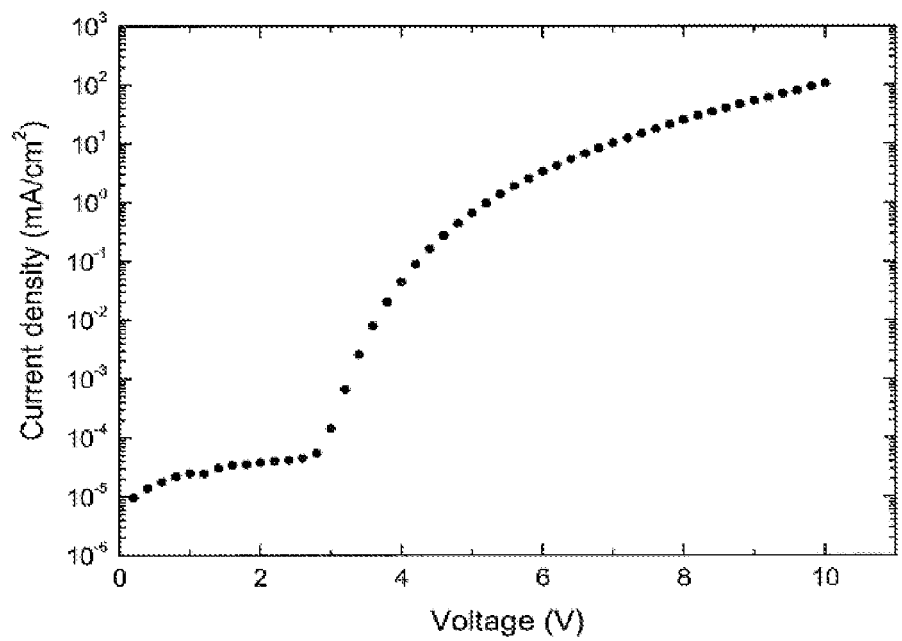
FIG. 25 is a graph showing electric current density-voltage characteristics of an organic electroluminescent device using a compound 5 of Example 3.
Figure 26:
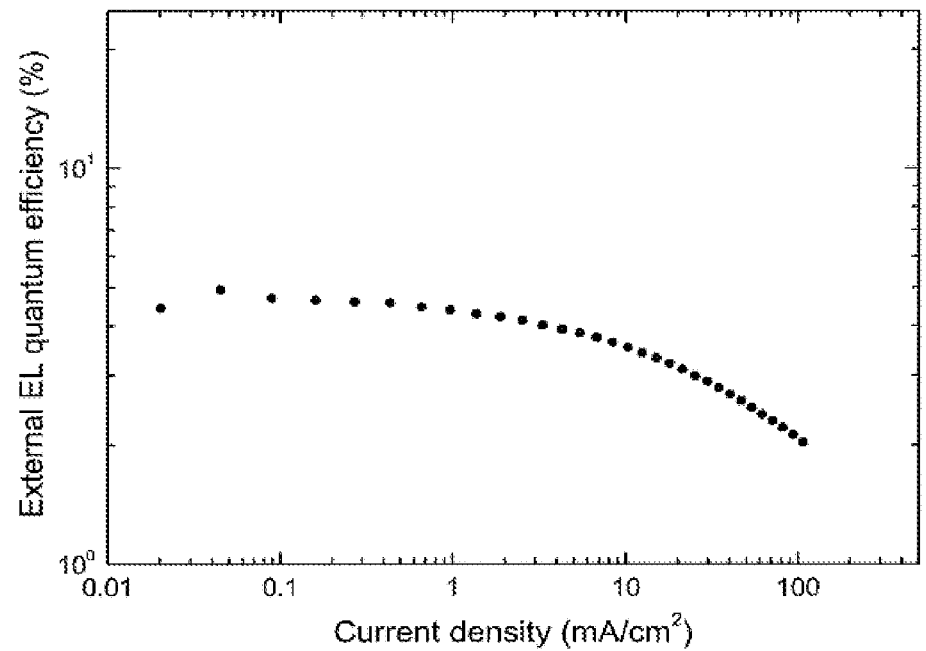
FIG. 26 is a graph showing external quantum efficiency-electric current density characteristics of an organic electroluminescent device using a compound 5 of Example 3.

By using the compound 5 instead of the compound 1, an organic electroluminescent device having a concentration of the compound 5 in the light-emitting layer of 2.0% by weight was produced. FIG. 24 shows the light emission spectrum of the device, FIG. 25 shows the electric current density-voltage characteristics of the device, and FIG. 26 shows the electric current density-external quantum efficiency characteristics of the device.

Figure 27:
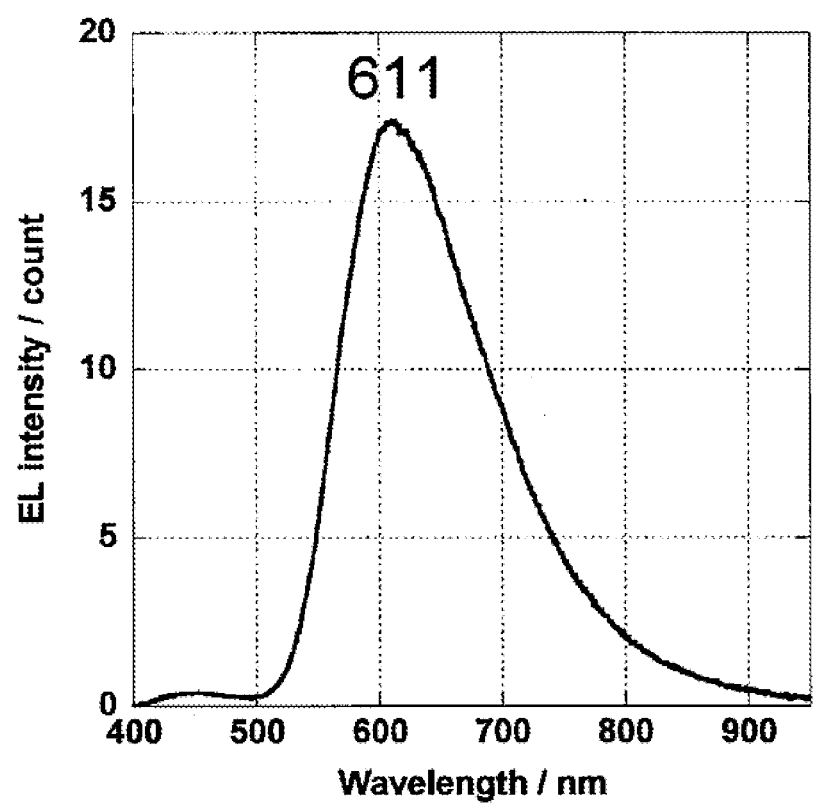
FIG. 27 is a light emission spectrum of an organic electroluminescent device using a compound 13 of Example 3.

FIG. 27 shows the light emission spectrum of an organic electroluminescent device produced similarly by using the compound 13 instead of the compound 1.

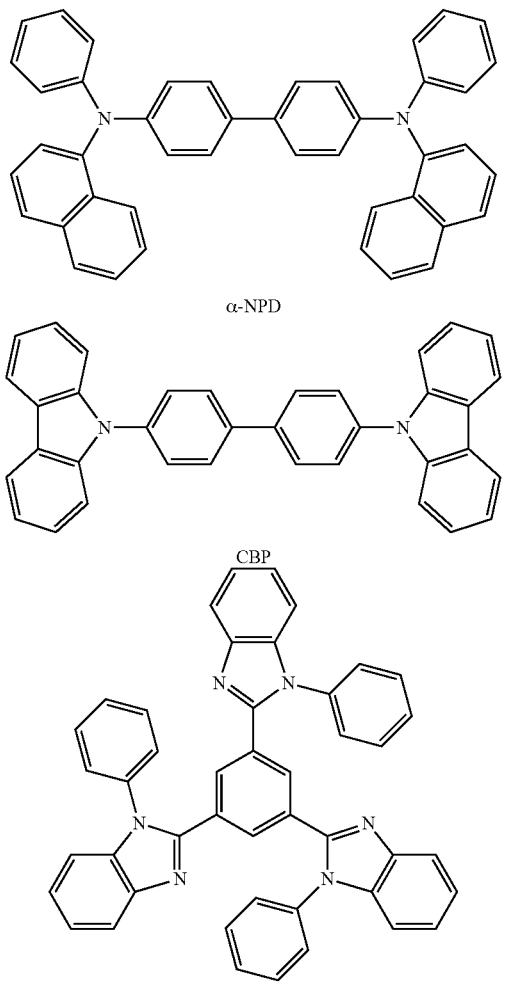

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus an organic light-emitting device having a high light emission efficiency may be provided. Accordingly, the invention has high industrial applicability.

REFERENCE SIGNS LIST 1 substrate
2 anode
3 hole injection layer
4 hole transporting layer
5 light-emitting layer
6 electron transporting layer
7 cathode

The invention claimed is:
1. A compound represented by the following general formula (1):

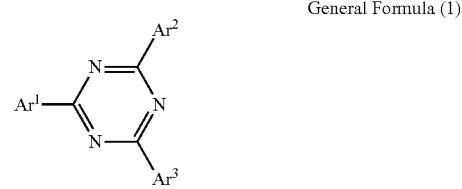

General Formula (1)

wherein in the general formula (1), $Ar^1$ to $Ar^3$ each independently represent a substituted or unsubstituted aryl group, provided that at least one thereof represents an aryl group substituted by a group represented by the following general formula (2):

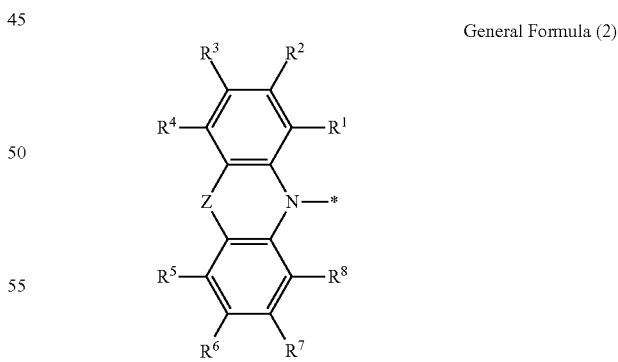

General Formula (2)

wherein in the general formula (2), * represents the bonding site to the triazine ring in the general formula (1); $R^1$ to $R^8$ each independently represent a hydrogen atom or a substituent; Z represents O, S, O=C or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, provided that neither $Ar^2$ nor $Ar^3$ is a phenyl group when Ar1 is a 4-(phenothiazin-10-yl)phenyl group, and provided that when one of the $Ar^1$ to $Ar^3$ is an aryl group substituted with a group represented by the general formula (2) wherein Z is O, S or O=C, then at least one of the other $Ar^1$ to $Ar^3$ has a group represented by the general formula (2).

2. The compound according to claim 1, wherein at least one of $Ar^1$ to $Ar^3$ in the general formula (1) represents an aryl group substituted by a group represented by the following general formula (3):

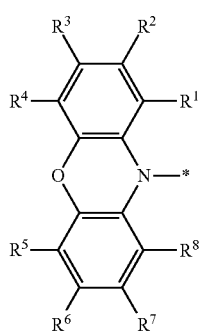

General Formula (3)

wherein in the general formula (3), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

3. The compound according to claim 1, wherein at least one of $Ar^1$ to $Ar^3$ in the general formula (1) represents an aryl group substituted by a group represented by the following general formula (4):

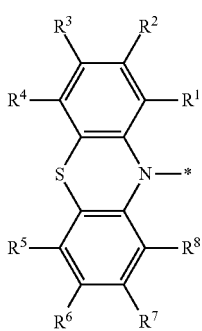

General Formula (4)

wherein in the general formula (4), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

4. The compound according to claim 1, wherein at least one of $Ar^1$ to $Ar^3$ in the general formula (1) represents an aryl group substituted by a group represented by the following general formula (5):

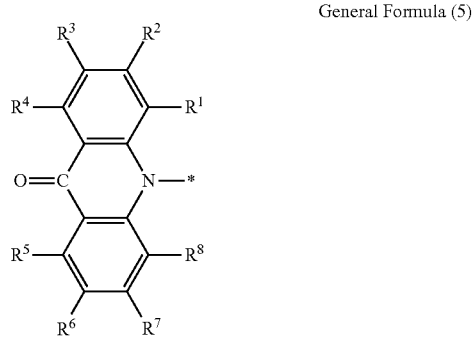

General Formula (5)

wherein in the general formula (5), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

5. The compound according to claim 1, wherein the compound has a structure represented by the following general formula (6):

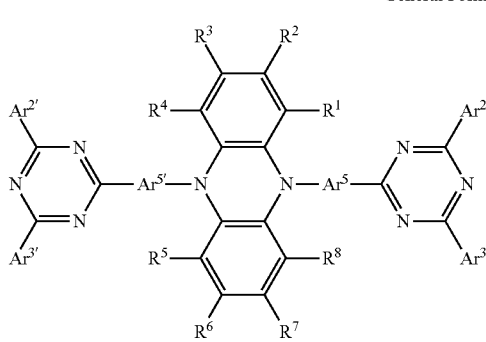

General Formula (6)

wherein in the general formula (6), $Ar^2$, $Ar^3$, $Ar^{2\prime}$ and $Ar^{3\prime}$ each independently represent a substituted or unsubstituted aryl group; $Ar^5$ and $Ar^{5\prime}$ each independently represent a substituted or unsubstituted arylene group; and $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

6. The compound according to claim 1, wherein the compound has a structure represented by the following general formula (7):

General Formula (7)

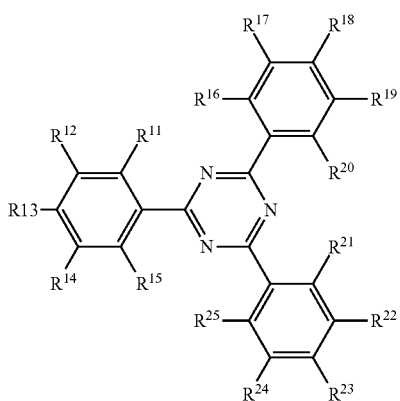

wherein in the general formula (7), at least one of $R^{11}$ to $R^{25}$ represents a group represented by the general formula (2) below, and the other thereof each independently represent a hydrogen atom or a substituent other than the general formula (2), provided that $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, and $R^{24}$ and $R^{25}$ each may be bonded to each other to form a cyclic structure:

General Formula (2)

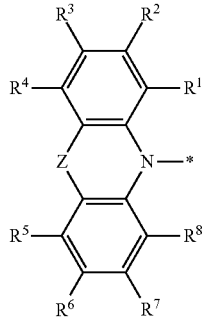

wherein in the general formula (2), * represents the bonding site to the triazine ring in the general formula (1); $R^1$ to $R^8$ each independently represent a hydrogen atom or a substituent; Z represents O, S, O=C or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

7. The compound according to claim 6, wherein at least one of $R^{11}$ to $R^{25}$ in the general formula (7) represents a group represented by the following general formula (3):

General Formula (3)

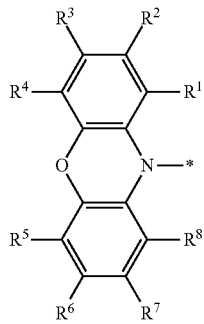

wherein in the general formula (3), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

8. The compound according to claim 6, wherein at least one of $R^{11}$ to $R^{25}$ in the general formula (7) represents a group represented by the following general formula (4):

General Formula (4)

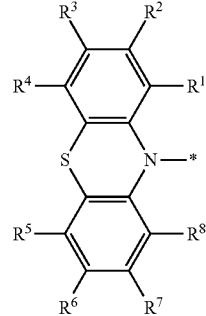

wherein in the general formula (4), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

9. The compound according to claim 6, wherein at least one of $R^{11}$ to $R^{25}$ in the general formula (7) represents a group represented by the following general formula (5):

General Formula (5)

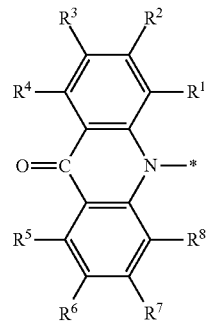

wherein in the general formula (5), * represents the bonding site to the triazine ring in the general formula (1); $R^1$ to $R^8$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

10. The compound according to claim 7, wherein the compound has a rotationally symmetric structure with the center of the triazine ring as the axis.

11. The compound according to claim 6, wherein the compound has a structure represented by the following general formula (8):

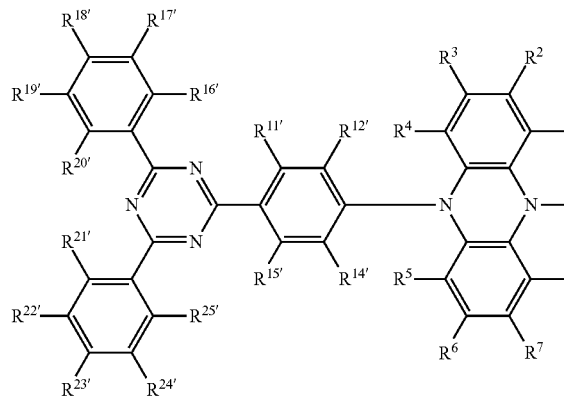
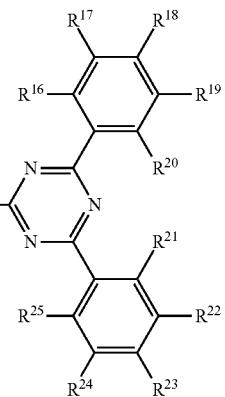

General Formula (8)

wherein in the general formula (8), $R^1$ to $R^8$, $R^{11}$, $R^{12}$, $R^{14}$ to $R^{25}$, $R^{11'}$, $R^{12'}$, and $R^{14'}$ to $R^{25'}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{11'}$ and $R^{12'}$, $R^{14'}$ and $R^{15'}$, $R^{16'}$ and $R^{17'}$, $R^{17'}$ and $R^{18'}$, $R^{18'}$ and $R^{19'}$, $R^{19'}$ and $R^{20'}$, $R^{21'}$ and $R^{22'}$, $R^{22'}$ and $R^{23'}$, $R^{23'}$ and $R^{24'}$, and $R^{24'}$ and $R^{25'}$ each may be bonded to each other to form a cyclic structure.

12. An organic light-emitting device containing a substrate having thereon a light-emitting layer that contains a host material and a light-emitting material containing a compound represented by the following general formula (1):

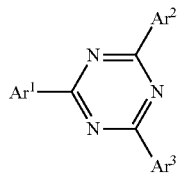

General Formula (1)

wherein in the general formula (1), $Ar^1$ to $Ar^3$ each independently represent a substituted or unsubstituted aryl group, provided that at least one thereof represents an aryl group substituted by a group represented by the following general formula (2):

General Formula (2)

wherein in the general formula (2), * represents the bonding site to the triazine ring in the general formula (1); $R^1$ to $R^8$ each independently represent a hydrogen atom or a substituent; Z represents O, S, O=C or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, provided that neither $Ar^2$ nor $Ar^3$ is a phenyl group when $Ar^1$ is a 4-(phenothiazin-10-yl)phenyl group.

13. The organic light-emitting device according to claim 12, wherein the device emits delayed fluorescent light.

14. The organic light-emitting device according to claim 12, wherein the device is an organic electroluminescent device.

* * * * *